US012558123B2

(12) United States Patent
Kaufmann et al.

(10) Patent No.: US 12,558,123 B2
(45) Date of Patent: Feb. 24, 2026

(54) MODULAR IMPLANT DELIVERY AND POSITIONING SYSTEM

(71) Applicant: IotaMotion, Inc., Iowa City, IA (US)

(72) Inventors: Christopher Kaufmann, Iowa City, IA (US); Parker Reineke, Cedar Rapids, IA (US)

(73) Assignee: IotaMotion, Inc., Iowa City, IA (US)

( * ) Notice: Subject to any disclaimer, the term of this patent is extended or adjusted under 35 U.S.C. 154(b) by 75 days.

(21) Appl. No.: 18/743,727

(22) Filed: Jun. 14, 2024

(65) Prior Publication Data

US 2025/0009388 A1     Jan. 9, 2025

Related U.S. Application Data

(63) Continuation of application No. 17/180,087, filed on Feb. 19, 2021, now Pat. No. 12,042,173, which is a
(Continued)

(51) Int. Cl.
*A61B 17/34*          (2006.01)
*A61B 34/30*          (2016.01)
(Continued)

(52) U.S. Cl.
CPC .......... *A61B 17/3468* (2013.01); *A61B 34/30* (2016.02); *A61N 1/36038* (2017.08);
(Continued)

(58) Field of Classification Search
CPC ............... A61B 17/3468; A61B 34/30; A61B 2017/000398; A61B 2017/00477; A61N 1/36038; A61N 1/372
See application file for complete search history.

(56) References Cited

U.S. PATENT DOCUMENTS 3,610,877 A    10/1971  Driscoll
4,383,532 A     5/1983  Dickhudt
(Continued)

FOREIGN PATENT DOCUMENTS

AU      2016323477 B2     3/2017
AU      2021232688 A1    10/2021
(Continued)

OTHER PUBLICATIONS

"U.S. Appl. No. 15/759,643, Advisory Action mailed Jun. 8, 2021", 3 pgs.
(Continued)

*Primary Examiner* — Phong Son H Dang
(74) *Attorney, Agent, or Firm* — Schwegman Lundberg & Woessner, P.A.

(57) ABSTRACT

This document discusses, among other things, systems and methods for robotically assisted implantation of an implant in a patient. A system includes an implant-positioning unit configured to engage an elongate member of the implant, and a control console communicatively coupled to the external positioning unit. The control console can have a user interface that enables a user to input motion control instructions. The control console can generate a motion control signal, according to a specific motion control instruction, to control the external positioning unit to propel the implant into a target implant site. The system can be used to robotically control the delivery and positing of a cochlear implant during a hearing-preservation cochlear implant surgery.

20 Claims, 32 Drawing Sheets

Related U.S. Application Data continuation of application No. 16/926,335, filed on Jul. 10, 2020, now Pat. No. 10,945,761, which is a continuation-in-part of application No. PCT/US2019/020130, filed on Feb. 28, 2019, and a continuation-in-part of application No. 16/486,030, filed as application No. PCT/US2018/018182 on Feb. 14, 2018, now Pat. No. 10,987,513.

(60) Provisional application No. 62/640,964, filed on Mar. 9, 2018, provisional application No. 62/573,487, filed on Oct. 17, 2017, provisional application No. 62/458,846, filed on Feb. 14, 2017, provisional application No. 62/872,625, filed on Jul. 10, 2019.

(51) Int. Cl.
| | | |
|---|---|---|
| *A61N 1/36* | (2006.01) |
| *A61N 1/372* | (2006.01) |
| *A61B 17/00* | (2006.01) |

(52) U.S. Cl.
CPC .... *A61N 1/372* (2013.01); *A61B 2017/00398* (2013.01); *A61B 2017/00477* (2013.01)

(56) References Cited

U.S. PATENT DOCUMENTS

| | | |
|---|---|---|
| 4,532,930 A | 8/1985 | Crosby et al. |
| 4,637,404 A | 1/1987 | Gessman |
| 5,197,982 A | 3/1993 | Goldsmith, III et al. |
| 5,201,765 A | 4/1993 | Netterville et al. |
| 5,306,298 A | 4/1994 | Godley, III et al. |
| 5,593,439 A | 1/1997 | Cummings et al. |
| 5,758,396 A | 6/1998 | Jeon et al. |
| 6,497,645 B1 | 12/2002 | Halpern |
| 7,524,320 B2 | 4/2009 | Tierney et al. |
| 7,691,098 B2 | 4/2010 | Wallace et al. |
| 8,010,210 B2 | 8/2011 | Rau |
| 8,229,574 B2 | 7/2012 | Parker et al. |
| 8,583,261 B2 | 11/2013 | Llinas et al. |
| 8,594,799 B2 | 11/2013 | Haller et al. |
| 8,886,331 B2 | 11/2014 | Labadie et al. |
| 9,561,372 B2 | 2/2017 | Jiang et al. |
| 9,675,446 B2 | 6/2017 | Jaber et al. |
| 9,700,408 B1 | 7/2017 | Sataloff |
| 9,986,998 B2 | 6/2018 | Martin et al. |
| 10,085,806 B2 | 10/2018 | Hagn et al. |
| 10,945,761 B2 | 3/2021 | Kaufmann et al. |
| 10,987,513 B2 | 4/2021 | Kaufmann et al. |
| 11,167,137 B2 | 11/2021 | Kaufmann et al. |
| 11,241,576 B2 | 2/2022 | Hansen et al. |
| 12,011,594 B2 | 6/2024 | Kaufmann et al. |
| 12,042,173 B2 | 7/2024 | Kaufmann et al. |
| 2001/0014818 A1 | 8/2001 | Kennedy |
| 2002/0065480 A1 | 5/2002 | Hofmann |
| 2003/0171758 A1 | 9/2003 | Gibson et al. |
| 2003/0171787 A1 | 9/2003 | Money et al. |
| 2004/0236390 A1 | 11/2004 | Dadd et al. |
| 2005/0004627 A1 | 1/2005 | Gibson et al. |
| 2005/0245991 A1 | 11/2005 | Faltys et al. |
| 2006/0047318 A1 | 3/2006 | Pastore et al. |
| 2006/0241723 A1 | 10/2006 | Dadd et al. |
| 2007/0156123 A1 | 7/2007 | Moll et al. |
| 2007/0225787 A1 | 9/2007 | Simaan et al. |
| 2008/0077221 A1 | 3/2008 | Milojevic et al. |
| 2008/0097487 A1 | 4/2008 | Pool et al. |
| 2008/0188931 A1 | 8/2008 | Kwon |
| 2010/0114288 A1 | 5/2010 | Haller et al. |
| 2010/0145138 A1 | 6/2010 | Forsell |
| 2010/0145143 A1 | 6/2010 | Salomon et al. |
| 2011/0021903 A1 | 1/2011 | Strommer et al. |
| 2011/0066160 A1 | 3/2011 | Simaan et al. |
| 2011/0106101 A1 | 5/2011 | Tortonese |
| 2011/0208031 A1 | 8/2011 | Wolfe et al. |

| | | |
|---|---|---|
| 2011/0264038 A1 | 10/2011 | Fujimoto et al. |
| 2012/0041515 A1 | 2/2012 | Meskens et al. |
| 2012/0041531 A1 | 2/2012 | Dadd et al. |
| 2012/0071890 A1 | 3/2012 | Taylor et al. |
| 2012/0071895 A1 | 3/2012 | Stahler et al. |
| 2012/0150293 A1 | 6/2012 | Hoffman et al. |
| 2012/0191107 A1 | 7/2012 | Tanner et al. |
| 2013/0138117 A1 | 5/2013 | Abbott et al. |
| 2013/0172901 A1 | 7/2013 | Bozorg et al. |
| 2013/0245569 A1 | 9/2013 | Jolly et al. |
| 2013/0296884 A1 | 11/2013 | Taylor et al. |
| 2013/0331779 A1 | 12/2013 | Dhanasingh et al. |
| 2014/0135799 A1 | 5/2014 | Henderson |
| 2014/0200432 A1 | 7/2014 | Banerji et al. |
| 2014/0213988 A1 | 7/2014 | Perouse |
| 2014/0222207 A1 | 8/2014 | Bowling et al. |
| 2014/0276391 A1 | 9/2014 | Yu |
| 2014/0276948 A1 | 9/2014 | Zirps |
| 2014/0277441 A1 | 9/2014 | Reif et al. |
| 2014/0350640 A1 | 11/2014 | Patrick et al. |
| 2014/0358174 A1 | 12/2014 | Thenuwara et al. |
| 2015/0032123 A1 | 1/2015 | Jolly et al. |
| 2015/0032124 A1 | 1/2015 | Lenarz et al. |
| 2015/0105795 A1 | 4/2015 | Lenarz et al. |
| 2015/0342445 A1 | 12/2015 | Jones et al. |
| 2016/0038733 A1 | 2/2016 | Robinson et al. |
| 2016/0045747 A1 | 2/2016 | Jiang et al. |
| 2016/0056493 A1 | 2/2016 | Umeda et al. |
| 2016/0243367 A1 | 8/2016 | Li et al. |
| 2018/0021568 A1 | 1/2018 | Schachtele et al. |
| 2018/0064532 A1 | 3/2018 | Ho et al. |
| 2018/0242967 A1 | 8/2018 | Meade |
| 2019/0029668 A1 | 1/2019 | Meade et al. |
| 2019/0142247 A1 | 5/2019 | Maeda et al. |
| 2019/0282803 A1 | 9/2019 | Hansen et al. |
| 2020/0038106 A1 | 2/2020 | Pieper et al. |
| 2020/0046978 A1 | 2/2020 | Kaufmann et al. |
| 2020/0069386 A1 | 3/2020 | Betsugi et al. |
| 2020/0329950 A1 | 10/2020 | Shear et al. |
| 2020/0337725 A1 | 10/2020 | Kaufmann et al. |
| 2021/0077252 A1 | 3/2021 | Hoffman et al. |
| 2021/0093869 A1 | 4/2021 | Kaufmann et al. |
| 2021/0187294 A1 | 6/2021 | Kaufmann et al. |
| 2021/0187295 A1 | 6/2021 | Kaufmann et al. |
| 2021/0196318 A1 | 7/2021 | Kaufmann et al. |
| 2022/0118246 A1 | 4/2022 | Hansen et al. |
| 2023/0320751 A1 | 10/2023 | Kaufmann et al. |

FOREIGN PATENT DOCUMENTS

| | | |
|---|---|---|
| AU | 2020357745 B2 | 11/2023 |
| CA | 2997735 A1 | 3/2017 |
| CN | 101460219 A | 6/2009 |
| CN | 104958108 A | 10/2015 |
| CN | 107708616 A | 2/2018 |
| CN | 110430918 A | 11/2019 |
| CN | 112074254 A | 12/2020 |
| CN | 114010372 A | 2/2022 |
| CN | 115038398 A | 9/2022 |
| CN | 116712667 A | 9/2023 |
| EP | 0634941 B1 | 7/1997 |
| EP | 2113283 A1 | 11/2009 |
| EP | 2615992 B1 | 7/2016 |
| EP | 1906858 B1 | 11/2016 |
| EP | 3334492 A1 | 6/2018 |
| EP | 3334492 B1 | 6/2019 |
| EP | 3662971 A1 | 6/2020 |
| EP | 3582849 B1 | 8/2023 |
| WO | WO-2010113072 A2 | 10/2010 |
| WO | WO-2014145327 A1 | 9/2014 |
| WO | WO-2017048342 A1 | 3/2017 |
| WO | WO-2017177208 A1 | 10/2017 |
| WO | WO-2018152203 A2 | 8/2018 |
| WO | WO-2018152203 A3 | 10/2018 |
| WO | WO-2019173107 A1 | 9/2019 |
| WO | WO-2021067463 A1 | 4/2021 |
| WO | WO-2023245167 A2 | 12/2023 |
| WO | WO-2023245167 A3 | 2/2024 |

(56)          References Cited

FOREIGN PATENT DOCUMENTS

OTHER PUBLICATIONS

"U.S. Appl. No. 15/759,643, Corrected Notice of Allowability mailed Dec. 30, 2021", 2 pgs.
"U.S. Appl. No. 15/759,643, Final Office Action mailed Mar. 29, 2021", 13 pgs.
"U.S. Appl. No. 15/759,643, Non Final Office Action mailed Sep. 4, 2020", 15 pgs.
"U.S. Appl. No. 15/759,643, Notice of Allowance mailed Sep. 28, 2021", 10 pgs.
"U.S. Appl. No. 15/759,643, Preliminary Amendment filed Mar. 13, 2018", 12 pgs.
"U.S. Appl. No. 15/759,643, Response filed Jun. 1, 2021 to Final Office Action mailed Mar. 29, 2021", 9 pgs.
"U.S. Appl. No. 15/759,643, Response filed Dec. 4, 2020 to Non Final Office Action mailed Sep. 4, 2020", 9 pgs.
"U.S. Appl. No. 16/486,030, Corrected Notice of Allowability mailed Jan. 12, 2021", 7 pgs.
"U.S. Appl. No. 16/486,030, Non Final Office Action mailed Sep. 8, 2020", 12 pgs.
"U.S. Appl. No. 16/486,030, Notice of Allowance mailed Dec. 24, 2020", 11 pgs.
"U.S. Appl. No. 16/486,030, Preliminary Amendment Filed Aug. 14, 2019", 10 pgs.
"U.S. Appl. No. 16/486,030, Response filed Aug. 10, 2020 to Restriction Requirement mailed Jun. 11, 2020", 8 pgs.
"U.S. Appl. No. 16/486,030, Response filed Dec. 8, 2020 to Non Final Office Action mailed Sep. 8, 2020", 12 pgs.
"U.S. Appl. No. 16/486,030, Restriction Requirement mailed Jun. 11, 2020", 7 pgs.
"U.S. Appl. No. 16/486,030, Supplemental Preliminary Amendment filed", 8 pgs.
"U.S. Appl. No. 16/926,335, Notice of Allowance mailed Nov. 9, 2020", 14 pgs.
"U.S. Appl. No. 16/926,335, Response filed Oct. 2, 2020 to Restriction Requirement mailed Aug. 4, 2020", 9 pgs.
"U.S. Appl. No. 16/926,335, Restriction Requirement mailed Aug. 4, 2020", 6 pgs.
"U.S. Appl. No. 16/979,427 Preliminary Amendment filed Sep. 9, 2020", 10 pgs.
"U.S. Appl. No. 16/979,427, Non Final Office Action mailed Oct. 31, 2023", 14 pgs.
"U.S. Appl. No. 17/038,916, Examiner Interview Summary mailed Dec. 19, 2023", 2 pgs.
"U.S. Appl. No. 17/038,916, Final Office Action mailed Nov. 9, 2023", 9 pgs.
"U.S. Appl. No. 17/038,916, Non Final Office Action mailed Apr. 27, 2023", 7 pgs.
"U.S. Appl. No. 17/038,916, Notice of Allowance mailed Jun. 26, 2024", 13 pgs.
"U.S. Appl. No. 17/038,916, Response filed Feb. 8, 2024 to Final Office Action mailed Nov. 9, 2023", 9 pgs.
"U.S. Appl. No. 17/038,916, Response filed Mar. 20, 2023 to Restriction Requirement mailed Jan. 20, 2023", 7 pgs.
"U.S. Appl. No. 17/038,916, Response filed Jul. 27, 2023 to Non Final Office Action mailed Apr. 27, 2023", 10 pgs.
"U.S. Appl. No. 17/038,916, Restriction Requirement mailed Jan. 20, 2023", 7 pgs.
"U.S. Appl. No. 17/180,087, Corrected Notice of Allowability mailed Jun. 25, 2024", 2 pgs.
"U.S. Appl. No. 17/180,087, Notice of Allowance mailed Mar. 14, 2024", 14 pgs.
"U.S. Appl. No. 17/180,087, Preliminary Amendment filed Apr. 12, 2021", 7 pgs.
"U.S. Appl. No. 17/196,690, Corrected Notice of Allowability mailed Feb. 28, 2024", 2 pgs.
"U.S. Appl. No. 17/196,690, Final Office Action mailed Jul. 10, 2023", 13 pgs.

"U.S. Appl. No. 17/196,690, Non Final Office Action mailed Sep. 28, 2023", 12 pgs.
"U.S. Appl. No. 17/196,690, Non Final Office Action mailed Dec. 22, 2022", 18 pgs.
"U.S. Appl. No. 17/196,690, Notice of Allowance mailed Feb. 12, 2024", 8 pgs.
"U.S. Appl. No. 17/196,690, Response filed Mar. 22, 2023 to Non Final Office Action mailed Dec. 22, 2022", 10 pgs.
"U.S. Appl. No. 17/196,690, Response filed Sep. 11, 2023 to Final Office Action mailed Jul. 10, 2023", 8 pgs.
"U.S. Appl. No. 17/196,690, Response filed Dec. 20, 2023 to Non Final Office Action mailed Sep. 28, 2023", 7 pgs.
"U.S. Appl. No. 17/196,723, 312 Amendment filed Sep. 21, 2021", 2 pgs.
"U.S. Appl. No. 17/196,723, Corrected Notice of Allowability mailed Jul. 7, 2021", 2 pgs.
"U.S. Appl. No. 17/196,723, Notice of Allowance mailed Jun. 23, 2021", 8 pgs.
"U.S. Appl. No. 17/196,723, PTO Response to Rule 312 Communication mailed Sep. 28, 2021", 2 pgs.
"U.S. Appl. No. 17/561,260, Examiner Interview Summary mailed Dec. 14, 2023", 3 pgs.
"U.S. Appl. No. 17/561,260, Final Office Action mailed Oct. 16, 2023", 20 pgs.
"U.S. Appl. No. 17/561,260, Non Final Office Action mailed Mar. 28, 2024", 11 pgs.
"U.S. Appl. No. 17/561,260, Non Final Office Action mailed Mar. 30, 2023", 16 pgs.
"U.S. Appl. No. 17/561,260, Preliminary Amendment filed Feb. 28, 2022", 7 pgs.
"U.S. Appl. No. 17/561,260, Response filed Jan. 16, 2024 to Final Office Action mailed Oct. 16, 2023", 11 pgs.
"U.S. Appl. No. 17/561,260, Response filed Jun. 29, 2023 to Non Final Office Action mailed Mar. 30, 2023", 10 pgs.
"U.S. Appl. No. 18/661,059, Non Final Office Action mailed Aug. 29, 2024", 13 pgs.
"Australian Application Serial No. 2016323477, First Examination Report mailed Jun. 29, 2020", 3 pgs.
"Australian Application Serial No. 2016323477, Response filed Dec. 10, 2020 to First Examination Report mailed Jun. 29, 2020", 19 pgs.
"Australian Application Serial No. 2019231573, First Examination Report mailed Feb. 8, 2021", 6 pgs.
"Australian Application Serial No. 2019231573, Response filed Apr. 27, 2021 to First Examination Report mailed Feb. 8, 2021", 40 pgs.
"Australian Application Serial No. 2019231573, Response filed Sep. 4, 2021 to Subsequent Examiners Report mailed May 11, 2021", 26 pgs.
"Australian Application Serial No. 2019231573, Subsequent Examiners Report mailed May 11, 2021", 3 pgs.
"Australian Application Serial No. 2020357745, First Examination Report mailed Mar. 16, 2023", 4 pgs.
"Australian Application Serial No. 2020357745, Response filed Jun. 13, 2023 to First Examination Report mailed Mar. 16, 2023", 74 pgs.
"Australian Application Serial No. 2020357745, Response filed Oct. 10, 2023 to Subsequent Examiners Report mailed Jul. 13, 2023", 3 pgs.
"Australian Application Serial No. 2020357745, Subsequent Examiners Report mailed Jul. 13, 2023", 3 pgs.
"Australian Application Serial No. 2021232688, First Examination Report mailed Apr. 1, 2022", 4 pgs.
"Australian Application Serial No. 2021232688, Response filed Jul. 12, 2022 to First Examination Report mailed Apr. 1, 2022", 115 pgs.
"Canadian Application Serial No. 2997735, Office Action mailed Jun. 17, 2021", 4 pgs.
"Canadian Application Serial No. 2997735, Response filed Sep. 20, 2021 to Office Action Mailed Jun. 17, 2021", 62 pgs.
"Chinese Application Serial No. 201980030326.X, Office Action mailed Feb. 11, 2023", w/ English Translation, 23 pgs.
"Chinese Application Serial No. 201880011446.0, Office Action mailed Sep. 28, 2022", w/English Translation, 16 pgs.

(56) References Cited

OTHER PUBLICATIONS

"Chinese Application Serial No. 201880011446.0, Response filed Jan. 17, 2023 to Office Action mailed Sep. 28, 2022", w/ English claims, 12 pgs.

"Chinese Application Serial No. 201880011446.0, Voluntary Amendment filed Feb. 28, 2020", w/ English claims, 7 pgs.

"Chinese Application Serial No. 201980030326.X, Office Action mailed Sep. 20, 2023", w/English Translation, 21 pgs.

"Chinese Application Serial No. 201980030326.X, Response filed Jun. 9, 2023 to Office Action mailed Feb. 11, 2023", w/ English Claims, 12 pgs.

"Chinese Application Serial No. 201980030326.X, Response filed Nov. 20, 2023 to Office Action mailed Sep. 20, 2023", w/ English claims, 12 pgs.

"Chinese Application Serial No. 201980030326.X, Voluntary Amendment filed Mar. 24, 2021", with English translation of claims, 13 pgs.

"Chinese Application Serial No. 201980038179.0, Response to Examiner Telephone Interview filed Aug. 25, 2022", w/ English claims, 46 pgs.

"Chinese Application Serial No. 202080076185.8, Notification to Make Rectification mailed May 24, 2022", with machine translation, 2 pgs.

"European Application Serial No. 16736687.1, Intention to Grant mailed Jan. 7, 2019", 48 pgs.

"European Application Serial No. 18707575.9, Communication under Rule 71(3) EPC mailed May 9, 2022", 72 pgs.

"European Application Serial No. 18707575.9, Communication under Rule 71(3) EPC mailed Oct. 27, 2022", 76 pgs.

"European Application Serial No. 18707575.9, Response to Communication Pursuant to Rules 161 and 162 filed Feb. 25, 2020", 23 pgs.

"European Application Serial No. 19173377.3, Extended European Search Report mailed Mar. 4, 2020", 4 pgs.

"European Application Serial No. 19173377.3, Response filed Oct. 25, 2020 to Extended European Search Report mailed Mar. 4, 2020", 22 pgs.

"European Application Serial No. 19710939.0, Communication Pursuant to Article 94(3) EPC mailed May 6, 2024", 6 pgs.

"European Application Serial No. 19710939.0, Response to Communication pursuant to Rules 161(1) and 162 EPC filed Apr. 15, 2021", 29 pgs.

"European Application Serial No. 20870940.2, Extended European Search Report mailed Feb. 2, 2024", 10 pgs.

"European Application Serial No. 21192166.3, Extended European Search Report mailed Dec. 16, 2021", 11 pgs.

"European Application Serial No. 21192166.3, Response filed Jul. 1, 2022 to Extended European Search Report mailed Dec. 16, 2021", 29 pgs.

"European Application Serial No. 23190893.0, Extended European Search Report mailed Oct. 31, 2023", 6 pgs.

"European Application Serial No. 23190893.0, Response filed May 17, 2024 to Communication Pursuant to EPC Rule 69 mailed Dec. 4, 2023", 10 pgs.

"International Application Serial No. PCT/US2016/039342, International Preliminary Report on Patentability mailed Mar. 29, 2018", 9 pgs.

"International Application Serial No. PCT/US2016/039342, International Search Report mailed Oct. 6, 2016", 4 pgs.

"International Application Serial No. PCT/US2016/039342, Written Opinion mailed Oct. 6, 2016", 7 pgs.

"International Application Serial No. PCT/US2018/018182, International Preliminary Report on Patentability mailed Aug. 29, 2019", 14 pgs.

"International Application Serial No. PCT/US2018/018182, International Search Report mailed Sep. 10, 2018", 7 pgs.

"International Application Serial No. PCT/US2018/018182, Invitation to Pay Add'l Fees and Partial Search Report mailed May 23, 2018", 15 pgs.

"International Application Serial No. PCT/US2018/018182, Written Opinion mailed Sep. 10, 2018", 12 pgs.

"International Application Serial No. PCT/US2019/020130, International Preliminary Report on Patentability mailed Sep. 24, 2020", 7 pgs.

"International Application Serial No. PCT/US2019/020130, International Search Report mailed Jun. 12, 2019", 7 pgs.

"International Application Serial No. PCT/US2019/020130, Written Opinion mailed Jun. 12, 2019", 10 pgs.

"International Application Serial No. PCT/US2020/053579, International Preliminary Report on Patentability mailed Apr. 14, 2022", 10 pgs.

"International Application Serial No. PCT/US2020/053579, International Search Report mailed Jan. 18, 2021", 3 pgs.

"International Application Serial No. PCT/US2020/053579, Written Opinion mailed Jan. 18, 2021", 8 pgs.

"International Application Serial No. PCT/US2023/068582, International Search Report mailed Dec. 21, 2023", 4 pgs.

"International Application Serial No. PCT/US2023/068582, Invitation to Pay Additional Fees mailed Oct. 31, 2023", 5 pgs.

"International Application Serial No. PCT/US2023/068582, Written Opinion mailed Dec. 21, 2023", 10 pgs.

Campbell, Luke, et al., "Intraoperative Real-time Cochlear Response Telemetry Predicts Hearing Preservation in Cochlear Implantation", Otology & Neurotology; vol. 37(4), (Apr. 2016), 10 pgs.

Dahm, MC, et al., "The postnatal growth of the temporal bone and its implications for cochlear implantation in children", Acta Otolaryngol Suppl. 505, (1993), 4-39.

Desrosiers, M, et al., "Precise vocal cord medialization using an adjustable laryngeal implant: a preliminary study", Otolaryngol Head Neck Sur, 109(6), (1993), 1014-1019.

Fasano, Alfonso, et al., "MDS SIC Blog: Recent Advances in Deep Brain Stimulation (DBS) Technology", International Parkinson and Movement Disorder Society, [Online]. Retrieved from the Internet: <URL: https://www.movementdisorders.org/MDS/Scientific-Issues-Committee-Blog/Recent-Advances-in-DBS-Technology.htm>, (Mar. 2018), 3 pgs.

Gantz, Bruce J., et al., "Hybrid 10 Clinical Trial", Audiol Neurotol 2009;14(suppl 1):DOI: 10.1159/000206493, (2009), 7 pgs.

Greene, Nathaniel, et al., "Intracochlear pressure transients during cochlear implant electrode insertion", Otol Neurotol. 37(10), (2016), 1541-1548.

Jurawitz, Marie-Charlot, et al., "Hearing Preservation Outcomes with Different Cochlear Implant Electrodes: Nucleus ® Hybrid TM-L24 and Nucleus Freedom TM CI422", Audiol Neurotol 2014; 19: 293-309; DOI: 10.1159/000360601, (2014), 17 pgs.

Mittmann, Phillipp, et al., "Intracochlear Pressure Changes due to 2 Electrode Types: An Artificial Model Experiment", Otolaryngology—Head and Neck Surgery, vol. 156(4), (Dec. 2016), 712-716.

Montgomery, William, et al., "Montgomery Thyroplasty Implant for vocal fold immobility: phonatory outcomes", Ann Otol Rhinol Laryngol, 109(4), (2000), 393-400.

Mowry, Sarah E., et al., "New Frontiers in Cochlear Implantation: Acoustic Plus Electric Hearing, Hearing Preservation, and More", Otolaryngologic Clinics of North America. vol. 45, Issue 1., (2012), 187-203.

Woodson, Erika A., et al., "The Hybrid Cochlear Implant: A Review", Cochlear Implants and Hearing Preservation. Adv Otorhinolaryngol. Basel, Karger, 2010, vol. 67., (2010), 125-134.

U.S. Appl. No. 16/486,030 U.S. Pat. No. 10,987,513, filed Aug. 14, 2019, Modular Implant Delivery and Positioning System.

U.S. Appl. No. 17/196,690 U.S. Pat. No. 12,011,594, filed Mar. 9, 2021, Modular Implant Delivery and Positioning System.

U.S. Appl. No. 17/196,723 U.S. Pat. No. 11,167,137, filed Mar. 9, 2021, Modular Implant Delivery and Positioning System.

U.S. Appl. No. 18/661,059, filed May 10, 2024, Modular Implant Delivery and Positioning System.

U.S. Appl. No. 16/979,427, filed Sep. 9, 2020, Dynamically Controlled Soft Tissue Manipulator.

U.S. Appl. No. 16/926,335 U.S. Pat. No. 10,945,761, filed Jul. 10, 2020, Modular Implant Delivery and Positioning System.

U.S. Appl. No. 17/180,087 U.S. Pat. No. 12,042,173, filed Feb. 19, 2021, Modular Implant Delivery and Positioning System.

(56)         References Cited

OTHER PUBLICATIONS

U.S. Appl. No. 17/038,916 U.S. Pat. No. 12,128,242, filed Sep. 30, 2020, Modular Implant Delivery and Positioning System.
U.S. Appl. No. 18/336,448, filed Jun. 16, 2023, Systems and Methods for Manipulation of Perimodiolar Electrode Arrays.

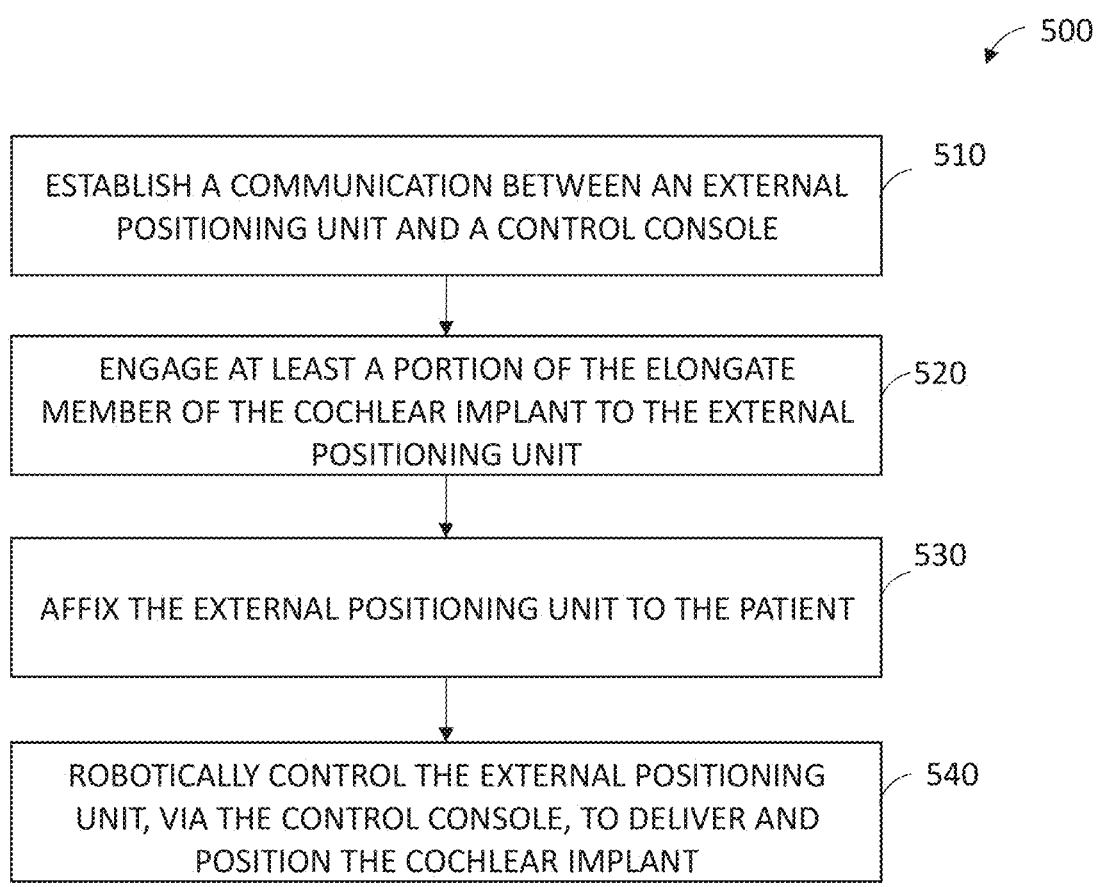

500

ESTABLISH A COMMUNICATION BETWEEN AN EXTERNAL POSITIONING UNIT AND A CONTROL CONSOLE — 510

ENGAGE AT LEAST A PORTION OF THE ELONGATE MEMBER OF THE COCHLEAR IMPLANT TO THE EXTERNAL POSITIONING UNIT — 520

AFFIX THE EXTERNAL POSITIONING UNIT TO THE PATIENT — 530

ROBOTICALLY CONTROL THE EXTERNAL POSITIONING UNIT, VIA THE CONTROL CONSOLE, TO DELIVER AND POSITION THE COCHLEAR IMPLANT — 540

FIG. 5

MODULAR IMPLANT DELIVERY AND POSITIONING SYSTEM

TECHNICAL FIELD

This document relates generally to medical systems and more particularly to systems, devices, and methods for robotic control of delivery, positioning, and manipulation of an implant.

BACKGROUND

The cochlea is the auditory portion of the inner ear. It comprises a spiraled, hollow, conical chamber of bone in which sound waves propagate from the base to the apex of the cochlea. The sound waves vibrate the perilymph that moves hair cells in the organ of Corti, converting the vibrations to electrical signals that are sent to the cochlear nerve. The hair cells and nerves in the basal or outer region of the spiraled cochlea are more sensitive to higher frequencies of sound, and are frequently the first part of the cochlea to lose sensitivity. The apical or inner region of the spiraled cochlea is more sensitive to lower frequencies.

Moderate to profound hearing loss affects a large amount of people worldwide, and can have a significant impact on a patient physical and mental health, education, employment, and overall quality of life. Hearing loss can be caused by partial damage to the cochlea. Many patients with various degrees of hearing loss have partial damage to the cochlea in the high-frequency regions (basal cochlea) from common causes such as noise exposure, drugs, genetic mutations or aging, but can retain adequate low-frequency hearing.

Cochlear implants have been used to treat patients with hearing loss. A cochlear implant is a medical device that comprises an external sound processor, a subcutaneously implantable stimulator, and an electrode assembly sized and shaped for cochlear insertion. The sound processor can convert sound signals into electrical signals, and transmit the electrical signals to the implantable stimulator. Based on the physical properties (e.g., frequencies) of the received electrical signals, the stimulator can generate electrical impulses to stimulate specific regions in the cochlea via an array of electrodes on the electrode assembly surgically inserted into the cochlea. The region for stimulation can be determined based on the frequencies of the received electrical signals. For example, higher frequencies can result in stimulation at the outer or basal cochlear region, and lower frequencies can result in stimulation at the inner or apical cochlear region.

For patients who have lost high-frequency hearing and consequently have significant difficulty with word understanding but who have substantial residual, low-frequency hearing function in apical cochlea, a short electrode assembly can be indicated to electrically stimulate the basal or outer cochlea to restore high-frequency hearing. A cochlear implant surgery can be performed by a surgeon to manually insert the electrode assembly into the damaged portion of a patient cochlea (e.g., basal cochlea), while avoiding or minimizing any trauma to the undamaged cochlear regions to preserve the low-frequency hearing function. The cochlear implant can be used together with a hearing aid that acoustically stimulates the undamaged low-frequency sensitive apical cochlea.

Intracochlear trauma can occur from large pressure spikes generated during the insertion of cochlear implant electrodes. Cochlear implant surgery can also involve insertion of a guide sheath or tube near or partially into the cochlea. Insertion of any solid or flexible bodies, tubes, or sheaths into the cochlea could elicit similar fluid and force spikes. These pressures spikes can be of sufficient intensity to cause trauma similar to that of an acoustic blast injury and are one likely source for postoperative loss of residual hearing. Similar to the insertion trauma cause by electrode insertion, the manual insertion of a sheath or other solid body/tube manually into the cochlea can cause intracochlear fluid pressure spikes and result in intracochlear damage.

SUMMARY

A hearing-preservation cochlear implant surgery involves implanting an electrode assembly into the damaged cochlear region, while avoiding any trauma to the undamaged cochlear region to preserve any normal residual hearing. In current cochlear implant surgery, a surgeon manually inserts an electrode assembly into patient cochlea. However, a complete manual maneuvering of the electrode assembly can cause undesirable outcome in some patients. For example, manual insertion of electrode assembly can lack precision in implant position and motion control, such as the control of insertion rate, distance, or forces applied to the implant for advancing the electrode assembly to the target cochlear region. This can cause damage to fragile cochlear structures such as local trauma to cochlea wall and hair cells, and result in residual hearing loss.

Complete manual maneuvering of the electrode assembly can also be subject to high inter-operator variability among surgeons. The inter-operator variability is demonstrated in dramatic differences in patient outcomes between institutions and surgeons of differing skill levels. Some patients undergoing hearing-preservation cochlear implant surgery can experience additional hearing decline weeks to years after surgery. Such a continual decline in hearing function can be attributed to an inflammatory response to the trauma inflicted during an initial cochlear implant surgery. Some clinical studies show that techniques aimed at reducing electrode-insertion forces during surgery have improved patient hearing preservation outcomes. For at least reasons, the present inventors have recognized that there remains a need to improve patient outcome following a hearing-preservation cochlear implant surgery, particularly systems, apparatus, and methods that enhance surgical precision in implant delivery and positioning, and reduce the risk of perioperative trauma to undamaged cochlea region.

This document discusses, among other things, systems, devices, and methods for robotically assisted implantation of an implant in a patient, such as for delivering and positioning a cochlear implant for treating hearing loss in a hearing-preservation cochlear implant surgery. The systems and devices discussed can also be adapted for robotically controlling insertion of a guide sheath or tube that can be used in conjunction with electrode implantation. The modular system discussed herein includes an external positioning unit reversibly interfacing with and securely engaging an implant such as a cochlear implant having an elongate member, and a computerized control unit for robotically controlling the external positioning unit to regulate the motion of the implant. The computerized control unit can have a user interface that enables a user (e.g., a surgeon) to program various motion control parameters or to select an implantation protocol. The system can include sensors providing feedback on the position or the motion of the implant, or the force or friction applied to the implant during the implantation procedure. The computerized control unit can regulate the motion of the implant based on user input and the sensor feedback. The control systems can also interface with external systems providing electrophysiological measurements to enable closed loop feedback on electrode positioning in real-time during implantation.

Example 1 is a system for robotically assisted manipulation of an implant, the system comprising: a drive head configured to engage an elongate member of the implant and robotically deliver and position the implant into a target implantation site, the drive head including: a housing including a first half and a second half, the first half coupled to the second half with a hinge, to enable the housing to receive the elongate member; a guide track configured to accommodate and channel the elongate member in a linear motion; and a coupling unit including a wheel, the coupling unit configured to translate the elongate member using the wheel within the guide track, in response to a motion control signal; a power system electrically coupled to the coupling unit, the power system including a motor and motor control circuitry positioned within the housing and configured to drive the wheel of the coupling unit; and a control console communicatively coupled to the power system, the control console including a controller circuit configured to generate the motion control signal, to robotically deliver and position the implant into the target implantation site.

In Example 2, the subject matter of Example 1 includes, where the guide track includes a first longitudinal track portion and a second longitudinal track portion, the first longitudinal track portion defined by the first half of the housing, and the second longitudinal track portion defined by the second half of the housing.

In Example 3, the subject matter of Example 2 includes, wherein the drive head includes: an entrance port to receive the elongate member; and an exit port to release the elongate member from the drive head, wherein the guide track is located between the entrance port and the exit port.

In Example 4, the subject matter of Examples 1-3 includes, wherein the drive head includes an implant access port open to the first or the second longitudinal track portions, the implant access port configured to enable access to the elongate member from a location external to the drive head.

In Example 5, the subject matter of Examples 2-4 includes, wherein the first and the second longitudinal track portions include a groove configured to accommodate the elongate member and limit rotation or twisting during translation of the elongate member.

In Example 6, the subject matter of Examples 2-5 includes, wherein the first and the second longitudinal track portions are in parallel and are configured to accommodate the implant, the first and the second longitudinal track portions together forming a keyhole-shaped cross section of the guide track.

In Example 7, the subject matter of Examples 2-6 includes, wherein the first longitudinal track portion defines a cylindrical groove, and the second longitudinal track portion defines a rectangular groove.

In Example 8, the subject matter of Example 7 includes, wherein the implant includes an access tab attached to, and projecting from, the electrode array, and wherein the rectangular groove of the second longitudinal track portion is configured to accommodate the electrode array and the access tab by engaging the access tab to limit rotation or twisting of the implant during translation.

In Example 9, the subject matter of Example 8 includes, wherein the access tab includes a flange.

In Example 10, the subject matter of Examples 1-9 includes, wherein a first portion of the implant includes the elongate member and a second portion of the implant includes an electrode array, the electrode array detachably connected to the elongate member.

In Example 11, the subject matter of Examples 1-10 includes, wherein the implant is a cochlear implant.

In Example 12, the subject matter of Examples 1-11 includes, wherein the drive head includes a locking mechanism configured to releaseably lock the wheel of the drive head, to limit longitudinal translation of the elongate member within the guide track.

In Example 13, the subject matter of Example 12 includes, wherein the locking mechanism includes one or more of a locking tab, a clip lock, or a push plug.

In Example 14, the subject matter of Examples 1-13 includes, wherein the coupling unit includes at least two wheels configured to engage at least a portion of the elongate member, through compression between portions of radial outer surfaces of the at least two wheels, to rotate to propel the elongate member via friction generated by the compression.

Example 15 is a system for robotically assisted manipulation of an implant, the system comprising: a drive head configured to engage an elongate member of the implant and robotically deliver and position the implant into a target implantation site, the drive head including: a housing including a first half, a second half, and a hinge movably coupling the first half with the second half to enable the housing to receive the elongate member; a guide track configured to accommodate and channel the elongate member in a linear motion; a coupling unit including a wheel, the coupling unit configured to translate the elongate member using the wheel within the guide track, in response to a motion control signal; a control console communicatively coupled to the power system, the control console including a controller circuit configured to generate the motion control signal, to robotically deliver and position the implant into the target implantation site.

In Example 16, the subject matter of Example 15 includes, where the guide track includes a first longitudinal track portion and a second longitudinal track portion.

In Example 17, the subject matter of Examples 15-16 includes, wherein the user interface includes a touchscreen and the graphical user interface is displayed on the touchscreen, the touchscreen configured to receive contact input from the user to operate the control console and the drive head.

In Example 18, the subject matter of Example 17 includes, a foot pedal communicatively coupled to the control console, the foot pedal operable to control translation of the drive head.

In Example 19, the subject matter of Example 18 includes, wherein the foot pedal includes a first pedal and a second pedal, the first pedal configured to control translation of the elongate member in a first direction, and the second pedal configured to control translation of the elongate member in a second direction.

In Example 20, the subject matter of Examples 15-19 includes, wherein the drive head includes a first guide track and a second guide track, the first guide track configured to accommodate a first elongate member and the second guide track configured to accommodate a second elongate member different from the first elongate member.

In Example 21, the subject matter of Example 20 includes, wherein the first and the second guide tracks are in parallel and adjacent to each other.

In Example 22, the subject matter of Examples 20-21 includes, wherein the first and the second guide tracks each include a groove configured to accommodate the respective first and second elongate members and to limit rotation or twisting during translation of the respective first and second elongate members.

In Example 23, the subject matter of Examples 20-22 includes, wherein the coupling unit includes the wheel as a first wheel and a second wheel, wherein the first wheel and the second wheel are configured to coupling unit includes the wheel as a first wheel and a second wheel, the wheel and the second wheel together configured to engage at least a portion of the first and the second elongate members through compression between respective portions of radial outer surfaces of the wheel and the second wheel, to rotate to propel the elongate member via friction generated by the compression.

In Example 24, the subject matter of Example 23 includes, wherein the first wheel includes a first guide groove configured to engage the first elongate member and the second wheel includes a second guide groove configured to engage the second elongate member.

In Example 25, the subject matter of Examples 20-24 includes, wherein the first elongate member includes a sheath, and the second elongate member includes an electrode array at least partially enclosed in the sheath, and the coupling unit is configured to engage the second elongate member to move the second elongate member out of the drive head.

In Example 26, the subject matter of Example 25 includes, wherein the coupling unit is configured to engage the first elongate member to move the first elongate member out of the drive head and pass through the sheath.

Example 27 is an apparatus for robotically assisted implantation of an implant having an electrode array disposed on a first elongate member, the apparatus comprising: a drive head including a first half, a second half, and a hinge pivotally coupling the first half to the second half to enable insertion of the first elongate member into the drive head; at least two wheels arranged within the drive head to compress at least a portion of the first elongate member between portions of radial outer surfaces of each wheel and to translate the first elongate member to deliver an implant to a target implantation site; a guide track configured to accommodate and channel the first elongate member during linear translation; a power system including a motor and motor control circuitry configured to drive the at least two wheels to translate the first elongate member; and a control console communicatively coupled to the power system, the control console including a controller circuit configured to generate a motion control signal for controlling translation of the first elongate member via the at least two wheels.

In Example 28, the subject matter of Example 27 includes, wherein the guide track includes a first and a second longitudinal track portion, the first and the second longitudinal track portions configured to accommodate and channel the first elongate member during linear translation.

In Example 29, the subject matter of Example 28 includes, wherein the first and the second longitudinal track portions are in parallel and are configured to accommodate the first elongate member, the first and the second longitudinal track portions together forming a keyhole-shaped cross section of the guide track.

In Example 30, the subject matter of Examples 27-29 includes, wherein the guide track includes an entrance port, to receive the first elongate member, and an exit port, to release the first elongate member, and wherein the guide track defining a lumen that extends between the entrance port and the exit port.

In Example 31, the subject matter of Examples 27-30 includes, a user interface configured to display a graphical user interface to a user, the user interface communicatively coupled to the control console, and the user interface configured to receive an input from a user and communicate the input to the control console, which operates the drive head in response to the input.

Example 32 is at least one machine-readable medium including instructions that, when executed by processing circuitry, cause the processing circuitry to perform operations to implement of any of Examples 1-31.

Example 33 is an apparatus comprising means to implement of any of Examples 1-31.

Example 34 is a system to implement of any of Examples 1-31.

Example 35 is a method to implement of any of Examples 1-31.

The systems, devices, and methods discussed in this document can improve the technological field of robotic surgery, particularly robotically assisted implantation of an implant or prosthesis. For example, when the systems or methods discussed herein are used in hearing-preservation cochlear implant surgery, the robotic motion control of the cochlear implant can reduce the mechanical forces imposed on the delicate cochlear structure such as basilar membrane and organ of Corti, thereby minimizing the risk of trauma on the undamaged structure such as at the apical cochlea. This can ultimately better preserve patient residual natural hearing. Compared to manual insertion and steering of a cochlear implant, the robotically assisted cochlear implantation can allow more people with disabling hearing loss to hear better over their lifetimes.

The present systems and apparatus can improve the use of implants with different shapes or profiles. For example, some cochlear implants (and electrode arrays thereof) can have a curved section to allow the implant to better follow a patient cochlea path to more effectively reduce insertion trauma to the surrounding tissue or the implant, and to bring electrode contacts closer to target stimulation nerve. According to various embodiments discussed in this document, the present systems and apparatus include a modular robotic drive head that features to improve use with electrodes or elongate members that are housed in a sheath or off a stylet and into the cochlea or target site, such that a sheath cover or stylet can be robotically controlled by the drive head as desired for increased precision and decreased insertion trauma to surrounding tissue.

The modular design of the robotically assisted implantation system, as discussed in this document, allows for easy replacement or interchange of a particular module. This can not only improve the system reusability and efficiency, but can also reduce the cost of system maintenance. For example, the external positioning unit can be a single-use device positioned in a sterile surgical field or in contact with the patient during an implantation surgery, and is disposable after surgery. The computerized control unit can be positioned in a non-sterile field, such as a control room, and can be reused with interchangeable external positioning units.

The external positioning unit is a non-implanted external device. Compared to a partially or completely implantable insertion device, the external positioning unit discussed herein can substantially reduce the risk of complications associated with surgical implantation, extraction, or replacement of otherwise partially or completely implantable insertion device. The external positioning unit also has the advantage of easy trouble-shooting, maintenance, and replacement, thereby reducing cost of the system and the procedure. As to be discussed in the following, the external positioning unit can have a small size with limited mechanical and electrical parts, thus making it flexible for external fixation to a patient.

Although the discussion in this document focuses on cochlear implant, this is meant only by way of example and not limitation. It is within the contemplation of the present inventors, and within the scope of this document, that the systems, devices, and methods discussed herein can be configured for robotically delivering, steering, positioning, or extracting various types of implants or prosthesis. By way of non-limiting examples, the implants can include leads, catheter, guidewire, or other mechanical or electrical devices. The implants can be designed for temporary or permanent implantation. The implants can be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. In addition to new implantation, the systems, devices, and methods discussed herein can also be used to surgically reposition or replace an existing implant.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 5 illustrates, by way of example and not limitation, a method for delivering and positioning an implant into a target implantation site of a patient.

DETAILED DESCRIPTION

In the following detailed description, reference is made to the accompanying drawings which form a part hereof, and in which is shown by way of illustration specific embodiments in which the invention can be practiced. These embodiments are described in sufficient detail to enable those skilled in the art to practice the invention, and it is to be understood that the embodiments can be combined, or that other embodiments can be utilized and that structural, logical and electrical changes can be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Disclosed herein are systems, devices, and methods for robotically assisted implantation of an implant in a patient. Examples of the implants can include leads, catheter, guidewire, guide sheath, or other mechanical or electrical devices. The implants can be designed for temporary or permanent implantation. The implants can additionally be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. The present system can be implemented using a combination of hardware and software designed to provide precise control of implant movement, such as insertion of a cochlear implant during a hearing-preservation cochlear implant surgery, or positioning or manipulation of a cochlear implant in a thyroplasty surgery. The system includes an implant-positioning unit a control console communicatively coupled to the implant-positioning unit. The implant-positioning unit includes a drive head configured to engage an elongate member of the implant and robotically deliver and position the implant into a target implantation site. The control console can have a user interface that enables a user to input motion control instructions. The control console can generate a motion control signal, according to a specific motion control instruction, to control the external positioning unit to propel the implant into a target implant site.

Figure 1:
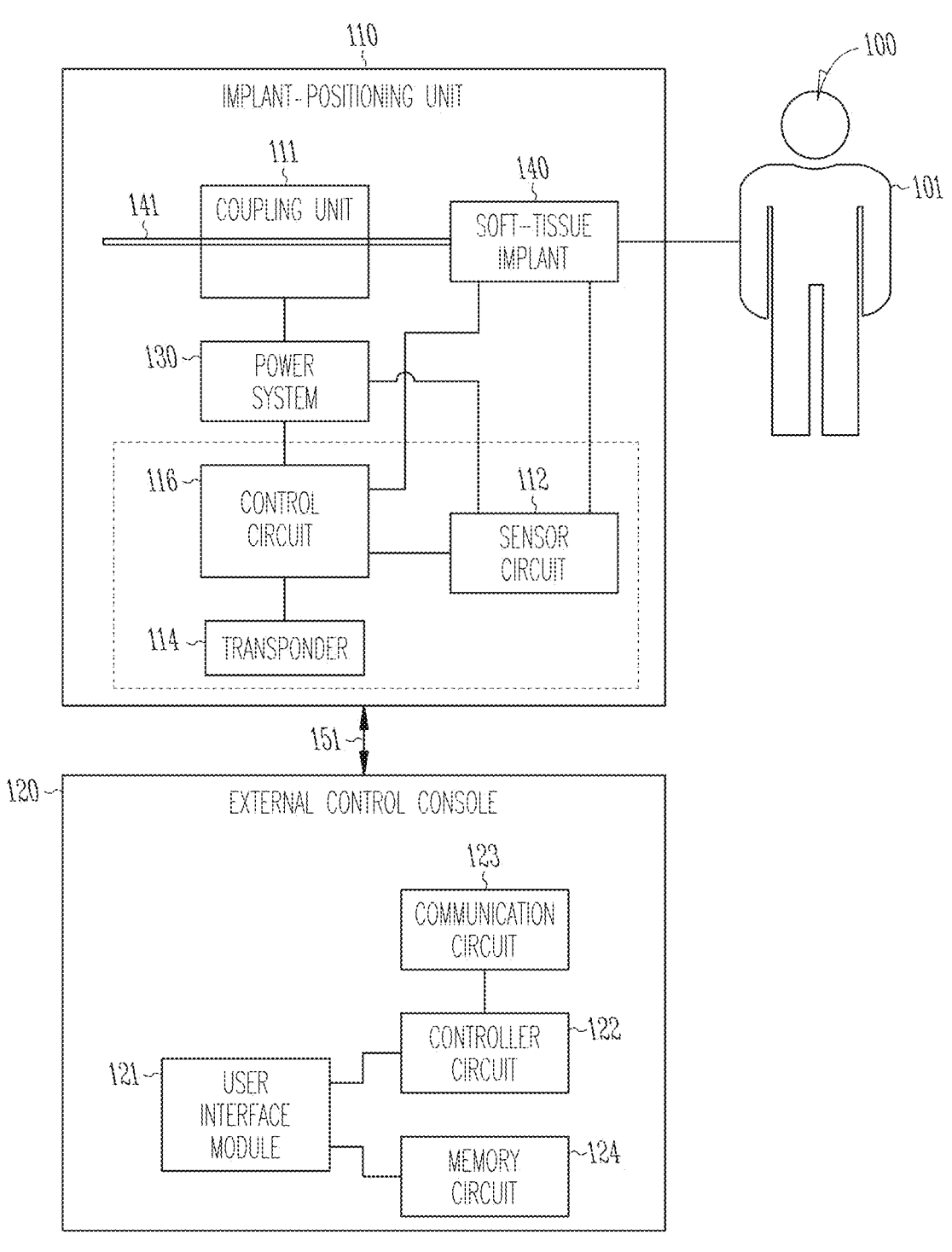
FIG. 1 illustrates, by way of example and not limitation, a robotically assisted implantation system and portions of an environment in which the robotically assisted implantation system can operate.

FIG. 1 is a diagram illustrating, by way of example and not limitation, a robotically assisted implantation system 100 and portions of an environment in which the system 100 can operate. The robotically assisted implantation system 100 can engage an implant 140, and robotically deliver and position the implant 140 into a target implantation site of a patient 101.

The system 100 can include an implant-positioning unit 110 and an external control console 120. The implant-positioning unit 110 can be an external device, or a completely or partially implantable device. The implant-positioning unit 110 can include one or more of a coupling unit 111, a sensor circuit 112, a power system 130, a transponder 114, and a control circuit 116. The coupling unit 111 can interface with an elongate member 141. An implant 140 can be coupled to the elongate member 141 such as on a distal end thereof. The coupling unit 111 includes actuating members arranged to engage at least a portion of the elongate member 141, and robotically propel the elongate member 141 to move the implant 140 into a target site of a patient 101. Examples of the actuating members can include motorized actuation via rollers, screws, gears, or rack-pinion, among others. In an example, the elongate member 141 can be an integral part of the implant 140, such as a tubular implant body or an elongate or telescoping shaft. Examples of such an implant can include an implantable lead or catheter. Alternatively, the elongate member 141 can be a part of a delivery system detachably coupled to the implant 140. Examples of such an implant can include a guidewire or an introducer that can snatch an implant at a particular location, such as at a distal portion of the elongate member 141.

The coupling unit 111 can frictionally move the elongate member 141 to a specific direction (e.g., forward for implant insertion, or reverse for implant extraction), at a specific rate, or for a specific distance relative to a reference point such as the interface between the coupling unit 111 and the elongate member 141. Examples of the coupling unit 111 can include a leadscrew, a clamp, a set of rotors, or a rack and pinion arrangement, among other coupling mechanisms. The coupling unit 111 can compress against at least a portion of the elongate member 141 to produce sufficient friction between the coupling unit 111 and the elongate member 141. In some examples, the coupling unit 111 can include adjustable couplers for reversible or interchangeable connection between the implant-positioning unit 110 and the elongate member 141. In the event of implant exchange or replacement, the coupling unit 111 can operatively release the compression on the elongate member 141, which can be then removed from the implant-positioning unit 110. A new implant with an elongate member can be reloaded and engaged into the implant-positioning unit 110. The implant-positioning unit 110 need not be removed and can remain in place during implant replacement.

In some examples, the implant 140 can be delivered through a guide sheath. In some examples, the implant-positioning unit 110 includes separate structures to control a guide sheath separately from the implant 140. In other examples, the guide sheath can be positioned initially by the implant-positioning unit 110, and the implant 140 implanted through the previously positioned guide sheath.

In an example, the implant 140 can be a cochlear implant for treating hearing loss through electrostimulation of a specified cochlea region. The cochlear implant can include an implantable stimulator that can be implanted under the scalp, can generate electrical impulses, and deliver the electrical impulses to the electrode array through conductors in the elongate member 141. The electrode array can be surgically inserted into and positioned at the target cochlear site. In patients with impaired high-frequency hearing function but preserved low-frequency hearing function, a short electrode array of the implant can be positioned at the outer or basal cochlear region to deliver electrostimulation therein to restore high-frequency hearing function. The implant-positioning unit 110 can be a compact, lightweight micro-mechanical device suitable for direct attachment to the patient, such as on the patient head during a cochlear implant surgery, while maintaining sufficient stability during the implantation. The implant-positioning unit 110 can be sized and shaped to facilitate patient attachment. In an example, the implant-positioning unit 110 can have a curved exterior contact surface that conforms to the contour of a body part of the patient 101, such as a head region.

In another example, the implant 140 can be a thyroplasty implant. When delivered and positioned at a target site, the implant 140 interfaces with target soft tissue. The implant-positioning unit 110 can manipulate the implant 140 to alter the position or the shape of at least a portion of the target soft tissue. In an example, the implant 140 can include a soft-tissue prosthesis made of biocompatible material, such as Silastic, Gore-Tex, silicon, hydroxyapatite, titanium, or polymer, among other permanent or resorbable materials. In an example, the implant-positioning unit 110 can be used in a phonosurgery (surgery on the voice box) to address various voice, swallowing, and breathing disorders. A surgeon can robotically control the implant-positioning unit 110, via the external control console 120 and wireless transponder, to position a thyroplasty implant inside patient voice box to interface with a vocal cord, and manipulating the thyroplasty implant to alter the position and shape of the vocal cord to restore or improve voice.

Once the implant 140 has been positioned at the target site, the elongate member 141 can be disengaged from the implant 140. Alternatively, the elongate member 141 can remain attached to the implant 140 following the implantation. This allows a surgeon to re-optimize implant position in an implant revision procedure following the initial implantation without the need of a surgery to reattach the implant 140 to the elongate member 141.

The power system 130 is configured to provide driving force to the coupling unit 111. The power system 130 includes a motor that can generate driving force and motion, and a power transmission unit to transmit the driving force and motion to the coupling unit 111 to actuate the motion of the elongate member 141. Examples of the motor can include stepper motors (e.g., micro- or nano-stepper motors), direct current (DC) motors, pneumatic or piezo-electric motors, ultrasonic motors, or linear motors, among others. The motor can be electrically coupled to a power source. In an example, the power source can include a rechargeable power source, such as a rechargeable battery or a supercapacitor. The rechargeable power source can be charged wirelessly by a portable device such as a handheld device with circuitry configured to transfer energy to the rechargeable power source through electromagnetic induction or other transcutaneous powering means.

In the example as illustrated in FIG. 1, the power system 130 is at least partially included in or associated with the implant-positioning unit 110. Alternatively, the power system 130 can be at least partially included in or associated with the external control console 120. In another example, the power system 130 can be separated from the implant-positioning unit 110 and the external control console 120, and coupled to the coupling unit 111 via a connection. The connection can be a part of the transmission unit.

The control circuit 116 can be coupled to the transponder 114 to receive a motion control signal from the external control console 120. In an example, the coupling between the control circuit 116 and the transponder 114 is a wireless coupling. The motion control signal can specify values for various implant motion parameters, and can be generated according to user programming instructions such as provided via the user interface module 121. The control circuit 116 can control the motor to generate driving force and motion according to the received motion control signal, and drive motion of the elongate member 141 via the power transmission unit and the coupling unit 111. Examples of the power transmission unit can include chains, spur gears, helical gears, planetary gears or gearhead, worm gears, miniature pulleys, shaft couplings, or timing belts, among others. The power transmission unit can adjust the speed or torque output from the motor, and to deliver specific output to the coupling unit 111.

In various examples, the power system 130 can include two or more motors coupled to respective power transmission units, and the power transmission units are coupled to respective coupling units that engage the same elongate member 141 at different locations thereof. The two or more motors can be of the same or different types. The transponder 114 can receive from the external control console 120 a motion control signal for controlling each of the two or more motors. In an example, a user can program and control each of the motors independently, such as via the user interface module 121. The motion control signal specifies the configuration of, and input voltage or current to, each of the motors. According to the motion control signal, the control circuit 116 can control the two or more motors to generate respective torque, speed, or rotation direction. Through the elongate member 141, the implant-positioning unit 110 can operatively move the implant 140 in multiple axis and planes with up to six degrees of freedom (medial, lateral, superior, inferior, anterior, and posterior). In an example, a first motor produces a translational motion of the elongate member 141, and second motor can produce a rotational motion of the elongate member 141. The control circuit 116 controls various translational motion parameters (e.g., translational rate, direction (advancement or withdrawal), distance relative to a reference point, a position of a distal end of the elongate member 141, an amount of axial force applied to the elongate member 141), and rotational motion parameters (e.g., angular position, angular displacement, angular velocity, or an amount of lateral or rotational force applied to the elongate member 141).

In some examples, the implant 140 can be attached to two or more elongate members each representing an embodiment of the elongate member 141. Each elongate member can be coupled to a respective coupling unit representing an embodiment of the coupling unit 111. The transponder 114 can receive from the external control console 120 a motion control signal for controlling each of the two or more motors. According to the motion control signal, the control circuit 116 can control the two or more motors to generate driving forces to independently move the respective elongate members in different direction (e.g., advancement or withdrawal) or at different rate. Through independent control of multiple elongate members, the implant-positioning unit 110 can operatively move the implant 140 in multiple axis and planes. For example, the implant 140 can not only be advanced or withdrawn translationally, but can slant or rotate at different angles, thereby manipulating the target soft tissue at a desired position or with a desired shape.

In various examples, the control circuit 116 can change the shape or physical dimension of at least a portion of the implant 140, such as topography of an implant surface interfacing with the target soft-tissue. The implant 140 can include an array of micro-actuators on the tissue-interfacing surface of the implant. In response to an implant contour control signal from the external control console 120, the control circuit 116 can activate the micro-actuators to change tissue-contacting surface contour. The change in the implant shape can result in changes in position or shape of at least a portion of the soft tissue. Compared to the motion control of the implant 140 via the power system 130 and the elongate member 141 for "macro position adjustment" of the target soft tissue, the surface contour control of the implant 140 via the micro-actuators can be used for "micro position adjustment" of the target soft tissue.

The sensor circuit 112 can be configured to sense information about position or motion of the implant during implantation. The sensor circuit 112 can be attached to the motor or the power transmission unit within the power system 130, or associated with the coupling unit 111, to detection information about position of the implant. Examples of the sensor circuit 112 can include a Hall-effect sensor integrated in the motor, one or more optical sensors attached to the coupling unit, a capacitive sensor configured to detect implant motion. The sensor circuit 112 can include force sensors included in the power system 130 or the coupling unit 111, or associated with the implant 140, to sense a parameter indicative of force or friction imposed on the implant during the implant advancement, such as axial, lateral, or radial forces when the implant 140 interacts with the target soft-tissue. Examples of the force sensors can include resistors, capacitive sensors, piezoelectric material, or a strain gauge, among others. In an example, the force can be indirectly sensed by measuring the current supplied to the motor.

The current measurement can be transmitted to the external control console 120, where it is converted to the force (or torque) using the torque-current curve predetermined and stored in the memory circuit 124. In some examples, the sensor circuit 112 can include sensors on the implant 140 to provide information indicative of shape or contour of the tissue-contacting surface of the implant 140, such as before and after applying voltage to the micro-actuators on the tissue-contacting surface of the implant.

The information acquired by the sensor circuit 112 can be forwarded to the external control console 120 via the communication link 151. The sensor information can be displayed or otherwise presented in a specific media format in the output module 126. In an example, the implant-positioning unit 110 can include an indicator to produce a visual or audio notification in response to the sensed sensor signal satisfies a specific condition. The indicator 213 can include, for example, a light emitting diode (LED) that can be turned on when the sensed sensor signal indicates the implant reaches the target site. In some examples, the indicator can include a plurality of LEDs with different colors or different pre-determined blinking patterns. The LED colors or the blinking patterns can correspond to various events encountered during the implantation procedure.

In some examples, the implant-positioning unit 110 can be configured for subcutaneous implantation. An implantable position device such as the implant-positioning unit 110 is advantageous in certain applications such as thyroplasty surgery, which can have a high revision rate following the initial implantation. The implant-positioning unit 110 allows a surgeon to remotely adjust the position of the pre-implanted thyroplasty implant, without the need of surgical intervention, to re-optimize patient vocal quality when the implant status or patient condition changes following the initial implantation. In an example, electrical and mechanical components of the implant-positioning unit 110 can enclosed in a housing that can be anchored to an anatomical structure neighboring the target soft tissue. In another example, the components of the implant-positioning unit 110 can be packaged into separate housings that can be implanted at different body locations. For example, the power system 130 and the coupling unit 111 can be enclosed in a first housing to be anchored to thyroid cartilage of the voice box neighboring the vocal cord, while the control circuit 116, the sensor circuit 112, and the transponder 114 can be assembled on a circuit board enclosed in a second housing subcutaneously implanted at a body location away from the vocal box, such as under the skin on the neck or chest.

The implant-positioning unit 110 can include a fixation member to allow for detachable affixation of the implant-positioning unit 110 to the anchoring structure. The fixation can be invasive fixation that involves incision and/or penetration of the anchoring structure or the subcutaneous tissue. Examples of the fixation member can include one or more of a screw, a pin, a nail, a wire, a hook, a barb, a helix, a suture, a glue, or a magnet within the implant-positioning unit 110 coupled to one or more magnetic screws or pins affixed to the body part of the patient 101. In an example, the fixation member can include one or more of self-drilling screws, self-tapping screws, or self-piercing screws, such that no pilot hole needs to be drilled at the affixation site prior to screw installation.

In some examples, while some portion of the implant-positioning unit 110 is implantable, at least a portion of the implant-positioning unit 110 can be externally positioned, such as a portion of the power system 130 (e.g., power source, or motor), the sensor circuit 112, or the transponder 114, among others. The non-implantable components can be packaged and affixed to the skin of a body part using non-invasive fixation means, such as clamps, temporary glues, or other holding devices that prevent lateral motion relative to the patient 101. The external package can be a compact and lightweight for direct attachment to the patient, while maintaining sufficient stability during the implantation. The external package can be sized and shaped to facilitate patient attachment, such as having a curved exterior surface that conforms to the contour of a body part of the patient 101.

The contact surface of the implant-positioning unit 110 can be processed to improve stability during the implant advancement procedure. In an example, the implant-positioning unit 110 can have an exterior surface with a rough finish, such as ridges, corrugates, teeth, or other coarse surface textures. Additionally or alternatively, the implant-positioning unit 110 can have one or more gripping elements configured to frictionally bond the implant-positioning unit 110 to a body part of the patient 101, such as the anchoring structure for subcutaneous implantation or epicutaneous placement. The gripping elements can be distributed on a portion of the exterior surface. Examples of the gripping elements can include penetrators such as spikes, pins, or barbs protruding from the exterior surface. When the implant-positioning unit 110 is pressed and held against the attachment region, the rough surface or the gripping elements can provide sufficient friction or gripping force to securely hold the implant-positioning unit 110 in place relative to the patient 101 during the implantation advancement.

The external control console 120 can include a dedicated hardware/software system such as a programmer, a remote server-based patient management system, or alternatively a system defined predominantly by a controller software running on a standard personal computer. The external control console 120 can robotically control the coupling unit 111 to propel the elongate member 141 at specific rate, to a specific direction, for a specific distance, or at a specific maximum force, thereby positioning the implant 140 at the target site of the patient 101. The external control console 120 can additionally receive information acquired by the sensor circuit 112. The external control console 120 can also receive measurement data from external systems that can be directly related to implant position. The external control console 120 can utilize such measurement data (e.g., physiological measurements) for closed-loop control of implant positioning and manipulation. For example, the external control console 120 can receive patient voice input via the user interface module 121 as feedback to manipulate the implant 140. In various examples, the external control console 120 can include a physiologic sensor configured to sense a physiologic signal, such as respiration or muscular movement of the patient. The controller circuit 122 can determine dynamic motion control feedback, and control the positioning and manipulation of the implant further using the sensed physiologic signal.

The external control console 120 can include a user interface module 121 and a controller circuit 122. The user interface module 121 can include a user input module and an output module. The user input module can be coupled to one or more input devices such as a keyboard, on-screen keyboard, mouse, trackball, touchpad, touch-screen, or other pointing or navigating devices. In some example, the user input module can be incorporated in a mobile device communicatively coupled to the external control console 120, such as a handheld device. The user input module can be configured to receive motion control instructions from a user. The motion control instructions can include one or more target motion parameters characterizing desired movement of the elongate member 141 of the implant. For example, the target motion parameters can define maximum values or value ranges of the motion parameters. Examples of the target motion parameters can include a target movement rate, a target movement direction or orientation, a target movement distance, a target position of a distal end of the elongate member, or a target amount of force imposed on the elongate member 141. The movement of the implant can be activated at intervals of a predetermined step size. In an example of implantation of a cochlear implant, the target movement rate is approximately at 100-micron intervals. In an example, the target movement distance is approximately 1-35 millimeters. In an example of implantation of a thyro-plasty implant, the target movement distance can range from 0.1-20 millimeter (mm). The target movement rate is approximately at 100-micron intervals. The motion control instructions can include a pre-determined implant delivery protocol that defines target values of a plurality of motion parameters. The implant delivery protocols are designed to ease the programming of the motion control, and to mini-mize peri-surgical tissue trauma or damage to the implant or damage to the surrounding tissue.

The user interface module 121 can allow a user to select from a menu of multiple implant delivery protocols, cus-tomize an existing implant delivery protocol, adjust one or more motion parameters, or switch to a different implant delivery protocol during the implant delivery procedure. The external control console 120 can include a memory circuit 124 for storing, among other things, motion control instruc-tions. In an example, one of the delivery protocols can include use of intraoperative physiologic measures that can reflect immediate changes in soft-tissue mechanics and insertion trauma pre-, during-, and post-insertion of the implant 140. In an example of implantation or revision of a thyroplasty implant, the delivery protocols can include use of intraoperative patient voice feedback.

The output module can generate a human-perceptible presentation of information about the implant delivery con-trol, including the programmable motion control parameters, and the motion control instructions provided by the user. The presentation can include audio, visual, or other human-perceptible media formats, or a combination of different media formats. The output module 126 can include a display screen for displaying the information, or a printer for print-ing hard copies of the information. The information can be displayed in a table, a chart, a diagram, or any other types of textual, tabular, or graphical presentation formats. Addi-tionally or alternatively, the output module 126 can include an audio indicator such as in a form of beeps, alarms, simulated voice, or other sounds indicator.

The output module 126 can also generate presentation of data sensed by the sensor circuit 112, including data such as current position and movement rate of the implant, the force or friction applied to the implant motion. This allows a surgeon to monitor in real-time the progress of the implan-tation, and adjust the motion control as needed. The presen-tation can include real-time visual or audible notification with specified patterns corresponding to different types of events encountered during implantation. In an example, the output module 126 can include a visual indicator, such as a light emitting diode (LED) or an on-screen indicator on the display screen. A specific LED color or a specific blinking pattern can signal to the user a successful positioning of the implant at the target site. A different LED color or a different blinking pattern can alert an excessive force imposed on the implant due to unintended tissue resistance during the implant advancement. The output module 126 can addition-ally or alternatively include an audio indicator, such as a beep with a specific tone, a specific frequency, or a specific pattern (e.g., continuous, intermittent, pulsed, sweep-up, or sweep-down sound). In an example, a beep or an alarm with a specific tone or pattern can signal to the user successful positioning of the implant at the target site. A beep or an alarm with a different tone or different pattern can alert an excessive force imposed on the implant. In an example, the beep or the alarm can go off continuously as the sensor senses the implant approaching the target site. The sound frequency or the pulse rate of the beep or the alarm can increase as the implant gets closer and finally reaches the target site. In an example, the frequency of the beep or the alarm can correspond to a rate of motion, such as sounding for every one millimeter of motion. Audible feedback on the motion parameters can be advantageous in that the surgeon can be notified in real time the implantation status or events encountered without the need to look away from surgical field. This can assist surgeon with enhanced surgical preci-sion and patient safety. In some examples, the audible or visual sensor feedback can signal to the user that the sensed implant position, motion, or for has exceeded the pro-grammed target or maximum parameter values.

The controller circuit 122 can be configured to generate an implant motion control signal and/or an implant contour control signal for controlling the implant-positioning unit 110 to deliver, position, and manipulate the implant 140. Such control signals can be generated according to the motion control instructions provided by the user via the user input module 125. In accordance with the motion control signal, the control circuit 116 can control the power system 130 to regulate one or more motion parameters of the elongate member 141, such as a movement rate, a movement direction or orientation, a movement distance, a position of a distal end of the elongate member, or an amount of force imposed on the elongate member 141, among others. In some examples, the controller circuit 122 can generate multiple motion control signals that can be used to respec-tively control multiple motors configured to drive different modes of motion (e.g., translational or rotational motions) on the same elongate member 141, or to drive different elongate members, as discussed above. In some examples, the controller circuit 122 can control the motion of the elongate member 141 further according to information about patient medical history or disease state received via the user input module 125, or stored in the memory circuit 124. In an example of cochlear implant, information about patient tonotopic hearing loss pattern. The tonotopic hearing loss pattern represents a spatial distribution of frequency sensi-tivity along the axis of the cochlea length. Based on the input of the patient tonotopic hearing loss pattern, the controller circuit 122 can automatically program one or more motion parameters, such as the electrode array insertion distance. In accordance with the motion control signal, the control circuit 116 can activate an array of micro-actuators such as by applying a voltage map to change tissue-contacting surface contour, thereby causing changes in shape or posi-tion of the target soft tissue.

The controller circuit 122 can remotely control the implant-positioning unit 110 via a communication circuit 123. The communication circuit 123 can transmit the motion control signal to the power system 130 via the communica-tion link 151. The communication link 151 can include a wired connection including universal serial bus (USB) con-nection, or otherwise cables connecting the communication interfaces on the external control console 120 and the power system 130. The communication link 151 can alternatively include a wireless connection, such as a Bluetooth protocol, a Bluetooth low energy protocol, a near-field communica-tion (NFC) protocol, Ethernet, IEEE 802.11 wireless, an inductive telemetry link, or a radio-frequency telemetry link, among others.

In various examples, the implant-positioning unit 110 can include a manual control mechanism in addition to the robotic control of the coupling unit 111. The manual control mechanism can bypass or override the robotic motion con-trol of the implant 140. Examples of the manual control mechanism can include a dial turn, a screw, or direct insertion technique. The output module 126 can enable a user to selectably enable a robotic mode for robotically assisted motion control via the power system 130, or a manual override mode for manual motion control of the elongate member 141. Alternatively, an operation on the manual control mechanism can automatically withhold or disable the robotic motion control of the elongate member 141.

Portions of the external control console 120 can be implemented using hardware, software, firmware, or combinations thereof. Portions of the external control console 120 can be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

FIGS. 2A-2D illustrate, by way of example and not limitation, diagrams of different views of an implant-positioning unit 200 for engaging an elongate member, such as the elongate member 141. The implant-positioning unit 200 is an embodiment of at least a portion of the implant-positioning unit 110, and can be configured to robotically deliver and position an implant (e.g., a cochlear implant or a thyroplasty implant) attached to the elongate member into a target site, or to manipulate soft tissue therein, such as a cochlear or a vocal cord.

Figure 2A:
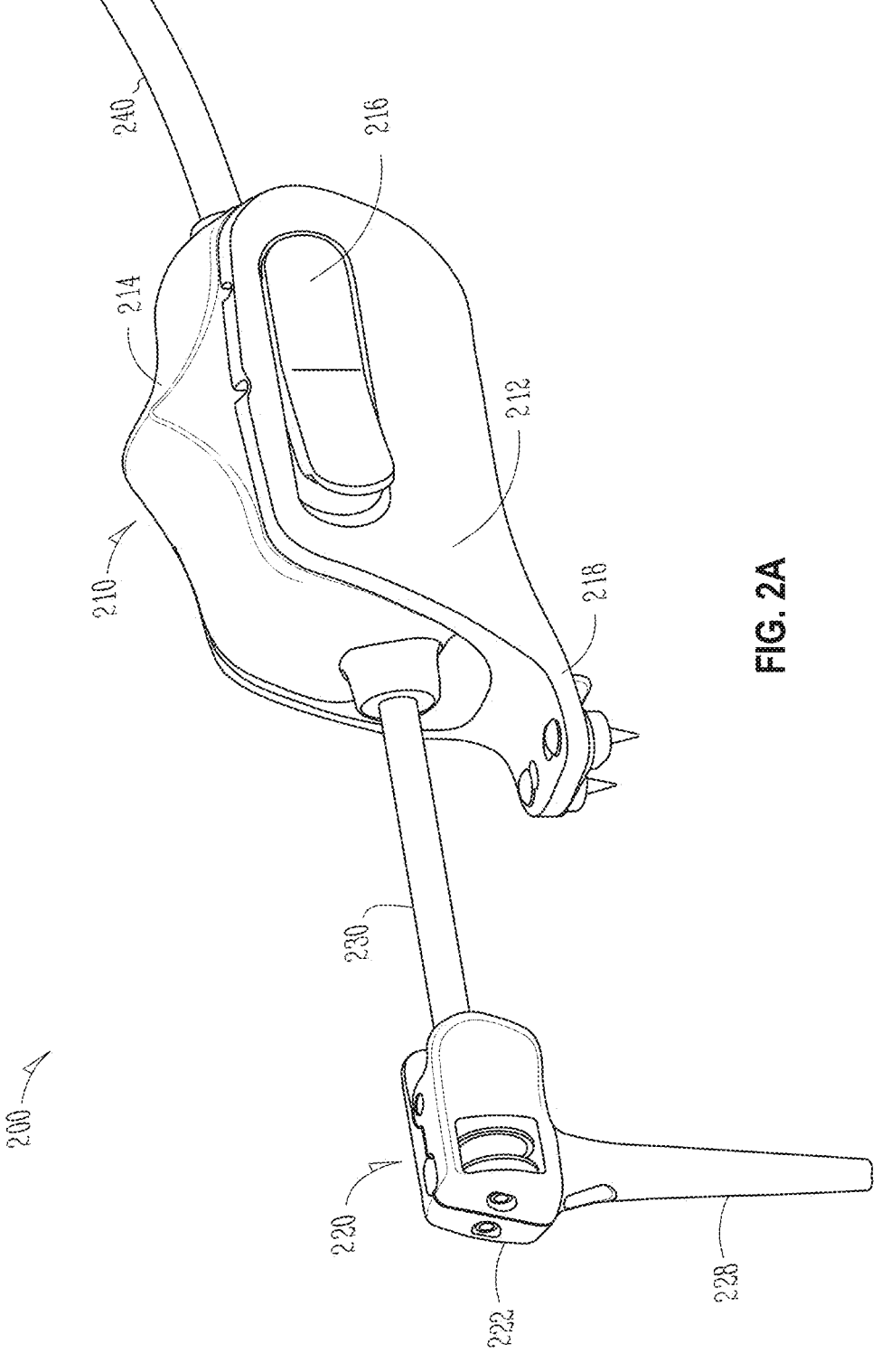
FIGS. 2A-2D illustrate, by way of example and not limitation, different views of an embodiment of an implant-positioning unit for engaging an elongate member of an implant.
Figure 2B:
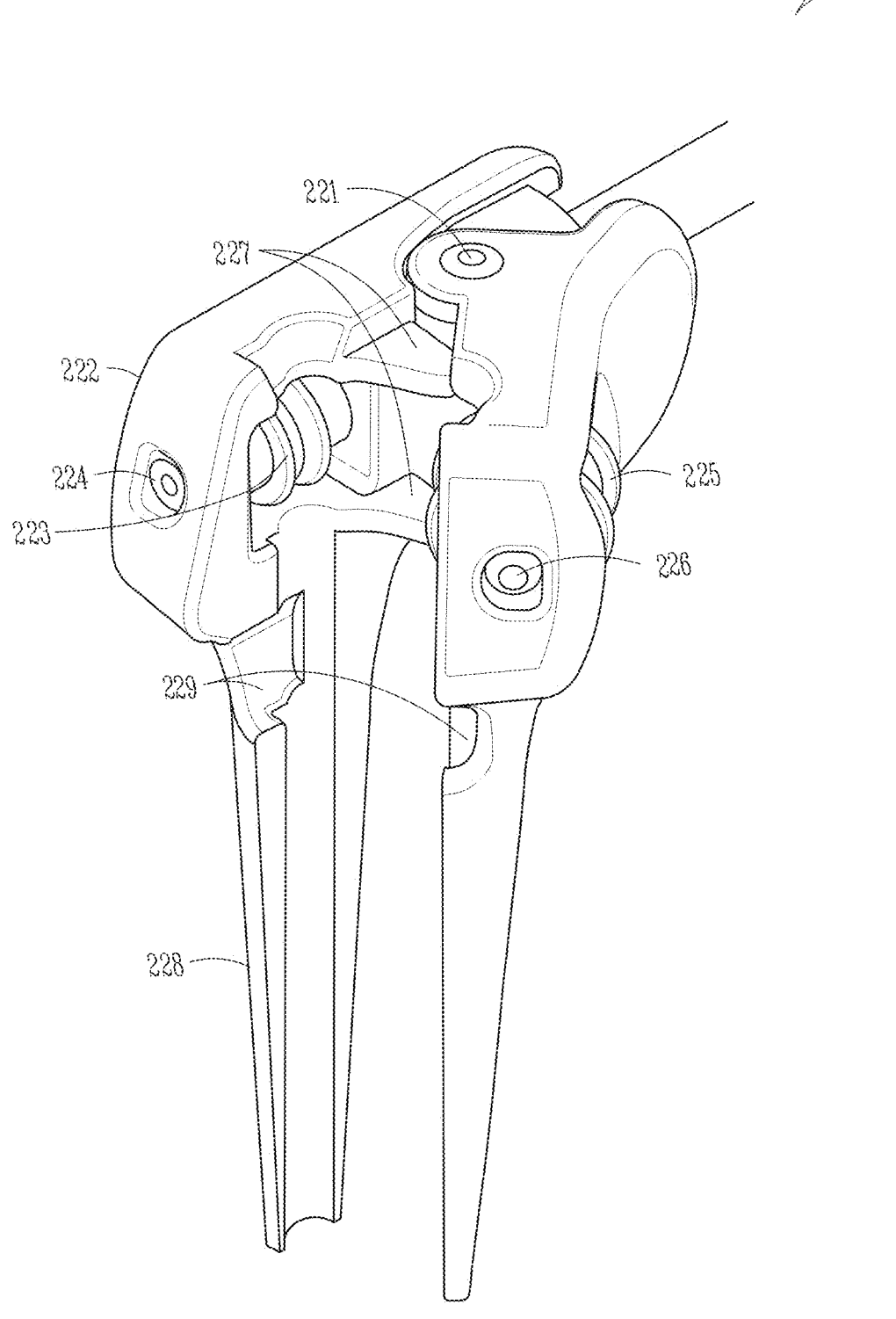
Figure 2C:
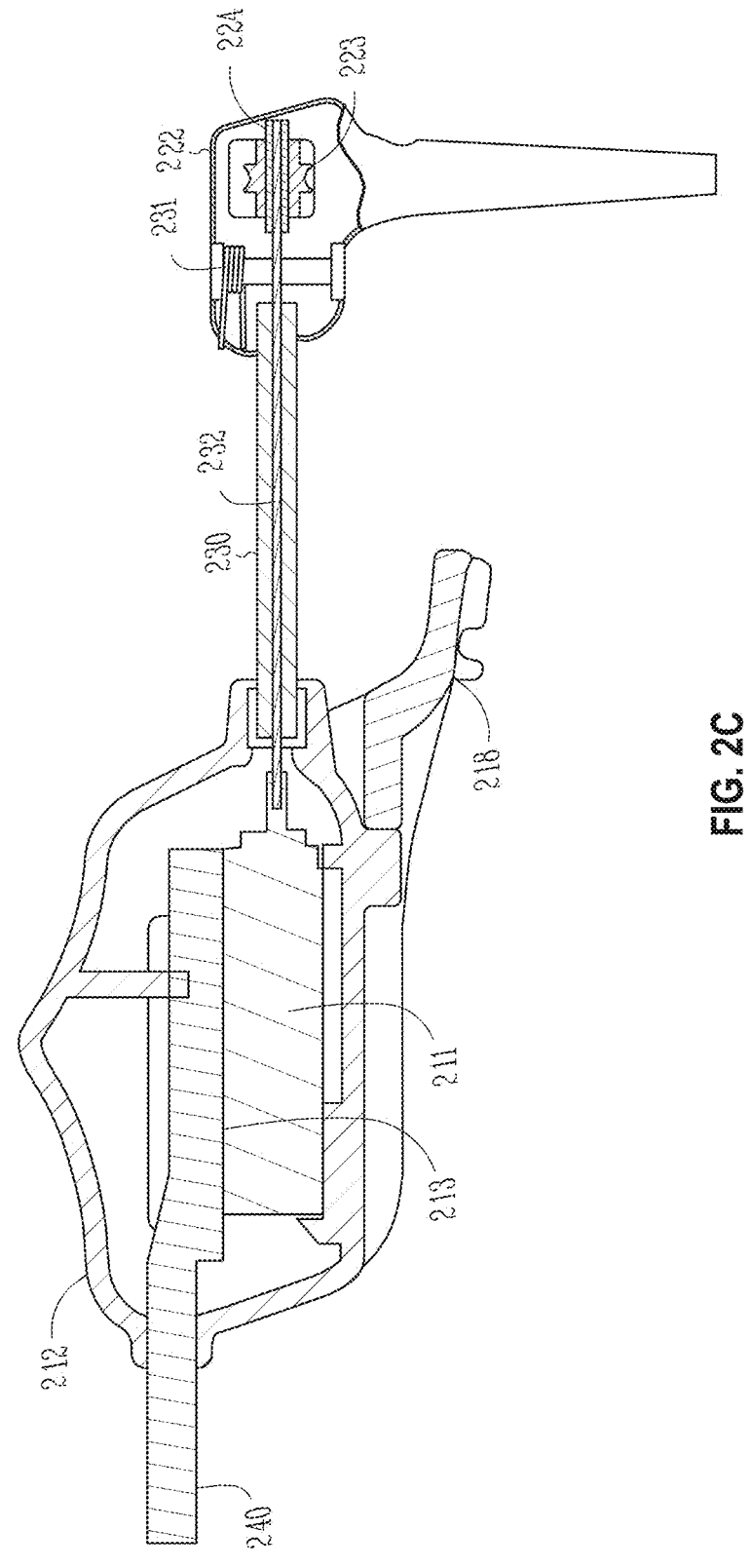
Figure 2D:
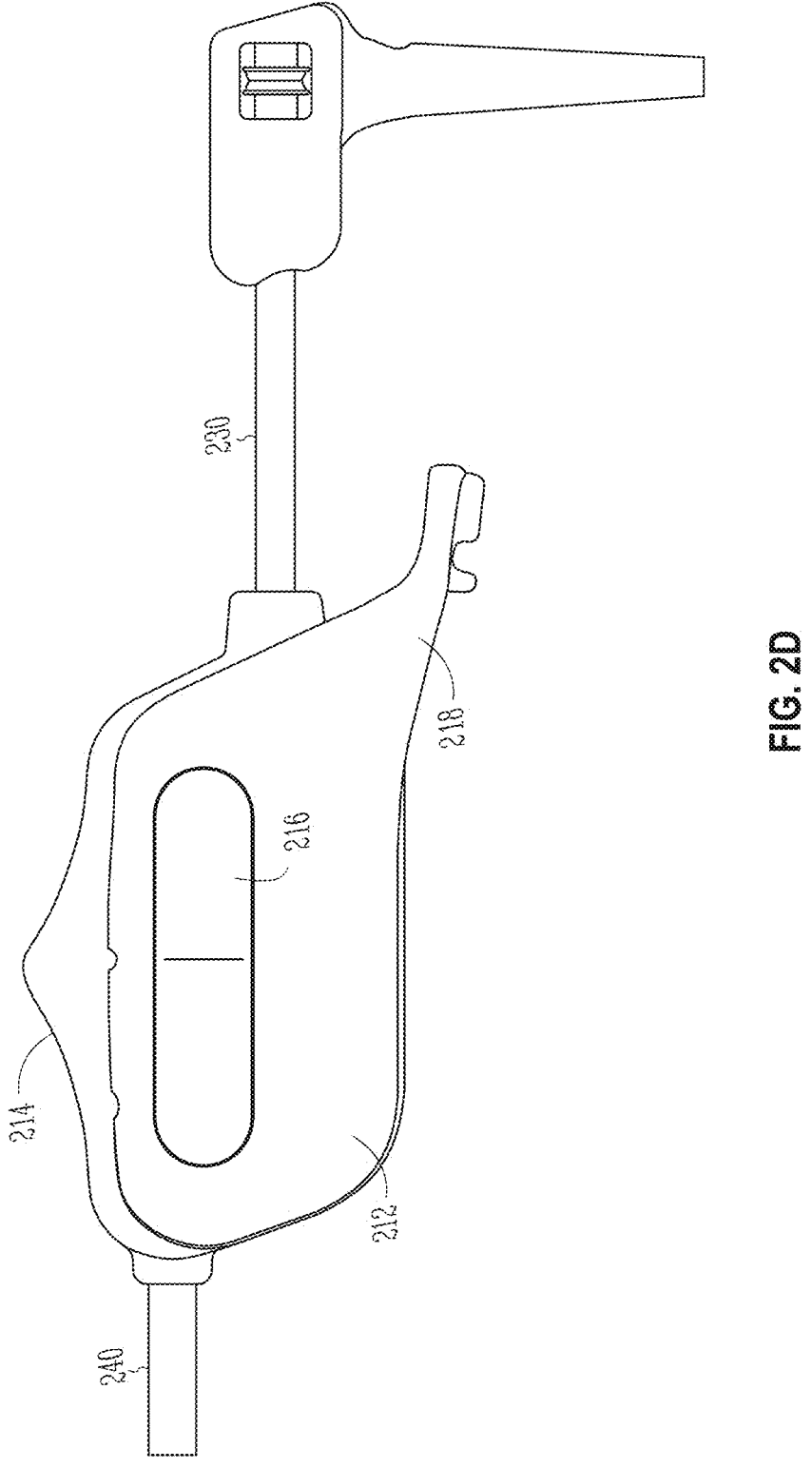

FIG. 2A is an external view of the implant-positioning unit 200. FIGS. 2C and 2D are respectively a cross-section view and a side-view of the implant-positioning unit 200. The implant-positioning unit 200 can include a power system contained in a separate housing than a coupling unit (e.g., wheels including a drive wheel and an idle wheel arrangement) for engaging the elongate member. The power system comprises a motor and motor control circuitry that provide driving force to the coupling unit. As illustrated in FIG. 2A, the implant-positioning unit 200 includes a slidable control box 210 and an implant drive head 220. The slidable control box 210 includes a case 212, a sliding member 214, a case lock 216, and a base mount 218. The sliding member 214 allows for user gripping and sliding the slidable control box 210 linearly for optimal placement of the slidable control box 210 on an anatomical surface (e.g., patient skull). The case lock 216, which can be a toggle switch located on both sides of the case 212, can lock or unlock the slidable control box 210 at a position when pressed. The base mount 218 can be sized and shaped to conform to the anatomical surface, and can include anchoring members (e.g., self-tapping, captive bone screw holes) that secure the slidable control box 210 thereon. In some examples, the base mount 218 can be C-shaped to hold and compress the sliding case 212 therein. This allows linear movement and increased travel range of the slidable control box 210 and drive head 220 for optimal positioning of the drive head 220 and varying anatomical sizes.

As illustrated in FIG. 2C, enclosed within the case 212 includes an electric motor 211 that can generate driving force and motion, and a motor controller 213 (e.g., a printed circuit board) that can generate motion control signal to control movement of the electric motor 211. The electric motor 211 and the motor controller 213 can be respectively connected to a power source and an external control computer via a power/communication cord 240, such as a USB cable.

The implant drive head 220 can be connected to the slidable control box 210 via an adjustable arm 230, such as an adjustable Gooseneck arm. The adjustable arm 230 can be a flexible, semirigid arm that allows for multiple depth-of-field (DOF) adjustment of the drive head 220 at multiple, different angles to the insertion implant site, providing adjustable stability of the drive head 220. In an example, the adjustable arm 230 can be bended to adjust the position of the implant drive head 220. This allows for easy advancement of the elongate member and the associated implant into the target site (e.g., cochlea or vocal cord).

The implant drive head 220 includes a drive housing 222 that can house drive mechanism, an introducer sheath, and sheath components. FIG. 2B illustrates a cutaway view of the implant drive head 220. The drive housing 222 comprises two symmetrical housing halves interconnected via a hinge 221. The hinge 221 allows for opening and closing of the drive housing 222 to engage and disengage with the elongated member or electrode of varying sizes, geometry, and diameter. In some examples, one or more backstops 227 can be included inside the drive housing 222 to prevent the elongate member or the electrode therewith from reaching the hinge 221 during engagement, thereby preventing inadvertent damage to the elongate member or the electrode therewith.

The drive mechanism inside the drive housing 222 can include a drive wheel 223, an idle wheel 225, and a torsion spring 231, which together form an embodiment of the coupling unit 111. The drive wheel 223 rotates to insert or retract elongate member through sheath, and the idle wheel 225 rotates to keep the elongate member aligned with the drive wheel 223. A drive pin 224 can be included to improve smooth rotation of the drive wheel 223, and an idle pin 226 can be included to improve smooth rotation of the idle wheel 225. As illustrated in FIG. 2C, torque can be transmitted from the electric motor 211 to the drive wheel 223 via a torque cable 232, at least a portion of which can be enclosed in the adjustable arm 230. The torsion spring 231 allows the drive head 220 to open and close, and provides compression on the elongate member for frictional motion.

The implant drive head 220 includes a sheath 228 that provides lateral and peripheral support to move the flexible elongate member inside the sheath 228. In an example, a loading access 229, such as a slit or notch, can be included in the sheath 228 for accessing and loading the elongated member into the drive head 220 after the housing halves are closed. The inside of the sheath 228 forms a guide track 250 to accommodate the elongate member. The guide track 250 is connected to an entrance port 251 on the top of the drive head 220, and an exit port 252 at the distal end of the sheath 228. The elongate member can be inserted into the drive head 220 from the entrance port 251, move along the guide track 250 under robotic control, and exit the guide track 250 from the exit port 252. The exit port 252 can be shaped to control final orientation of the implant placement based on the implant geometry.

The guide track 250 can be sized and shaped or otherwise configured to facilitate control and manipulation of the elongate member 141 during the implant procedure, such as for insertion, rotation, or retraction of the elongate member 141. In an example, the guide track 250 can have a groove with a specific depth and shape to accommodate the elongate member 141 and to prevent rotation or twisting of the elongate member 141 while in motion inside the guide track 250.

Figure 3A:
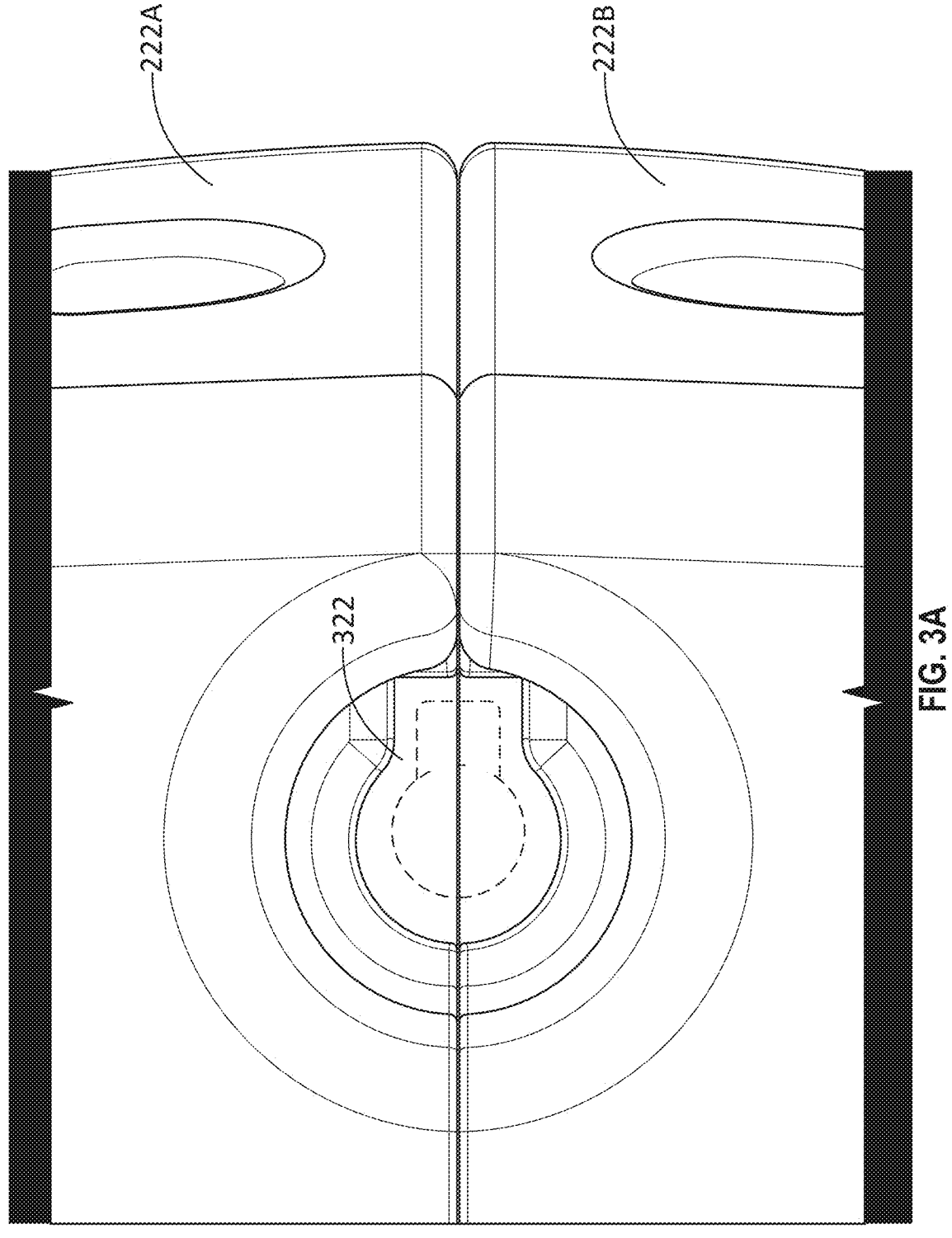
FIGS. 3A-3B are diagrams illustrating, by way of example and not limitation, different views of an implant drive head.
Figure 3B:
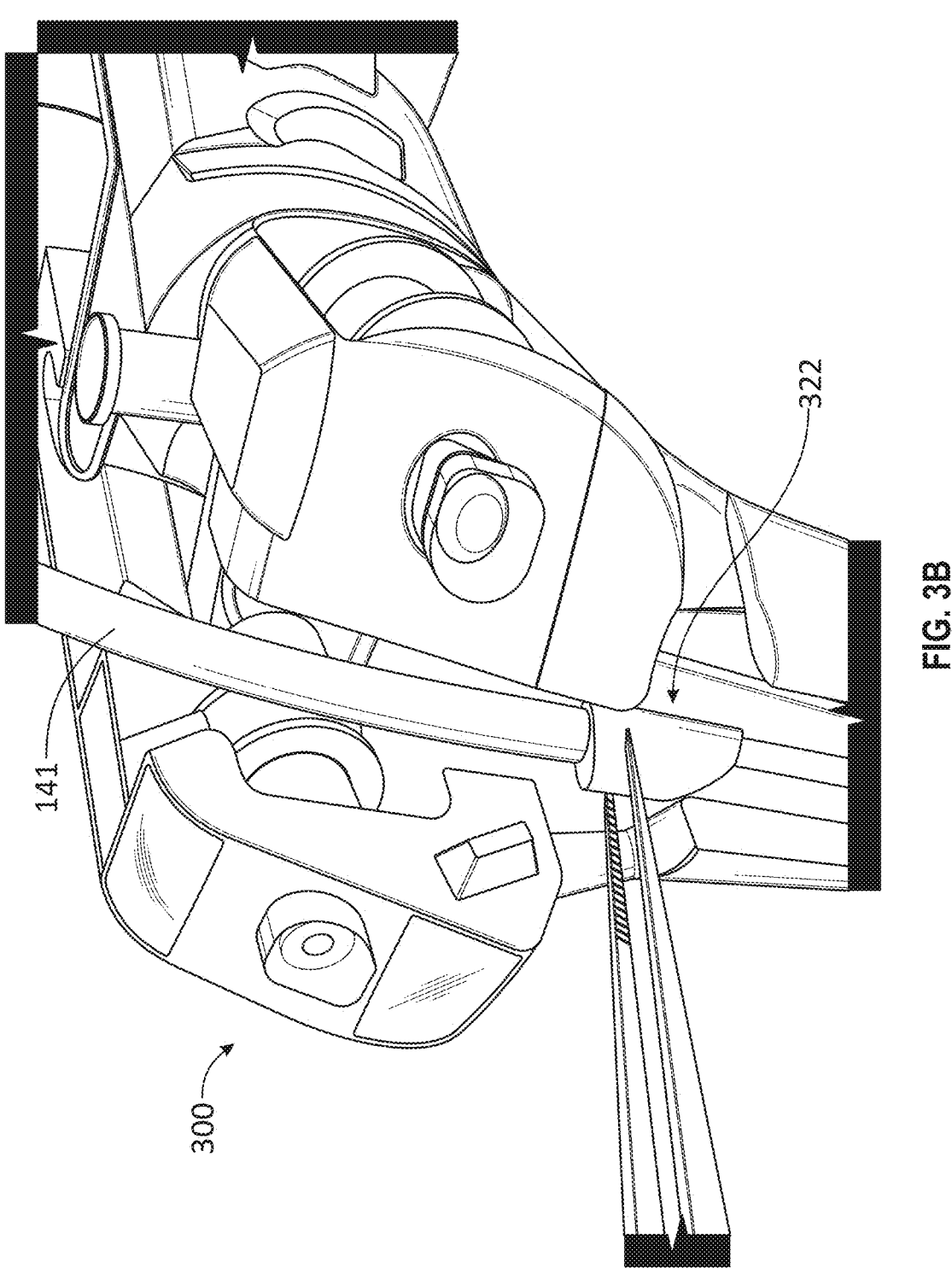

FIGS. 3A-3B are diagrams illustrating by way of example different views of an implant drive head 300, which is an embodiment of the implant drive head 220. FIG. 3A illustrates a top-down view, and FIG. 3B a side view, of the implant drive head 300 that has an implant access port 322 connected to a guide track. The access port 322 is an embodiment of the loading access 229 shown in FIG. 2B. The access port 322 can enable a user (e.g., a surgeon) to access through the elongate member 141 when the housing halves are clamp closed. For example, a user can grasp the elongate with forceps (as shown) through the access port 322 and engage the elongate member 141 to the drive head 220 without the forceps preventing closure of the housing halves. The elongate member 141 can then pass through the guide track 250 of the sheath 228.

Figure 3D:
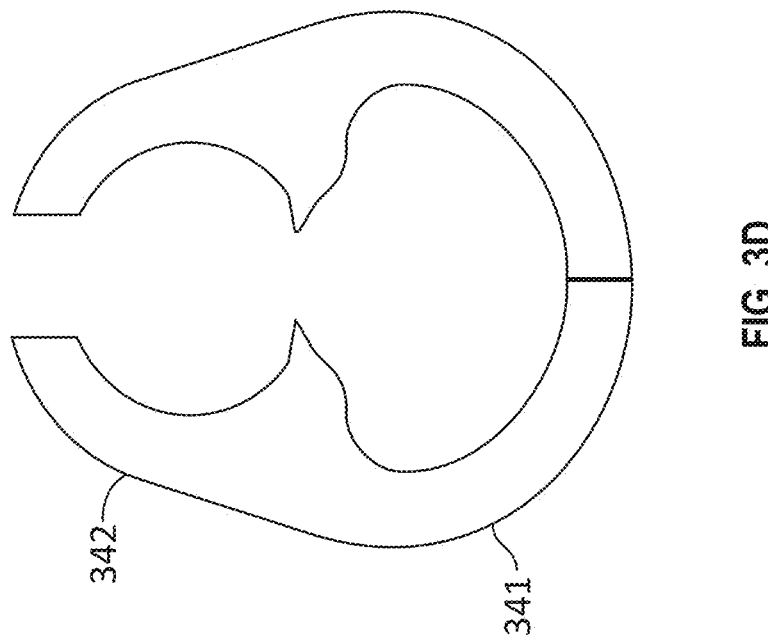
FIG. 3C-3D illustrate, by way of example and not limitation, various shapes of the cross section of the guide track.
Figure 3C:
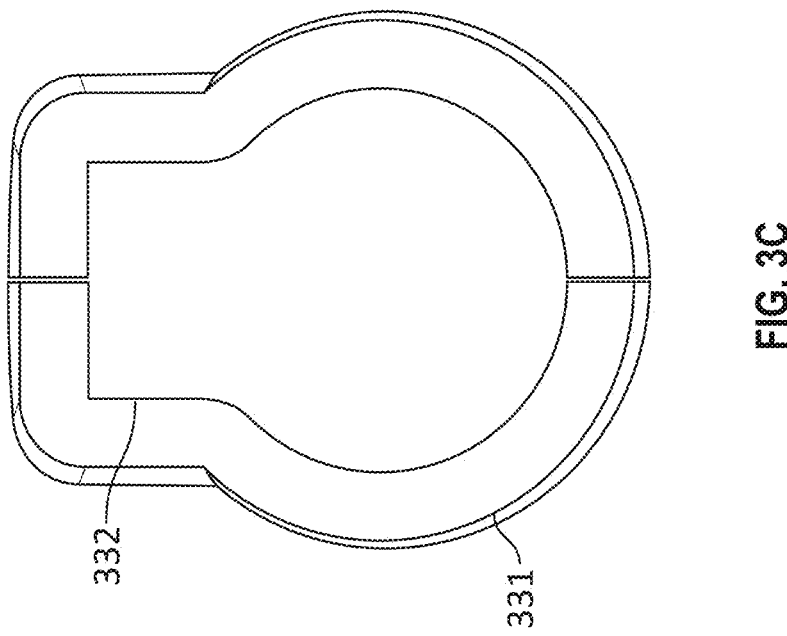

In an example as illustrated in FIGS. 3A-3B, the guide track 250 (or the groove therein) can have keyhole-shaped cross section. FIG. 3C-3D illustrate by way of example and not limitation various shapes of the cross section of the guide track 250. FIG. 3C illustrates a keyhole shape that includes a partially circular portion 331 and a partially squared portion 332. The guide track 250, or the groove therein, can therefore comprise a cylindrical groove portion next to a rectangular groove. FIG. 3D illustrates a keyhole shape that includes a first partially circular portion 341 and a second partially circular portion 342. A keyhole-shaped guide track can better accommodate implants with different design, geometry, or size of electrode arrays associated with the elongate member 141. For example, with electrode arrays affixed to, and at least partially radially projected from, a portion of the elongate member, the keyhole-shaped guide track 250 can correctly orient electrode contacts or implant, and maintain the redial orientation of the implant with respect to elongate member 141 inside the guide track 250 during the insertion or retraction of the elongate member 141. For example, the elongate member 141 can be fit into and move along the cylindrical groove portion, and the attached electrode arrays can be fit into and move along the rectangular groove portion.

In an example of cochlear implant, the electrode arrays of certain implant types can be asymmetrical with the half-banded electrode contacts facing one direction. These electrode array implants are designed to be inserted with the contacts facing toward the target nerve (acoustic nerve). In some examples, an access tab can be affixed to the electrode array. The access tab can project from the electrode array, thus facilitating grasp of the electrode array with tools such as forceps, or inserting the electrode array such that the electrodes contacts correctly face the target nerve. Examples of the access tab can include a flange or a wing structure. The keyhole-shaped guide track 250 can help maintain a correct orientation of the electrode array, such that the access tab of the electrode can slide linearly in the guide track 250. This can prevent the electrode array from rotating unintentionally during insertion. By adjusting the angle of the drive head 220, the user can control the direction the of the flange therefor controlling the direction of the electrode contacts in the cochlea.

FIGS. 4A-4F are diagrams illustrating by way of example different views of an implant drive head 400 configured to accommodate at least two elongate members. The figures show side views of an exterior (FIGS. 4A-4B), side views of an interior (FIGS. 4C-4D), and bottom views (FIGS. 4E-4F) of the drive head 400, which is an embodiment of the implant drive head 220. The sheath 420 forms at least a first guide track 422 sized and shaped or otherwise configured to accommodate a first elongate member 412, and a second guide track 424 sized and shaped or otherwise configured to accommodate a second elongate member 414. The implant drive head 400 can be referred to a double-barrel drive head in this document. The guide tracks 414 and 424 can be arranged in parallel and next to each other, as shown in FIGS. 4A-4F. In some examples, the guide tracks 414 and 424 are two grooves with respective depths and shapes to accommodate respectively the elongate members 412 and 414, and to prevent rotation or twisting of said elongate members while in motion inside the respective grooves. The sheath 420 can provide lateral and peripheral support to the first and second elongate members 412 and 414, which can move longitudinally within their respective guide tracks 422 and 424. In an example, the elongate members 412 and 414 are of the same type of elongate members or implants. In another example, the elongate members 412 and 414 are of different types of elongate members or implants. By way of example and not limitation, the first elongate member 412 can be one of an insertion sheath, a stylet, a guide needle, or a protective covering, and the second elongate member 414 can be one of an electrode array implant, a catheter, a neurostimulator, or a deep brain stimulator. The elongate members 412 and 414 can have the same size and shape, or different sizes or different shapes.

Although two elongate members and two guide tracks are discussed in the illustrated examples, it is by way of example and not limitation. In various examples, the sheath 420 can include three or more guide tracks each sized and shaped or otherwise configured to accommodate respectively separate elongate members, and implant robotic control can be added for additional modular robotic control of implant.

The implant drive head 400 can include one or more wheels 440, and spring loaded guide tips such as the torsion spring 231 that provides compression on the elongate member for frictional motion. The wheels 440 are embodiments of the coupling unit 111 as illustrated in FIG. 1. In an example, the wheels 440 can include a drive wheel and an idler wheel arrangement. The elongate member can be compression-engaged between the driver wheel and the idler wheel. The idler wheel can be spring-biased and compress against the driver wheel, via a torsion spring. The torsion spring can be manually biased to release the compression and open the space between the drive wheel and the idler wheel to accommodate the elongate member into the implant-positioning unit. Commonly assigned U.S. Patent Application No. PCT/US2018/018182 entitled "MODULAR IMPLANT DELIVERY AND POSITIONING SYSTEM," refers to wheel arrangement to engage elongate members of an implant, the description of which is incorporated herein by reference in its entirety.

The wheels 440 can engage and drive the elongate implants 412 and 414 in parallel or in series to control positioning and delivery of the implant to a target site. In an example, the elongate implants 412 and 414 can be engaged and controlled independently by different drive wheels. In an example, at least one of the wheels 440 can include multiple guide grooves to engage respectively elongate members 412 and 414. The guide grooves can have different depth or shape to engage different elongate members such as having different diameters. In some examples, separate wheels can be used to drive the first and second elongate members 412 and 414. The separate wheels can be powered by distinct drive motors and control. In an example, the elongate members 412 and 414 can be coupled to each other, and can be driven in parallel together. Then each member can be moved individually by locking individual tracks via a locking mechanism (as discussed below) to move the first or the second elongate member relative to the other.

Figure 4A:
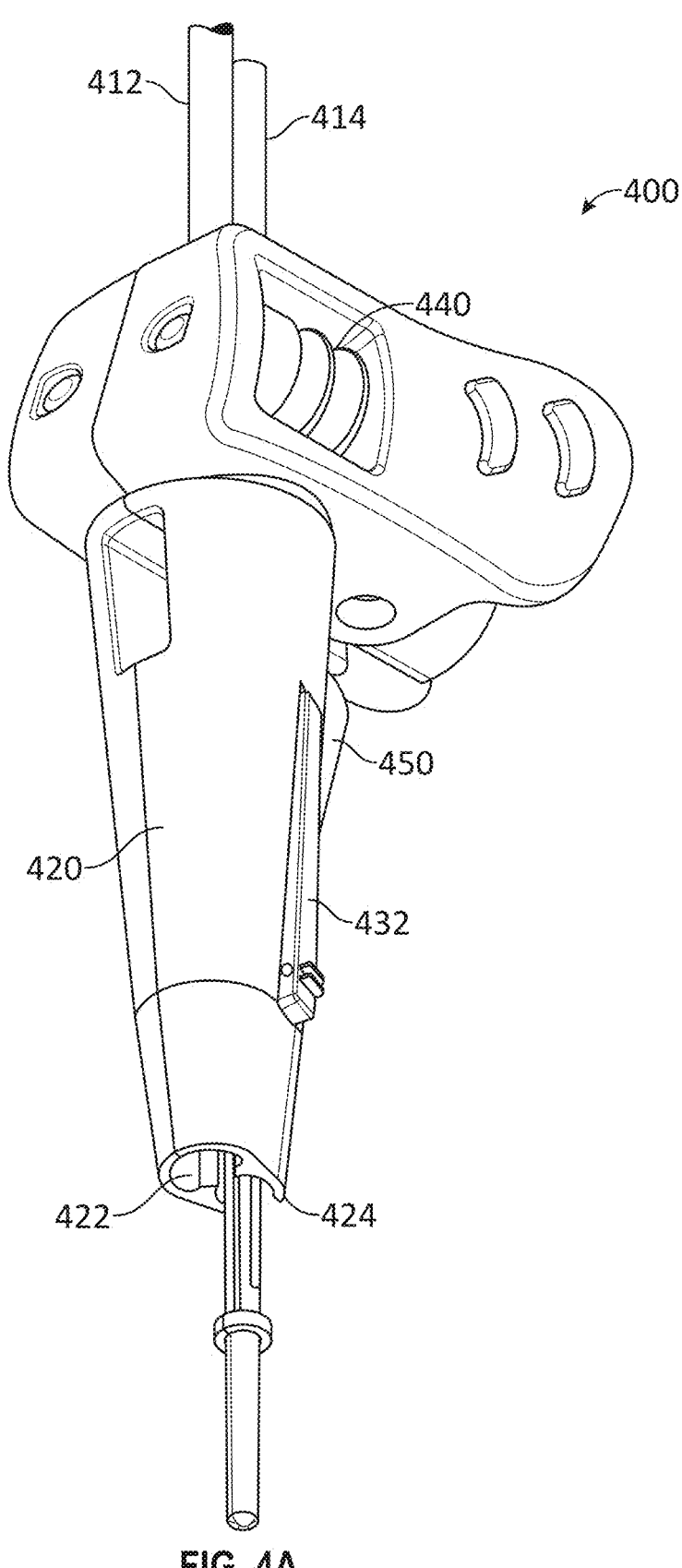
FIGS. 4A-4F are diagrams illustrating, by way of example and not limitation, different views of an implant drive head configured to accommodate at least two elongate members.
Figure 4B:
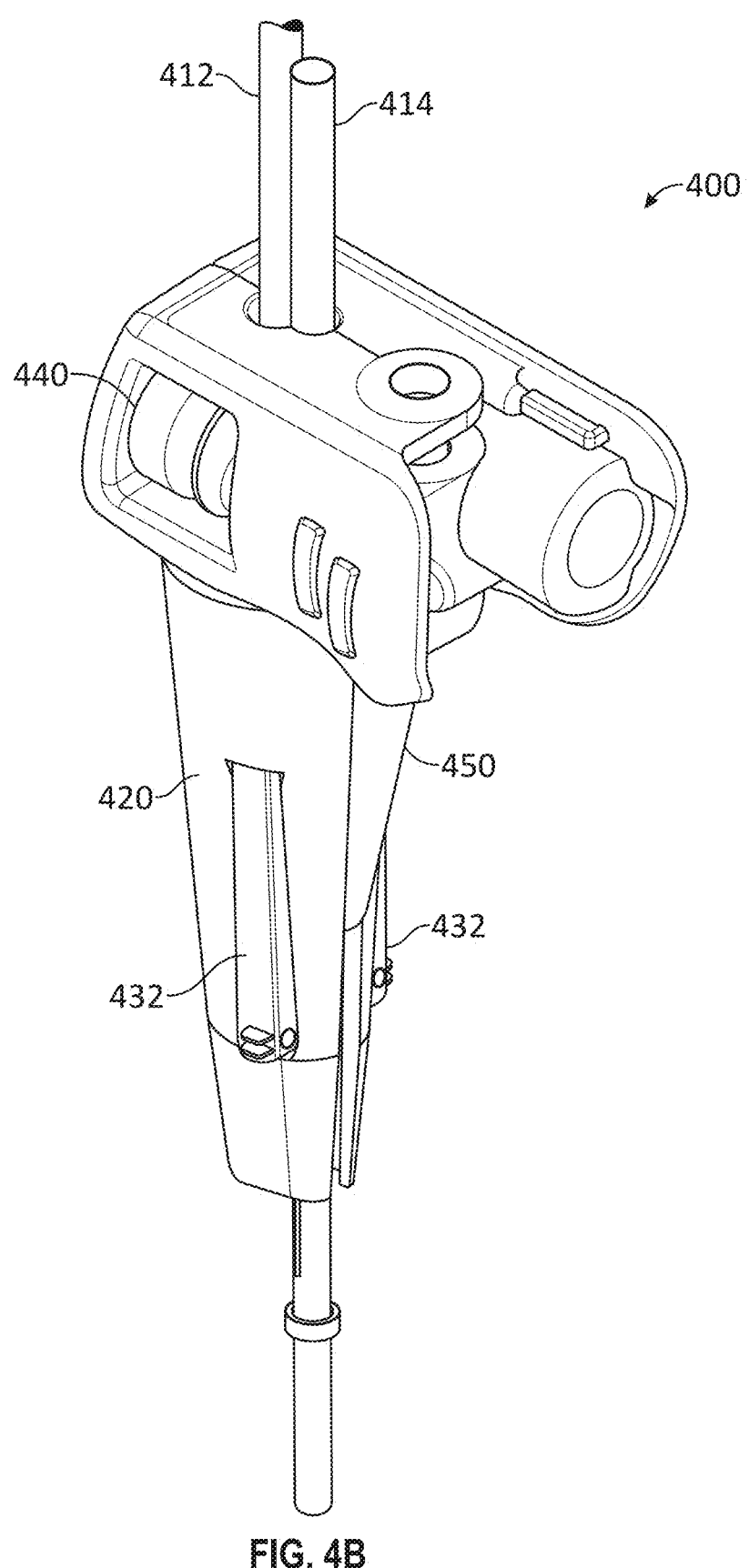
Figure 4C:
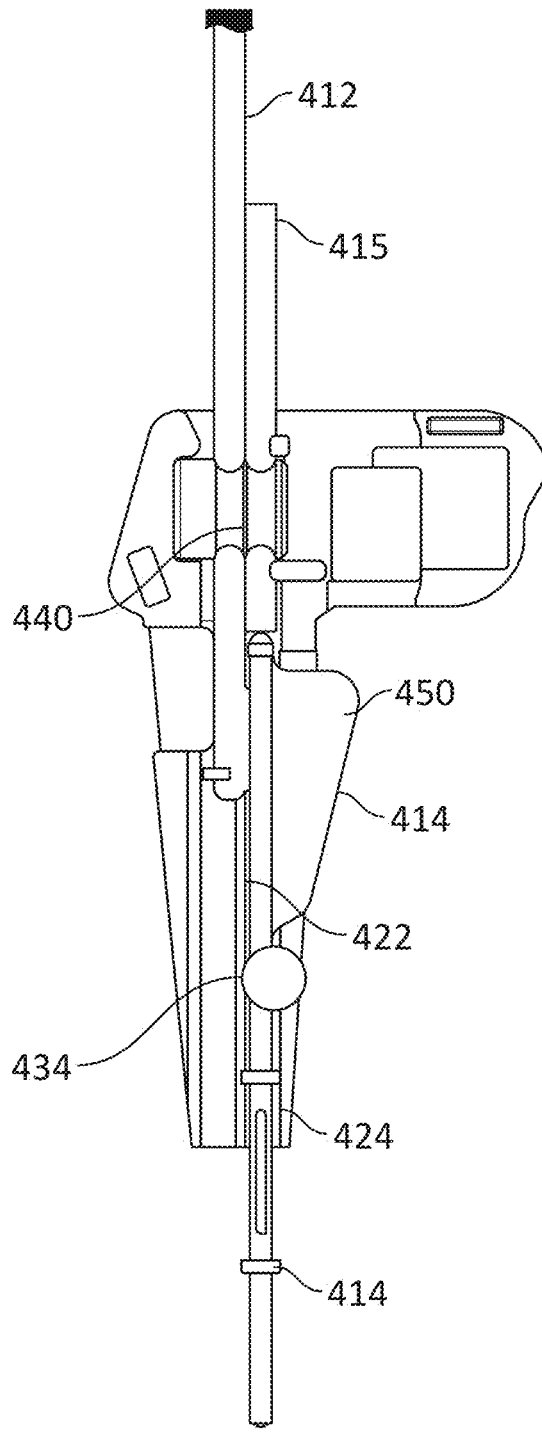
Figure 4D:
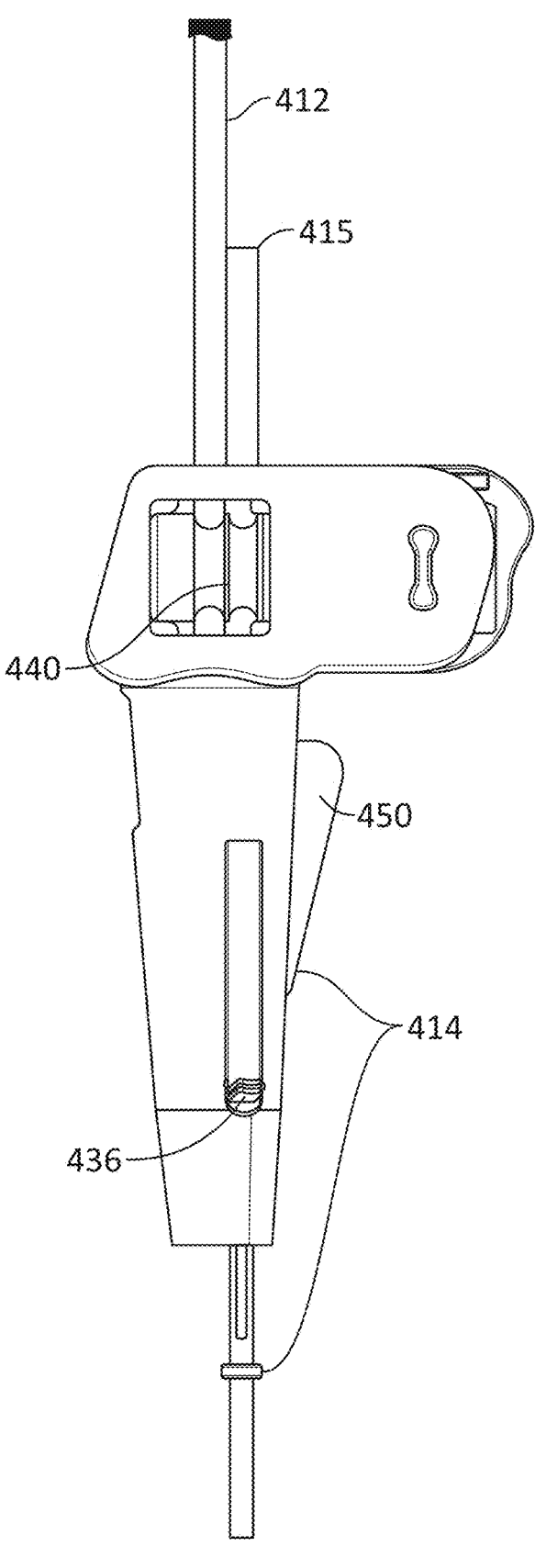

FIGS. 4C and 4D illustrate double wheels 440 each configured to respectively engage the first and second elongate implants 412 and 414. Alternatively, the elongate implants 412 and 414 can be engaged and controlled by the same wheel or set of wheels at different times. In an example, the delivery and positioning of an implant (e.g., a cochlear implant) involves sequentially deploying an insertion sheath via one elongate member, and once the insertion sheath is in place, passing the implant through the deployed sheath and position the plant at the implant site.

As illustrated in FIGS. 4A and 4B, the first elongate member 412 can include an electrode array detachably coupled to a push rod/plunger or a guidewire. The second elongate member 414 can include an insertion sheath detachably coupled to a push rod/plunger or a guidewire. FIGS. 4C and 4D illustrates a push rod/plunger 415, as a part of the elongate member 414, that can be inserted through the entrance port of the drive head 400, and positioned on top of and aligned with the insertion sheath of the elongate member 414. The push rod/plunger 415 can be driven in a linear motion such that it pushes the second elongate member 414 under the insertion sheath. The wheels 440 can initially engage only one elongate member (e.g., the second elongate member 414), such as via a first guide groove on at least one of the wheels 440. In an example, the second elongate member 414 can be robotically pushed forward linearly inside the guide track 524 until it emerges out of the exit port at the distal end of the guide track 524. Motion of the elongate member 414 can be controlled via user input controls on the user interface module, or through a peripheral input device such as a foot pedal or a handheld device.

Once the second elongate member 414 is in position, the insertion sheath can be held in place at the designated position of the surgical opening of the implantation. In some examples, the distal end of the insertion sheath can be fixed or reversibly stabilized at a designated position. In an example of cochlear implant, the distal end of the insertion sheath can be stabilized at the cochlea round window (RW) or cochleostomy site by closely matching tube diameters to the RW niche or cochleostomy dimensions. The push rod/plunger or guidewire part of the elongate member 414 (e.g., the rod/plunger 415) can then be withdrawn from the guide track 524 and pulled out from the entrance port on the top of the drive head. Then, the wheels 440 can compress and engage the first elongate member 412, such as via a second guide groove different from the first guide groove on at least one of the wheels 440. Removing the push rod/plunger 415 can decrease the distance between the wheels 440 (e.g., between the drive wheel and idler wheel), such that said wheels can fictionally engage the first elongate member 412. The first elongate member 412, once engaged, can be robotically pushed forward linearly inside the guide track 522 until reaching out of the exit port of the guide track 522. Motion of the elongate member 412 can be controlled via user input controls on the user interface module, or through a peripheral input device such as a foot pedal or a handheld device. The first elongate member 412 (with the attached electrode array) can further be pushed into and pass through the lumen of the previously deployed insertion sheath, until the first elongate member 412 is out of the insertion sheath and advances into the cochlea implant site. The electrode array associated with second elongate member 412 can then be released and positioned to the target site.

Figure 4E:
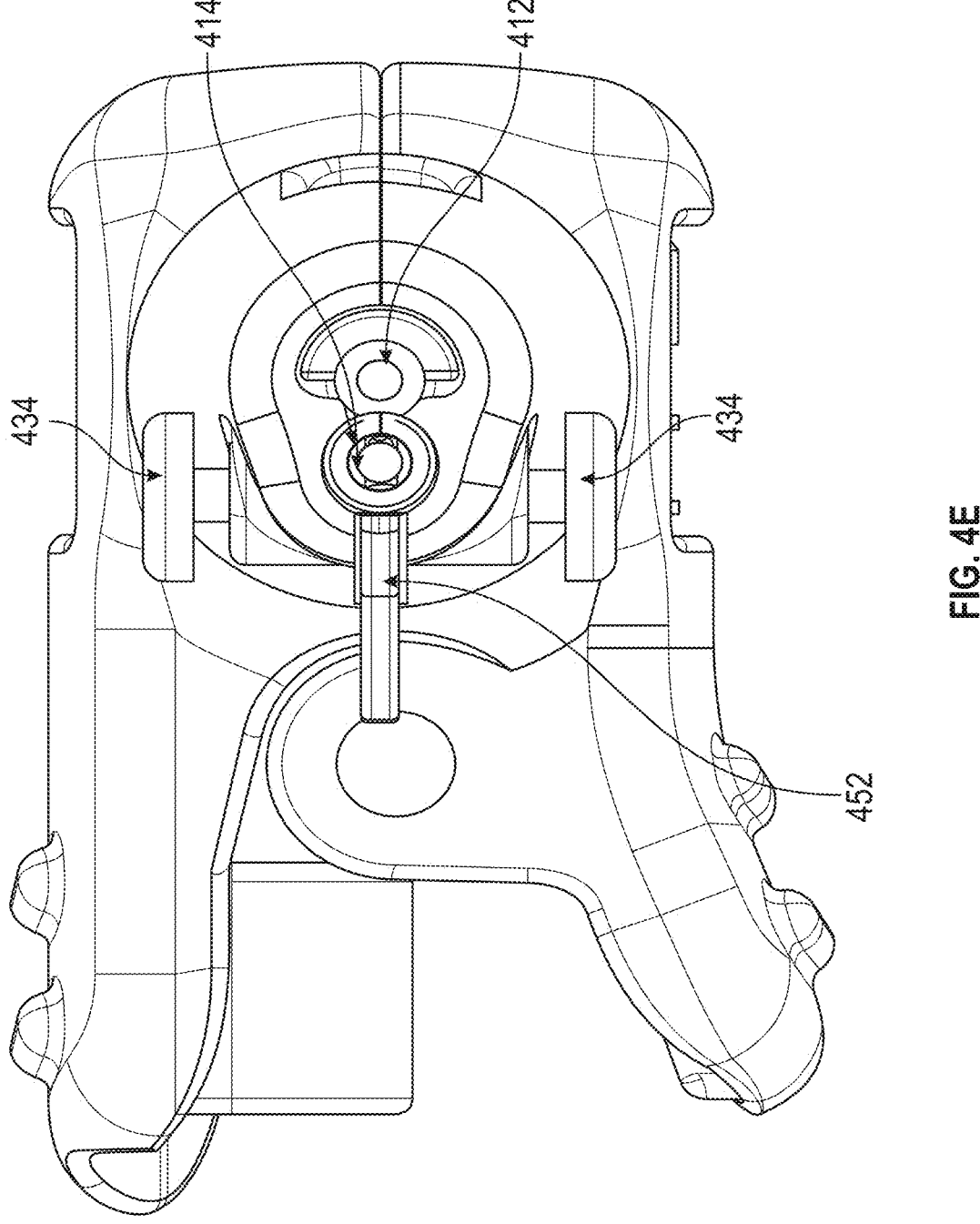
Figure 4F:
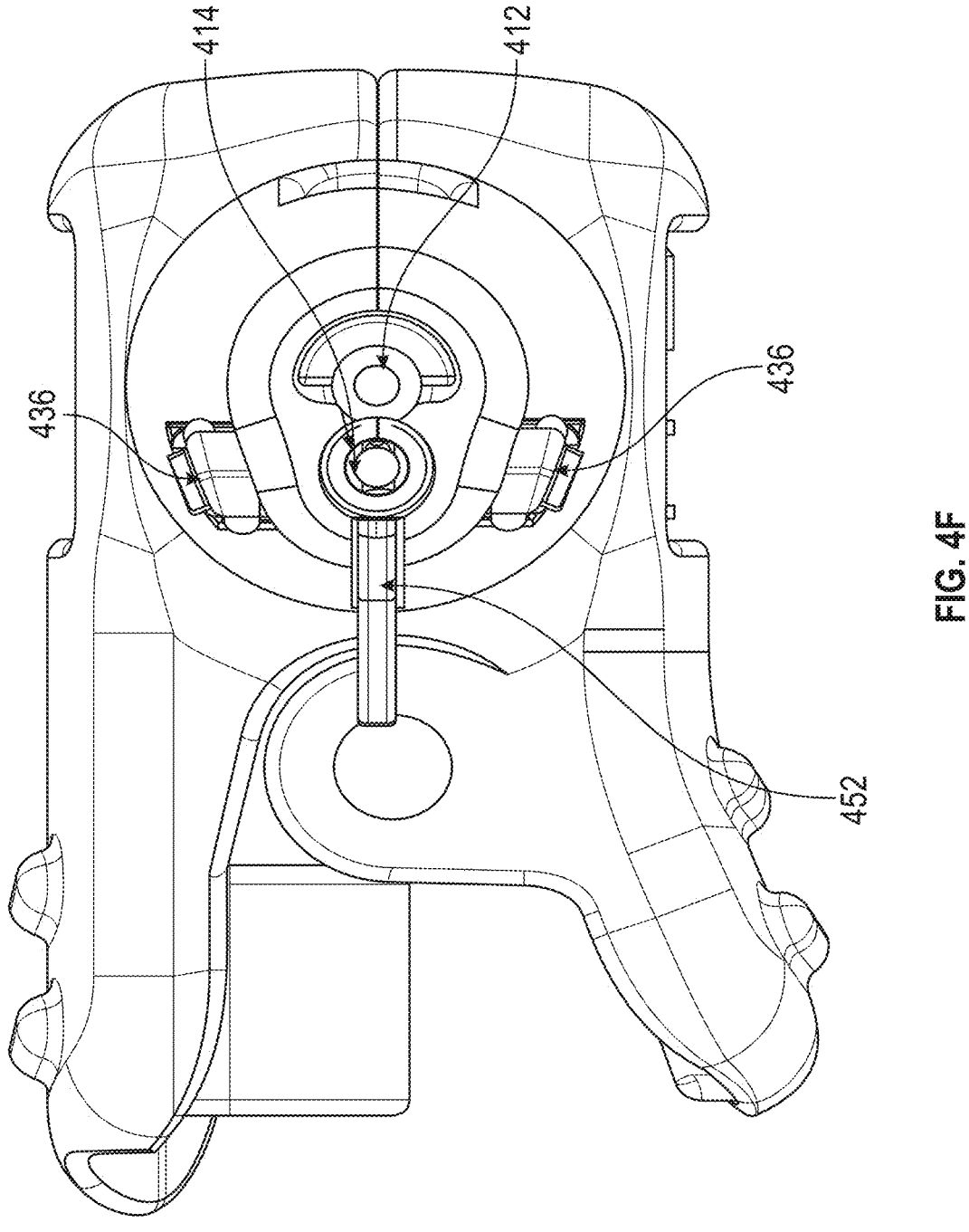

For the drive head 400 to push the first elongate member 412 out of the second elongate member 414, a locking mechanism can be used to secure the second elongate member 414. Examples of the locking mechanism can include locking tabs, clips, or plugs located on the sheath 420 distally or proximally above the drive head. By way of example and not limitation, FIGS. 4A-4B illustrate locking tabs 432, and FIGS. 4C and 4E illustrate push plug locks, and FIGS. 4D and 4F illustrate clip locks, all of which are embodiments of the locking mechanism that can secure the elongate member (e.g., the second elongate member 414) once robotically positioned. In some example, the second elongate member 414 can be secured above the drive head or other external or remote location to decrease size and drive head components in surgical field.

As an alternative to two separate elongate members coupled respectively to an electrode array and an insertion sheath, in some examples, the electrode array and the insertion sheath can be coupled to one elongate member 412 or 414. For example, the electrode array can ride over the second elongate member 414 that includes the insertion sheath. The electrode array and the insertion sheath can move together in parallel within the guide track 524. Then each of the electrode array or the insertion sheath can be moved individually relative to the other by unlocking or uncoupling the individual members. In an example, the unlocking or uncoupling can be carried out via the locking mechanisms (e.g., push tabs or clips) on the guide track 524. The electrode array and the insertion sheath can then move relative to the other locked stationary either by sliding over, within, or in parallel to each.

The implant drive head 400 can include a flange 450 to facilitate grasp with forceps if manually inserting the elongate member 412 or 414 to ensure correct contacts to the target tissue (e.g., facing the auditory nerve). As discussed above with reference to FIGS. 3A-3B, the keyhole-shaped guide track can help maintain a correct orientation of the electrode array, such that the flange of the electrode can slide linearly in the guide track 250. This can prevent the electrode array from rotating unintentionally during insertion. In various examples such as illustrated in FIGS. 4E and 4F, a flange slot 452 is included in the flange 450 to allow the elongate member, such as the second the second elongate member 414 in this example to slide linearly in the guide track 424. This can prevent the electrode array from rotating unintentionally during insertion.

FIG. 5 illustrates, by way of example and not limitation, a method 500 for delivering and positioning an implant into a target implantation site of a patient via an external robotically controlled implantation system, such as the robotically assisted implantation system 100. In an example, the method 500 can be used to operate the robotically controlled implantation system to advance an electrode array of a cochlear implant to a target cochlear region to restore hearing loss via electrostimulation. The method 500 can also be used for operating the robotically controlled implantation system to deliver, steer, position, or extract other types of implants or prosthesis. Examples of such implants can include leads, catheter, guidewire, or other mechanical or electrical devices. The implants can be used for diagnosing a disease or other conditions, or alternatively or additionally be used in the cure, mitigation, treatment, or prevention of disease, such as implantable electrodes for delivering electrostimulation at cardiac, neural, muscular, or other tissues.

The method 500 can begin at step 510, where a communication link is established between an external positioning unit and a control console. The external positioning unit includes mechanical components for engaging a portion of an elongate member of the implant. An example of the external positioning unit includes the implant-positioning unit 200, or a variant thereof, for engaging an array of a cochlear implant. In some examples, the external positioning unit can include a power system with a motor to generate driving force and motion, and a power transmission unit to transmit the driving force and motion from the motor to motion of the elongate member of the implant. The controller console include circuitry for generating a motion control signal according to the motion control instructions provided by the user. The motion control signal can control the power system to regulate one or more motion parameters of the elongate member.

The communication link between the external positioning unit and the control console can include a wired connection including universal serial bus (USB) connection, or otherwise cables coupled to communication interfaces on both the control console and the power system. In another example, the communication link can include a wireless connection including Bluetooth protocol, Bluetooth low energy protocol, near-field communication (NFC) protocol Ethernet, IEEE 802.11 wireless, an inductive telemetry link, or a radio-frequency telemetry link, among others.

At 520, at least a portion of the elongate member of a cochlear implant can be engaged to the external positioning unit. The cochlear implant can include an implantable stimulator for subcutaneous implantation under the scalp. The implantable stimulator can generate electrostimulation impulses conducted to the electrode array for stimulating cochlear nerves. The cochlear implant can include an elongate member with an electrode array disposed at a distal portion of the elongate member. The external positioning unit can include a coupling unit that can interface with the elongate member. Examples of the coupling unit can include one or more wheels 440, such as a drive wheel and an idler wheel arrangement, where the idler wheel can be spring-biased and compress against the driver wheel, via a torsion spring. The elongate member of the implant can be fed through the external positioning unit via an entrance port (such as the entrance port 251 of the drive head 220) and an exit port (such as the exit port 252 of the drive head 220), and compression-engaged between the driver wheel and the idler wheel.

In an example, the elongate member can be at least partially inserted into the external positioning unit manually by a user (e.g., a surgeon) using forceps. The implant drive head can include a flange to facilitate grasp with forceps. As discussed above with reference to FIGS. 3A-3B, the keyhole-shaped guide track can help maintain a correct orientation of the electrode array, such that the flange of the electrode can slide linearly in the guide track 250. This can prevent the electrode array from rotating unintentionally during insertion. In various examples such as illustrated in FIGS. 4E and 4F, a flange slot 452 is included in the flange 450 to allow the elongate member, such as the second the second elongate member 414 in this example to slide linearly in the guide track 424. This can prevent the electrode array from rotating unintentionally during insertion.

At 530, the external positioning unit can be affixed to a patient, such as on the patient head to maintain sufficient stability during the advancement of the implant. The external positioning unit can alternatively be securely attached to an object at the patient's immediate environment such as an equipment attached to a surgical table. As previously discussed with reference to FIG. 1, the external positioning unit can be sized and shaped to facilitate patient attachment. The external positioning unit can include a fixation member, such as one or more of a screw, a pin, a nail, a wire, a hook, a suture, or a magnet. The external positioning unit can have an exterior contact surface with a rough texture, or can be equipped with one or more gripping elements. Examples of the gripping elements can include penetrators such as spikes, pins, or barbs protruding from the exterior surface. When the exterior contact surface is in contact with a body part of the patient (e.g., patient head) and the external positioning unit is pressed and held against the body part, the gripping elements can provide sufficient friction or gripping force to securely hold the external positioning unit in place during the implant advancement.

At 540, an implant can be delivered and positioned into the target implantation site through a robotic control of the external positioning unit. In an example of cochlear implant, the electrode array of the cochlear implant can be inserted into and positioned at the target cochlear site. In patients with impaired high-frequency hearing function but preserved low-frequency hearing function, a short electrode array of the implant can be positioned at the outer or basal cochlea. Electrostimulation can be delivered therein via the electrode array to restore high-frequency hearing function. The robotic control of the implant movement can involve generating a motor control signal from the control console according to user programming instructions. The motor control signal can be transmitted to a motor located inside the control console or inside the external positioning unit. The motor can generate driving force and motion that control various motion parameters of the elongate member of the implant via the power transmission unit. The control console can regulate the electrode array movement further based on sensor feedback on the position of the implant, motion the implant, or the force or friction applied to the implant.

Figure 6:
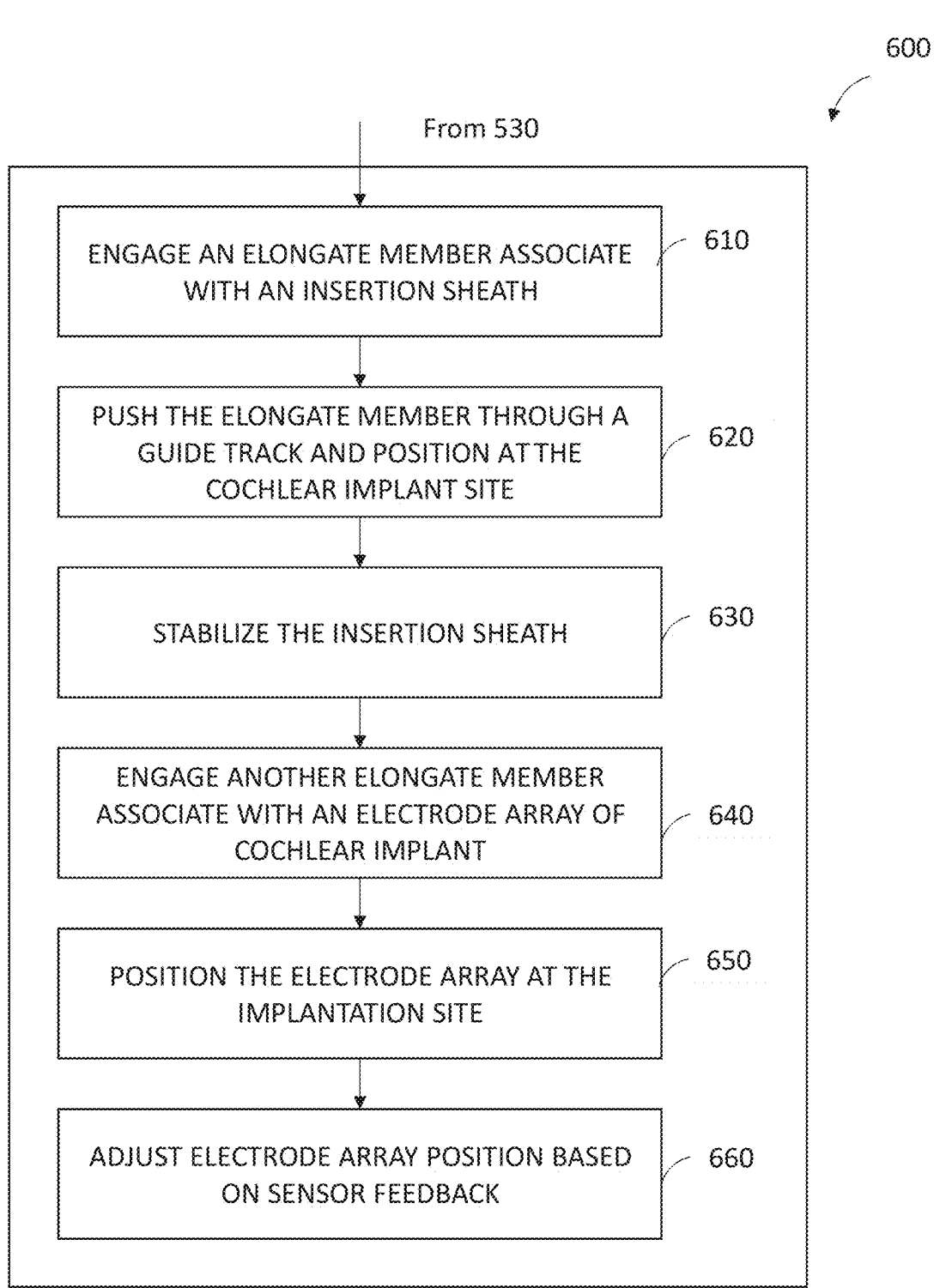
FIG. 6 illustrates, by way of example and not limitation, a method for robotic delivery and positioning of a cochlear implant.

FIG. 6 illustrates, by way of example and not limitation, a method 600 for robotic delivery and positioning of a cochlear implant. The cochlear implant can be fed into a sheath. The distal end of the sheath can be introduced to the entrance of the surgical site, such as a cochlear entrance for cochlear implant placement. The cochlear implant can then be pushed out of the sheath and deployed to the cochlear implant site. The method 600 is an embodiment of the step 540 of the method 500 as illustrated in FIG. 5. The method 600 can be used for operating at least a portion of the external robotically controlled implantation system, such as the implant drive head 200 or a variant thereof, such as the implant drive head 300 or 400.

The method 600 can begin at 610, where an elongate member associated with an insertion sheath, such as the second elongate member 414 as illustrated in FIGS. 4A-4D, can be engaged with a drive head, such as one of the drive head 200, 300, or 400. The engagement can be through one of multiple guide grooves of the wheels 440. At 620, the elongate member can be robotically pushed forward linearly inside the guide track of the drive head, until emerging out of the exit port at the distal end of the guide track. Motion of the elongate member can be controlled via user input controls on the user interface module, or through a peripheral input device such as a foot pedal or a handheld device. The insertion sheath can then be positioned to the target site as needed, such as the round window of the cochlea.

Once the second elongate member is in position, the insertion sheath can be stabilized at the designated position of the surgical opening of the implantation at 630. In some examples, the distal end of the insertion sheath can be fixed or reversibly stabilized at a designated position. In an example of cochlear implant, the distal end of the insertion sheath can be stabilized at the cochlea round window (RW) or cochleostomy site by closely matching tube diameters to the RW niche or cochleostomy dimensions. In some examples, the insertion sheath can be stabilized using a locking mechanism on the drive head. Examples of the locking mechanism can include locking tabs, clip locks 436, or push plugs 434, among others such as those illustrated in FIGS. 4A-4E.

By stabilizing the insertion sheath via the locking mechanism, at 640, an elongate member associated with an electrode array of the cochlear implant, such as the first elongate member 412 as illustrated in FIGS. 4A-4D, can be engaged with a drive head. The engagement can be through a guide groove of the wheels 440 different from the groove used to engage the elongate member associated with the insertion sheath. Once engaged, the elongate member (along with the electrode array associated therewith) can be robotically pushed forward linearly inside the guide track until emerging out of the exit port of the guide track. Motion of the elongate member can be controlled via user input controls on the user interface module, or through a peripheral input device such as a foot pedal or a handheld device. The elongate member, along with the attached electrode array, can further pass through the lumen of the previously deployed insertion sheath, until reaching out of the insertion sheath and advancing into the cochlea. The electrode array can then be positioned to the target site at 650.

At 660, implantation site for the electrode array can be adjusted based on sensor feedback. The sensor can be positioned at the electric motor, the power transmission unit, or inside the external positioning unit such as at the wheels 440. Examples of the sensors can include encoders, Hall effect sensors, or optional sensors for detecting the position of the implant, capacitive sensors for detecting implant motion, or force sensors for sensing a parameter indicative of force or friction imposed on the implant during the implant advancement, such as axial, lateral, or radial insertion force as the implant advances into the cochlea. The force can also be indirectly sensed by measuring the current supplied to the electric motor. During the implantation process, one or more sensors can sense information about position and motion of the implant.

Figure 7:
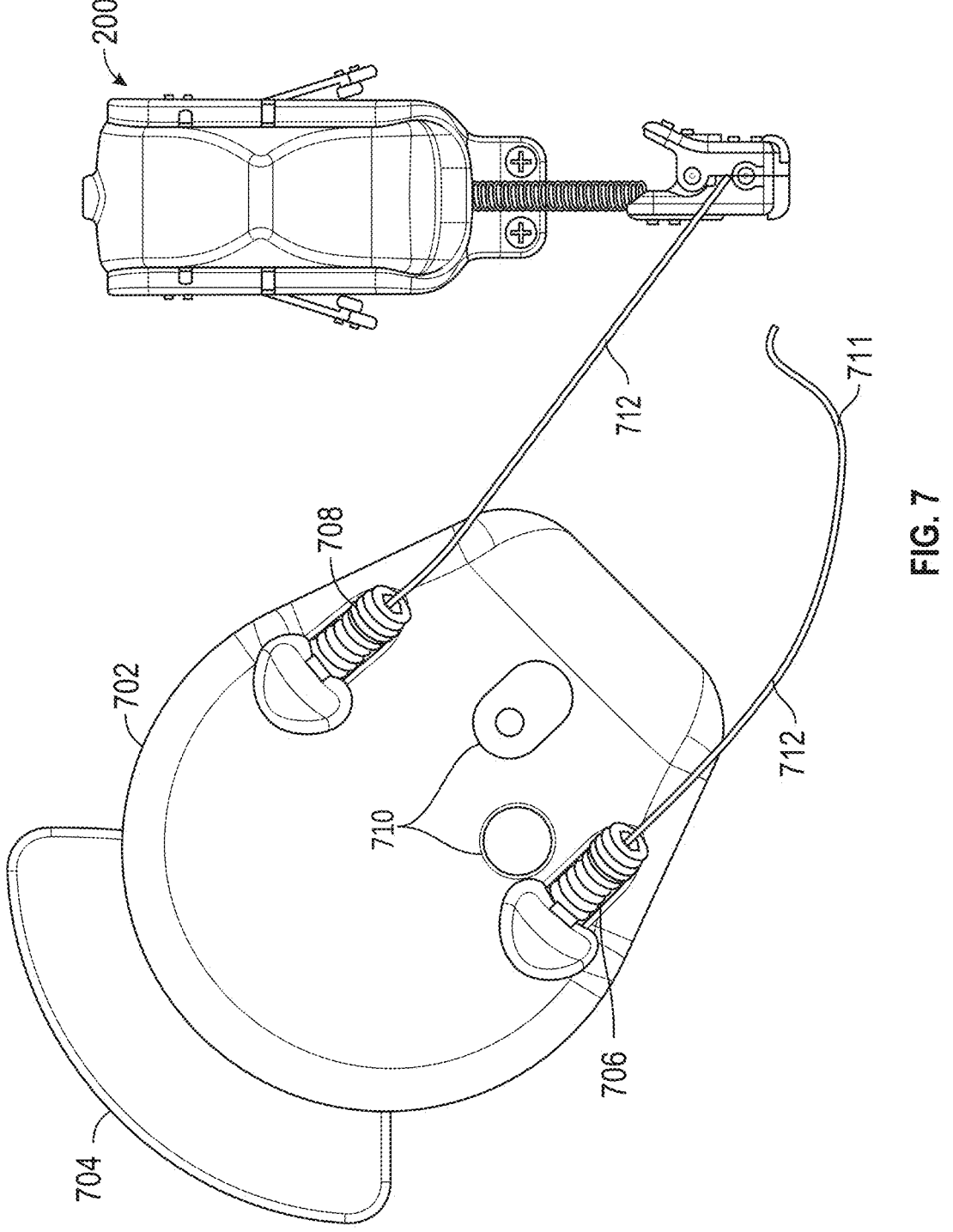
FIG. 7 illustrates, by of example and not limitation, an example of a biofeedback system configured to communicate with an implant positioning unit.
Figure 8:
FIG. 8 illustrates, by way of example and not limitation, an example of a biofeedback system configured to communicate with, and coupled to, an implant positioning unit.

FIG. 7 illustrates, by way of example and not limitation, an example of a biofeedback system configured to communicate with an implant positioning unit. FIG. 8 illustrates, by way of example and not limitation, an example of a biofeedback system configured to communicate with, and coupled to, an implant positioning unit. FIGS. 7-8 are discussed below concurrently.

The biofeedback system 700 can be configured to communicate with an implant positioning system, for example, the implant positioning system 200 illustrated in FIGS. 2A-2D. The biofeedback system 700 can provide electrophysiological feedback control to a user of the implant positioning system 200 during the insertion of an implant. For example, the electrophysical feedback of the biofeedback system 700 can be electrocochleography (ECochG) feedback. For example, the biofeedback system 700 can provide electrocochleography feedback control, during the positioning of a cochlear implant, using the implant positioning system 200.

The biofeedback system 700 can include a PCB contained with a housing 702. The PCB can be configured to communicate wirelessly and can be battery powered. The biofeedback system can include buttons 710. One of the buttons 710 can be a power button operable to turn the biofeedback system 700 on or off. One of the buttons 710 can a control button configured to control one or more functions of the biofeedback system 700.

The biofeedback system 700 can also include removable and replaceable sensing electrode wires 712. One of the sensing electrode wires 712 can be fed into the implant positing unit 200, as shown in FIG. 7. One of the sensing electrode wires 712 can include a ground electrode 711 at a distal end. The sensing electrode wires 712 can be coupled to the biofeedback system 700 with couplers 706 and 708. The sensing electrodes 712 can be placed to limit the negative effects of impedance drops, or poor sensing electrode placements, while simultaneously inserting an implant electrode using the implant positioning system 200.

The biofeedback system 700 can also include a stabilizing bar 704. The stabilizing bar 704 can be configured to perform real time sensing, impedance checking, physiological micro-signal amplification, physiological micro-signal processing, and Bluetooth Low Energy (BLE) communication with a control console. The stabilizing bar 704 can also be used as a mechanism to secure the biofeedback system to the patient, soft-tissue, or in proximity to a surgical site.

For example, the control console can be the control console 120 illustrated in FIG. 1 and can be configured to communicate with the biofeedback system 700 via Bluetooth Low Energy (BLE) to control electrode insertion using ECochG feedback and display live ECochG signals. The control console 120 can also alert, via an on-screen alert and audible tone, a surgeon of any changes in the ECochG signal that can indicate possible intracochlear trauma.

The control console 120 can include a dedicated hardware/software system such as a programmer, a remote server-based patient management system, or alternatively a system defined predominantly by a controller software running on a standard personal computer. The control console 120 can use measurement data (e.g., electrophysiologic measurements) for closed loop control of implant positioning. In addition to sensing motion parameters, electrophysiologic measures can be linked to system controller through software interfaces or means for inputting to control system in real-time measures such as electrocochleography (ECoG), neural response telemetry, cochlear response telemetry, or auditory brainstem responses (ABRs) recordings from either the cochlear implant or the biofeedback system 700.

Figure 9:
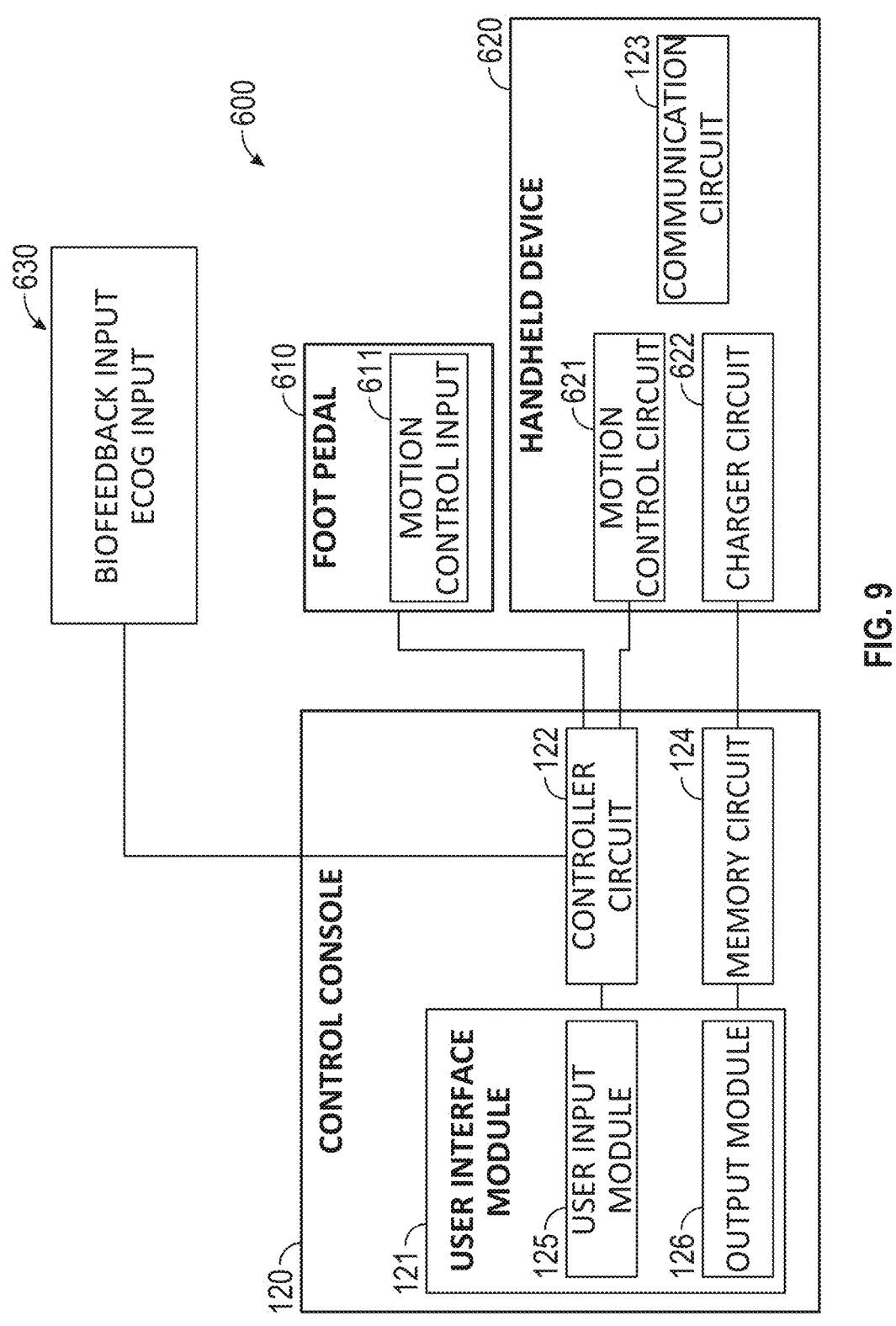
FIG. 9 illustrates, by way of example and not limitation, a block diagram of a portion of a control system for robotically controlling delivery and positioning of an implant using real-time feedback.

FIG. 9 illustrates, by way of example and not limitation, a block diagram of a portion of a control system for robotically controlling delivery and positioning of an implant using real-time feedback. In this example, the control system 900 can optionally include an ECoG input 930. The ECoG input 930 can supply ECoG measurement data in real-time to the controller circuit 922. The ECoG input 930 can link the control system 900 to ECoG measures, such as cochlear microphonics (CM), auditory nerve neurophonics (ANN), which can reflect immediate changes in the cochlear mechanics and insertion trauma pre-, during-, and post-insertion of the electrode array. This type of data can be utilized by the controller circuit 922 to control implant delivery and positioning in real-time with closed-loop feedback based on the ECoG measurements. ECoG recordings are electrical potentials generated in the inner ear, cochlea, and auditory nerve in response to sound or electrical stimulation, using an electrode placed at the sites such as the ear canal, tympanic membrane, round window, or intracochlear. While auditory brainstem responses (ABRs) reflect electrophysiological responses from different neural generators along the brainstem, cochlear microphnics (CM) reflect intracochlear physiology of outer and inner hair cells.

The control system 900 can link, couple, or interface the motion control parameters with real-time, intraoperative electrophysiological measures of cochlear function during electrode insertion to serve as means to determine and set optimal electrode positioning. Interoperability can include linking the software/data from the electrode array or other intracochlear/extracochlear recordings during real-time insertion to the control console feedback mechanism to indicate when optimal electrode position has been achieved based on electrophysiological measures such as neural response telemetry, auditory nerve neurophonics, or cochlear microphonics.

Decreased ECoGs during or after insertion likely reflect changes in cochlear mechanics due to the implant intracochlear position as well as insertion trauma, which are likely mechanisms of hearing loss after implant insertion. For example, CM amplitude changes have been shown to be most affected by inadvertent movement of the array upon physical contact/elevation of the basilar membrane. Therefore, the ability to provide a real-time monitoring link (via ECoG input 930) and feedback to the insertion control system 900 to monitor and fine tune the implant position by robotic-assisted and surgeon controlled micromechanical position adjustments until the ECoG measures such as CM are maintained or optimized per surgeon or audiologist determined preferences. In certain examples, the user interface module 921 can provide real-time feedback of the ECoG measures to the surgeon and enable additional controls responsive to ECoG measures and surgeon input.

With the real-time control system link and interface with ECoG measures during implant insertion, the system can notify the surgeon of potential for real-time physiological injury to intracochlear structures such as contact with the basilar membrane. If decreases or significant changes are recorded in ECoG measures, the system provides feedback to the surgeon in the form of visual or audible notifications and a stop command can be sent to the system controller to prevent further implant motion. After the system notification to the user, the surgeon can adjust implant insertion trajectory or system motion parameters as needed to avoid intracochlear damage or suboptimal electrode position or choose to the override notifications via physical acknowledgement mechanism. After acknowledgment of warning notification, the stop feedback is removed, and the surgeon can continue robotic-assisted insertion of the implant.

The method 940, like method 540 discussed above, is an embodiment of the step 540 of the method 500 as illustrated in FIG. 5. The method 940 can be used for operating a non-implantable, robotically controlled implantation system, such as the robotically assisted implantation system 100. In this example, the method 940 includes operations identical to method 500 with the addition of receiving ECoG measurements at 945. The ECoG measurements can be utilized by the external positioning unit 110 and/or control console 120 to assist in controlling implant positioning and delivery. The method 940 can include an operation for receiving ECoG measurements, which can then be utilized in determining whether a target site is reached at 947. As discussed above, ECoG measurements can be monitored to determine when an optimal implant position is reached or for potential issues with the implant delivery.

Figure 10:
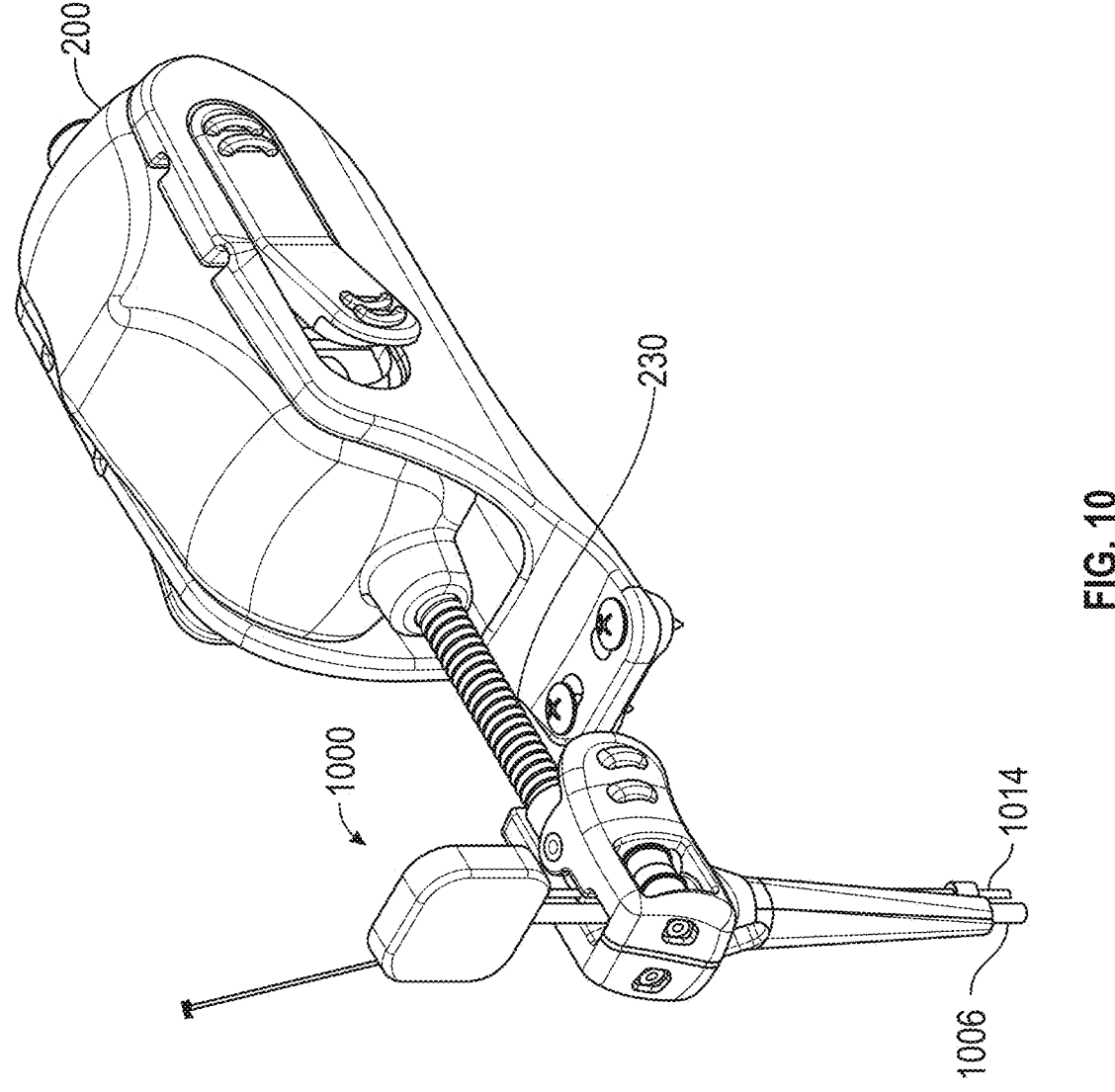
FIGS. 10-11 illustrate, by way of example and not limitation, various examples of an implant positioning unit holding and positioning surgical tools.
Figure 11:
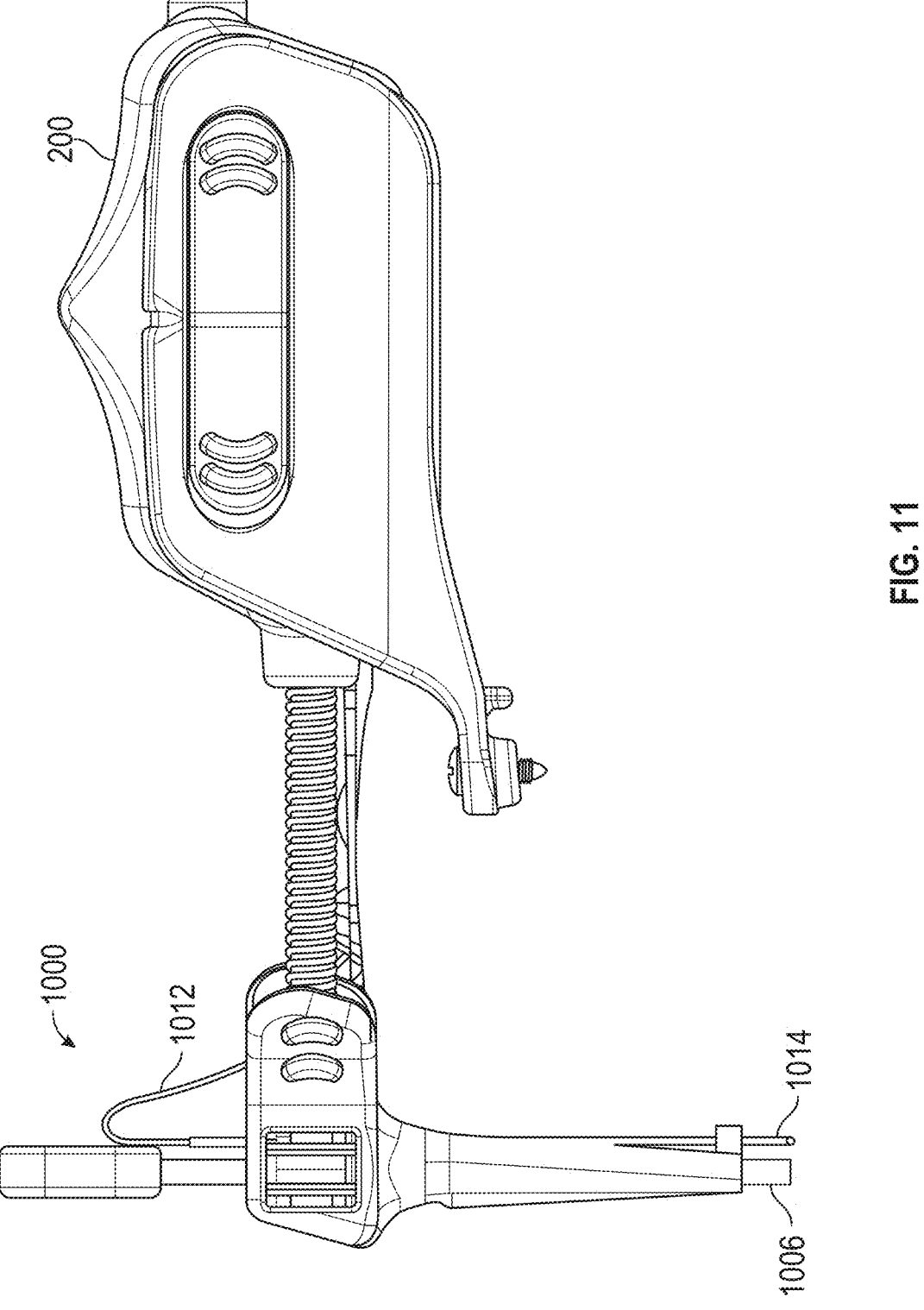

FIGS. 10-11 illustrate, by way of example and not limitation, various examples of an implant positioning unit holding and positioning surgical tools. Any of the previously or later discussed embodiments can be configured to hold and position tools as discussed with respect to FIGS. 10-11. FIGS. 10-11 are discussed below concurrently.

The implant positioning system 200, which can be, for example, the implant positioning system 200 described in FIGS. 2A-2D, can be used to hold and position a variety of surgical tools. For example, as illustrated in FIGS. 10-11, the implant positioning system 200 can hold and position an endoscope camera 1000. The endoscope camera 1000 can be positioned and retained using the drive head 220. Similar to the elongate member 241, the endoscope camera 1000 can be positioned between the drive wheel 223 and the idle wheel 225. The drive wheel 223 can rotate to allow for multiple depth-of-field (DOF) adjustments of the endoscope camera 1000. In this way, the drive wheel 223 and idler wheel 225 of the drive head 220 can be used for precision focusing and/or zoom of the endoscope camera lens 1006, helping to allow for a clear and precise view of a surgical field.

The adjustable arm 230 of the implant positioning unit 200 can also be used to position the camera 1000 at multiple angles. The adjustable arm 230 can be a flexible, or semi-rigid arm. The flexibility of the adjustable arm 230 can allow a user to position the camera 1000 at different viewing angles to an implant insertion site. Finally, the drive head 220 is not limited to holding and positioning cameras, but can hold and position, to allow for robotic motion control, of other tubular and elongated surgical instruments. For example, the drive head 220 and the adjustable arm 230 can together adjustably position guide wires, suction devices, such as through a working channel of an endoscope, catheters, lasers, drills, scalpels, electrodes, or cautery tools.

FIGS. 10 and 11 also illustrate a system that can optionally include aspects of the biofeedback system 700. For example, the system illustrated optionally includes at least one sensing electrode 712.

Figure 12:
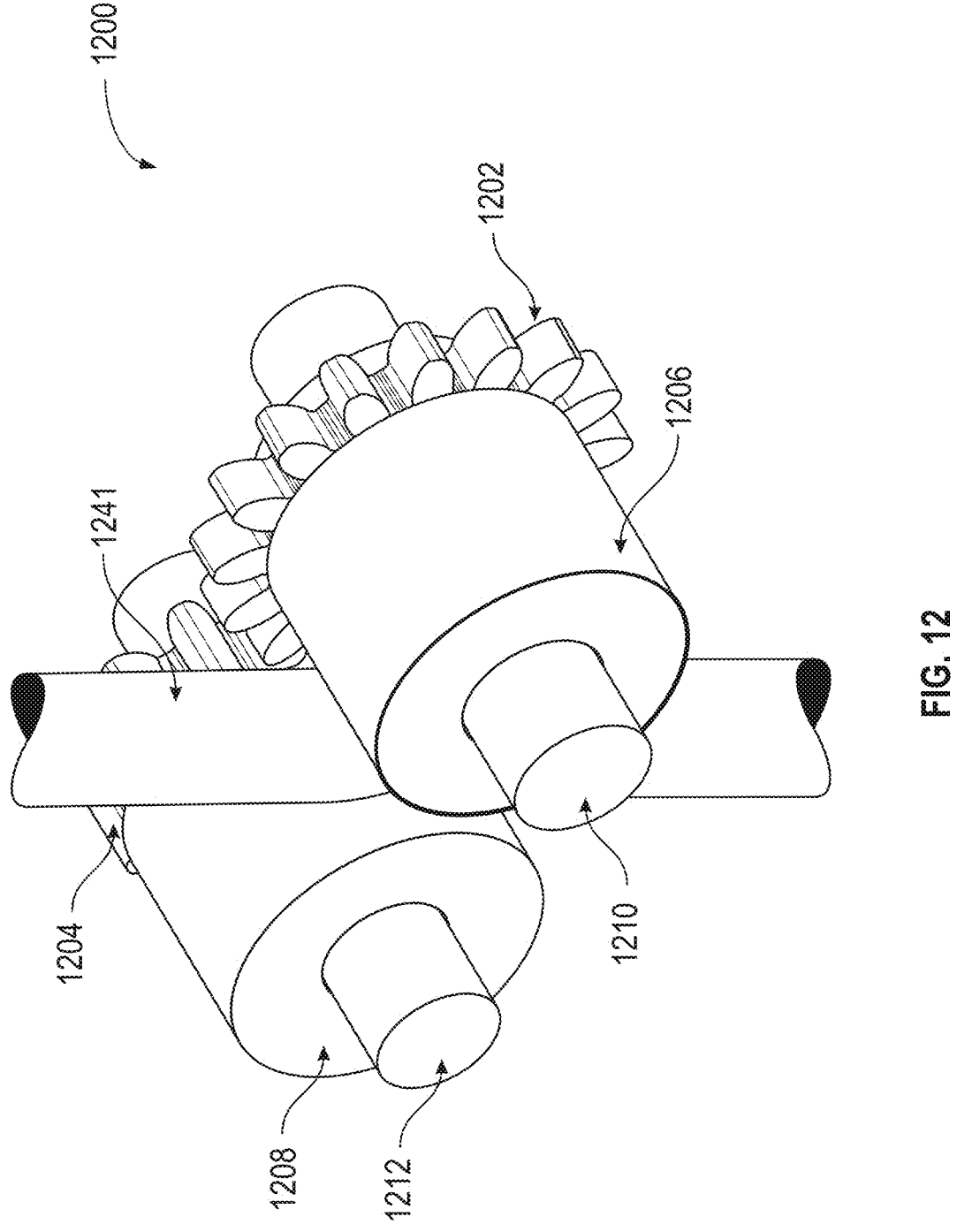
FIG. 12 illustrates, by way of example and not limitation, an illustration of a drive mechanism for an implant positioning unit.

FIG. 12 illustrates, by way of example and not limitation, an illustration of a drive mechanism for an implant positioning unit. The drive mechanism 1200 can optimize engagement with the elongate member 1241 by provided by first and second mechanical gears 1202 and 1204, respectively. The drive mechanism 1200 can be incorporated into any of the examples and embodiments of the present disclosure. The drive mechanism 1200 can increase and double the amount of drive force that can be imparted on an electrode, or and implant, versus a single-drive mechanism, to help improve the ability to advance the electrode or implant into a surgical field.

The drive mechanism 1200 can include a passive drive wheel 1206 and an active drive wheel 1208. The active drive wheel 1208 can be driven by a motor. The passive drive wheel 1206 can engage, and be driven by, the active drive wheel 1208 through the second mechanical gear 1204. The first mechanical gear 1202 can be coupled to the active drive wheel 1208, and second mechanical gear 1210 can be coupled to the passive drive wheel 1206. As the active drive wheel 1208 rotates, the passive drive wheel 1206 is correspondingly rotated through the gears 1202 and 1204, which in turn can increase (such as double) the frictional forces translating the elongate member 1241. By coupling and meshing the active drive wheel 1208 and the passive drive wheel 1206, the physical size of the embodiments and examples of the present disclosure can be reduced, while retaining a similar total drive force. Additionally, when paired with, for example, the biofeedback system 700 illustrated in FIGS. 7-8, the sensing electrodes 712 can be precisely placed, helping to limit negative effects of impedance drops, or poor sensing electrode placements, while simultaneously inserting an implant electrode with the drive wheel of the drive head 220.

Figure 13:
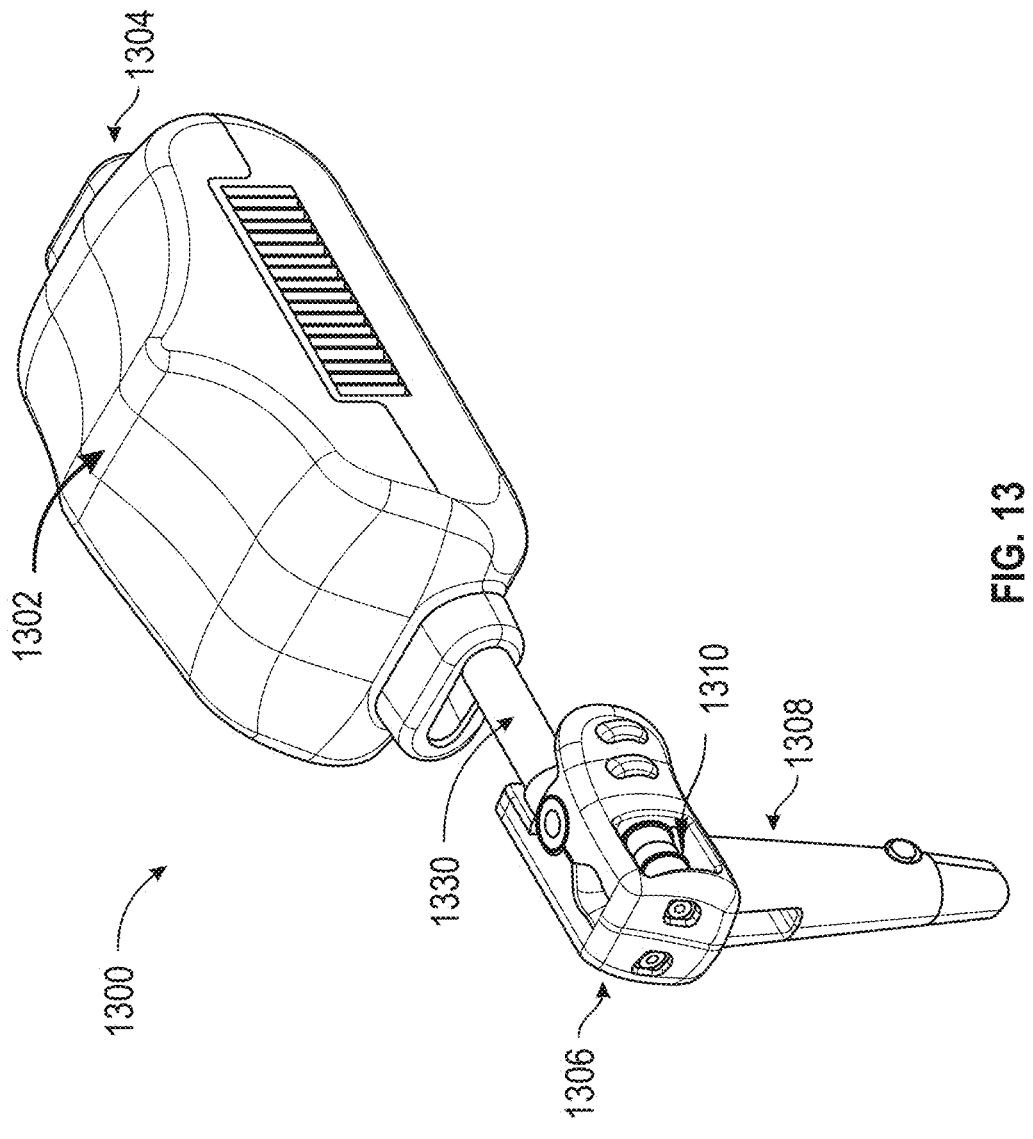
FIG. 13 illustrates, by way of example and not limitation, an illustration of an implant positioning system.

FIG. 13 illustrates, by way of example and not limitation, an illustration of an implant positioning system. The implant positioning system 1300 can include a housing 1302 and a power supply port 1304 configured to receive a power and communication cord. The implant positioning unit 1300 can include a dual drive head 1306, contained within the housing 1302 and the adjustable arm 1330. The dual drive head 1306 can define a sheath 1308, and can include one or more wheels 1310 that provide compression on an elongate member, for frictional motion. The wheels 1310 can be embodiments of the coupling unit 111 as illustrated in FIG. 1. In an example, the wheels 1310 can include a drive wheel and an idler wheel arrangement. The addition of at least a second wheel allows the implant positioning system 1300 to drive two elongate members.

The dual drive head 1306 illustrated in FIGS. 13, as well as FIGS. 14-15 below, can be used to independently adjust two cameras or endoscopes for stereoscopic vision and surgical field mapping. This can allow for a surgeon to robotically adjust for a best-case angle of insertion further preventing unnecessary intracochlear trauma. In the case of an cochlear implantation, the drive wheels 1310 can advance a pre-curved sheathed electrode into the cochlea, then advance only the electrode out of the sheath and into the cochlea, and finally retract the sheath from the implant, and upon removal, leaves only the implant behind. In the case of a stereoscopic camera system, the implant positioning system 1300 can control two cameras independently in order to precisely and accurately map the surgical field in three dimensions with great resolution. Once mapped the implant positioning system can specify whether or not the optimal angle of insertion of a cochlear implant into the cochlea is being used.

Figure 14A:
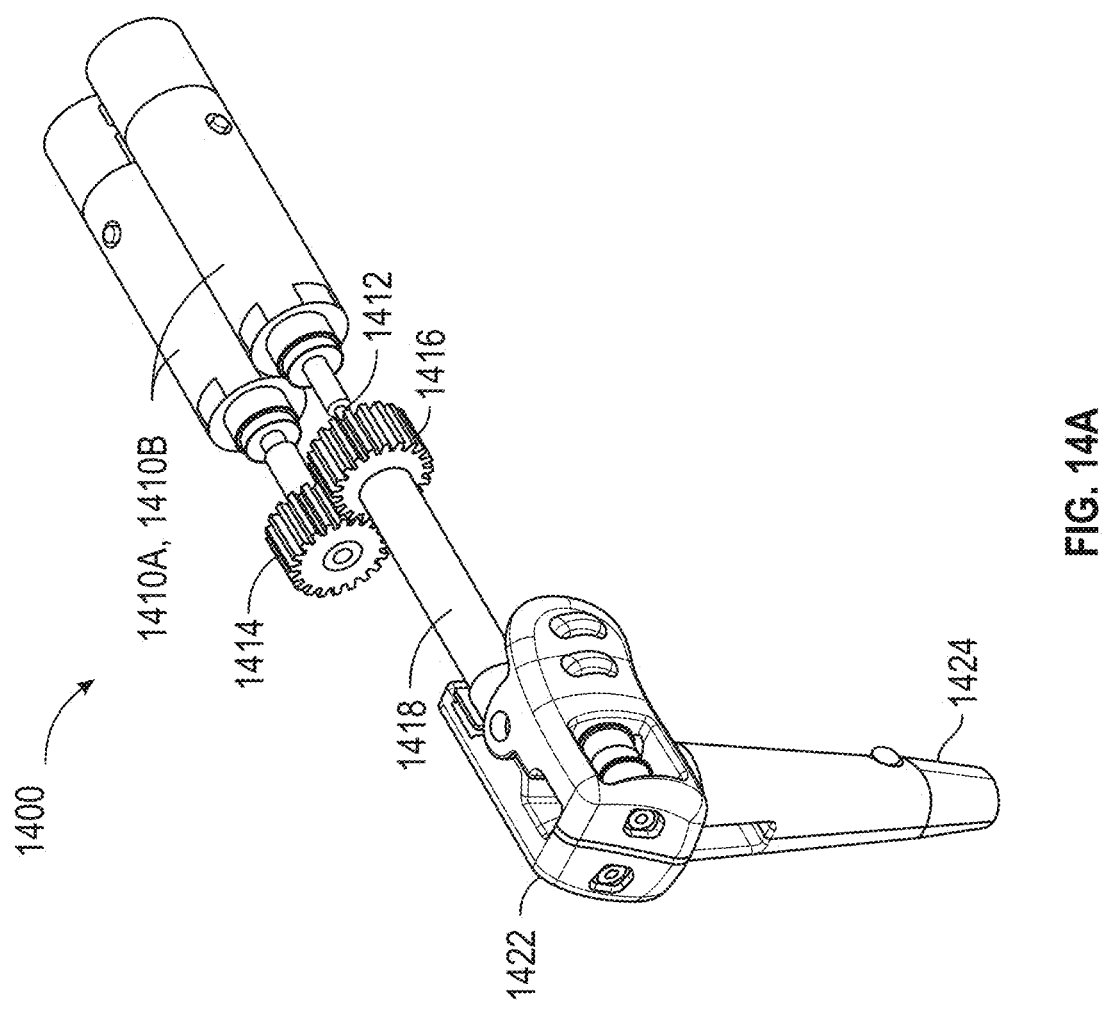
FIGS. 14A-15 illustrate, by way of example and not limitation, illustrations of a drive mechanism for an implant positioning system.
Figure 14B:
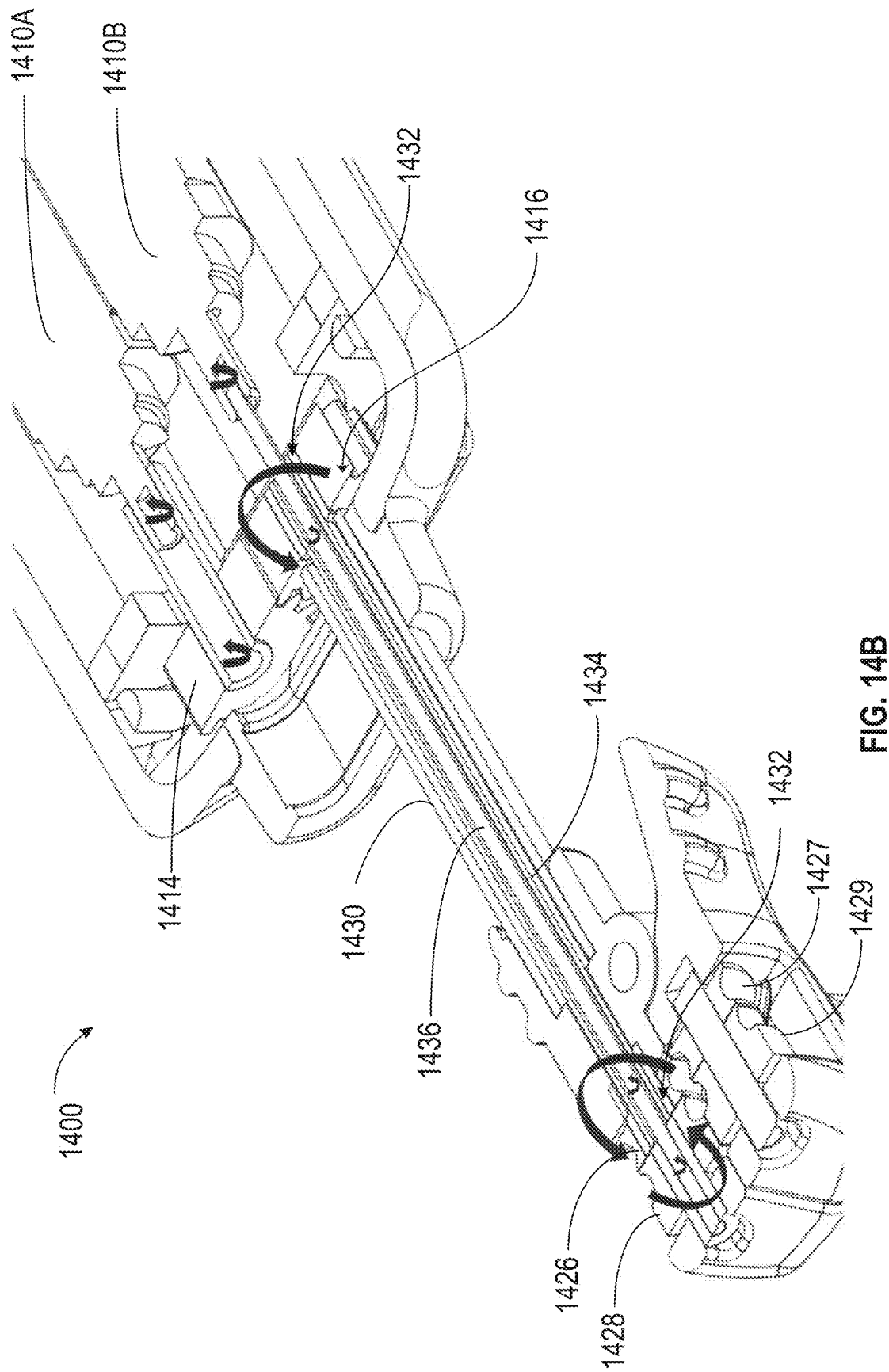
Figure 14C:
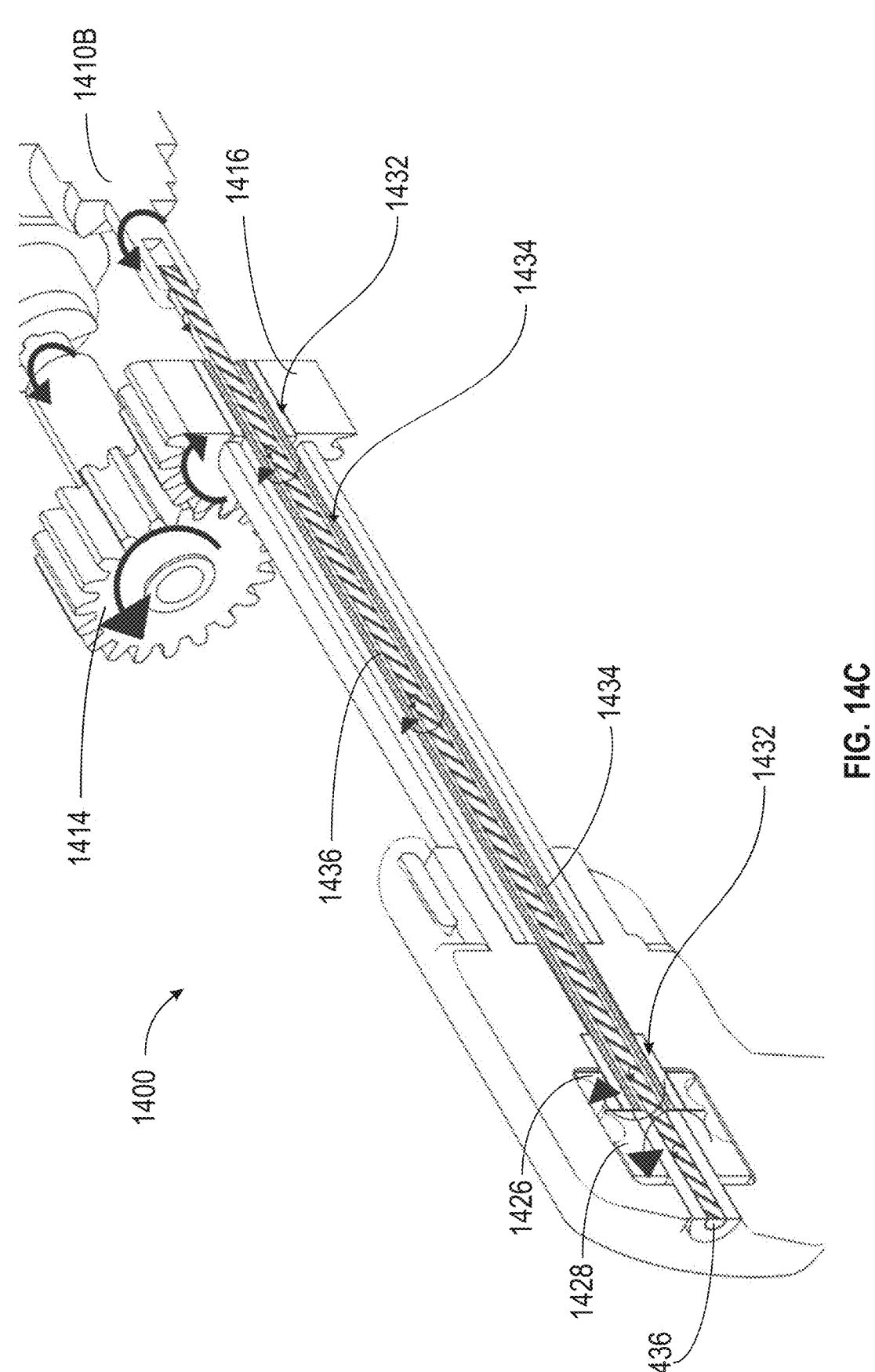
Figure 15:
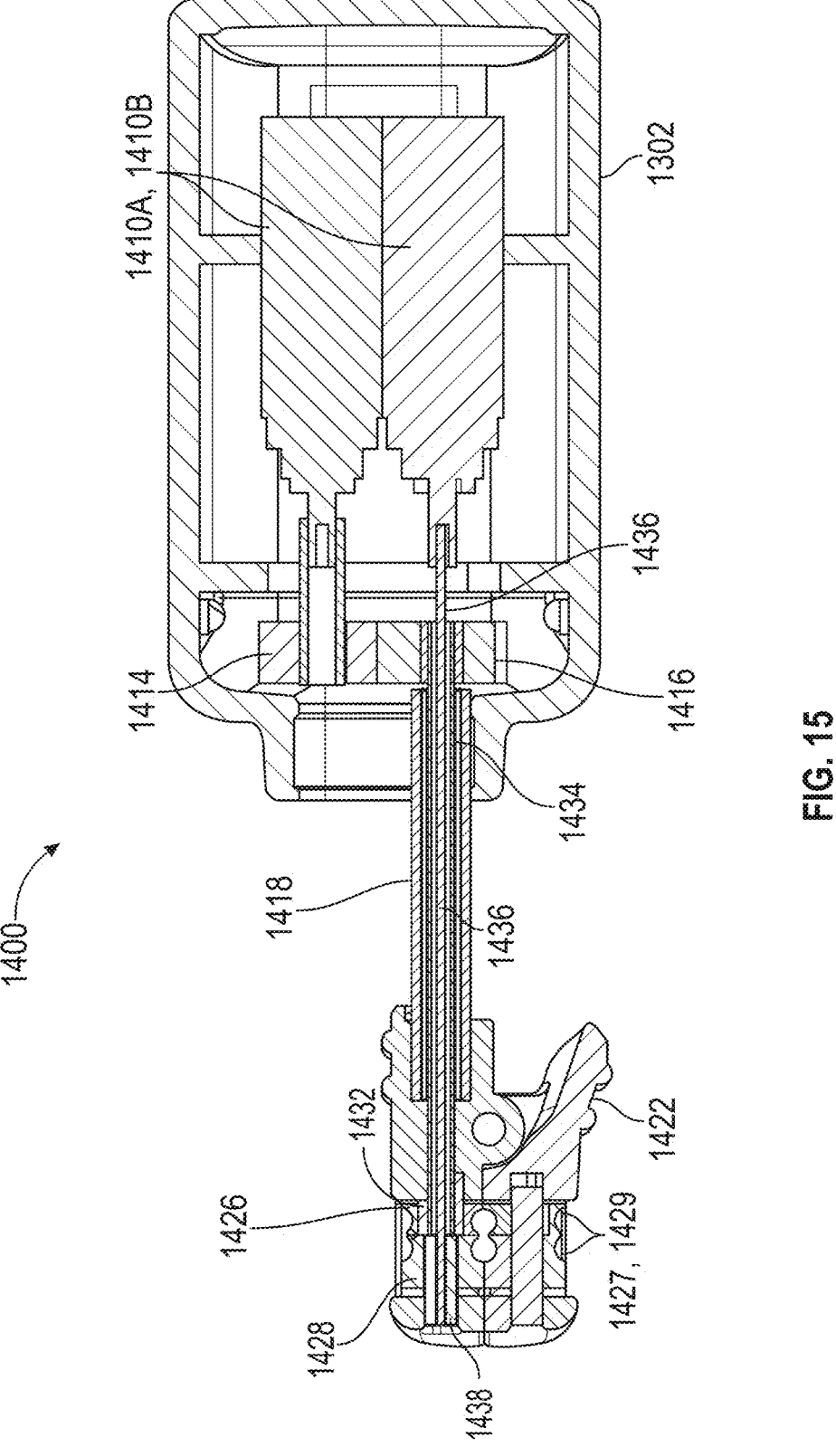

FIGS. 14A-14C and 15, illustrate, by way of example and not limitation, illustrations of a drive mechanism and dual drive head for an implant positioning system. The system, drive mechanism 1400, discussed below can be implemented within the implant positioning unit 1300 discussed above in reference to FIG. 13. FIGS. 14A-15 are discussed below concurrently.

The drive mechanism 1400 can be contained within a housing, such as the housing 1302 of the implant positioning system 1300, as illustrated in FIG. 13. The dual drive head 1422 can be similar to the dual drive head 1306, also illustrated in FIG. 13. The drive mechanism 1400 can include a first motor 1410A and a second motor 1410B. The first motor 1410A can drive a first motor gear 1414. The first motor 1410A gear can in turn engage an outside torque shaft gear 1416. The outside torque shaft gear can correspondingly rotate an outside torque shaft 1434 (shown in FIG. 4B and FIG. 15). The outside torque shaft 1434 can be a flexible cable. The outside torque shaft 1434 can rotate within the adjustable arm 1418. The outside torque shaft 1434 can be hollow, and can be configured to rotate around an inner torque shaft 1436 (shown in FIG. 14B and FIG. 15).

The inner torque shaft 1436 can extend longitudinally within the outer torque shaft 1434. The second motor 1410B can rotate the inner torque shaft 1436 independently of the outer torque shaft gear 1416 and the outer torque shaft 1434. The first motor gear 1414 and the outside torque shaft gear 1416 can therefore drive the outside torque shaft 1434 to drive an outer drive wheel 1426 that can rotate around an outer axle 1432. The outer axle 1432 can rotate independently of an inner drive wheel 1428, which can rotate around an inner axle 1438.

The outer torque shaft 1434 can be rigidly attached to the outer drive wheel 1426. The inner torque shaft 1436 can extend through an inner lumen (or bore or passage) of the outer drive wheel 1426, and the inner torque shaft 1436 can be rigidly attached to the inner drive wheel 1428. The first motor 1410A and the second motor 1410B can thereby independently control the translation of a first elongate member using the outer drive wheel 1426 and a second elongate member using the inner drive wheel 1428 due to the independent control of the inner drive wheel 1428 from the outer drive wheel 1426.

In some examples, a hollow shaft stepper motor can be used in the place of the first motor gear 1414 and outside torque shaft gear 1416 to control the outer torque shaft 1434 and the outside drive wheel 1426, while still allowing the second motor 1410B to control the inner torque shaft 1436 and the inner drive wheel 1428 through an inner lumen of a hollow shaft stepper motor axle. The outer drive wheel 1426 can engage an implant in conjunction with outer idler wheel 1427. Similarly, the inner drive wheel 1428 can engage an implant in conjunction with inner idler wheel 1429. The interaction between drive wheel and idler wheel is similar to that discussed above in reference to previous examples. As discussed, the drive and idler wheel configuration can be modified to include alterative drive mechanism, for example where both wheels are actively or passively driven.

In the case of an cochlear implantation, the inner drive wheel 1428 can advance a pre-curved sheathed electrode into the cochlea, then advance only the electrode out of the sheath and into the cochlea, and finally retract the sheath from the implant, and upon removal, leaving only the implant behind.

FIGS. 14B and 14C include torque vector indicators for various torque shafts and axles. For example, in FIG. 14B, the first motor 1410A imparts a torque in a first direction on the first motor gear 1414, which in turn imparts a torque in an opposing rotational direction on torque shaft gear 1416. The torque shaft gear 1416 is coupled to the outer torque shaft 1434, which also has a torque applied upon rotation of the first motor 1410A in a rotation direction corresponding to the torque shaft gear 1416. As illustrated, the second motor 1410B applies an independent torque on the inner torque shaft 1436, which extends through the outer axle 1432 of the torque shaft gear 1416. Ultimately, the torque applied by the first motor 1410A is transmitted to the outside drive wheel 1426 (via the first motor gear 1414, the torque shaft gear 1416, and the outer torque shaft 1434). The torque applied by the second motor 1410B is transmitted to the inner drive wheel 1428 (via the inner torque shaft 1436).

FIG. 14C provides an additional illustration of how torque vectors are transmitted between various elements of the drive system.

Figure 16:
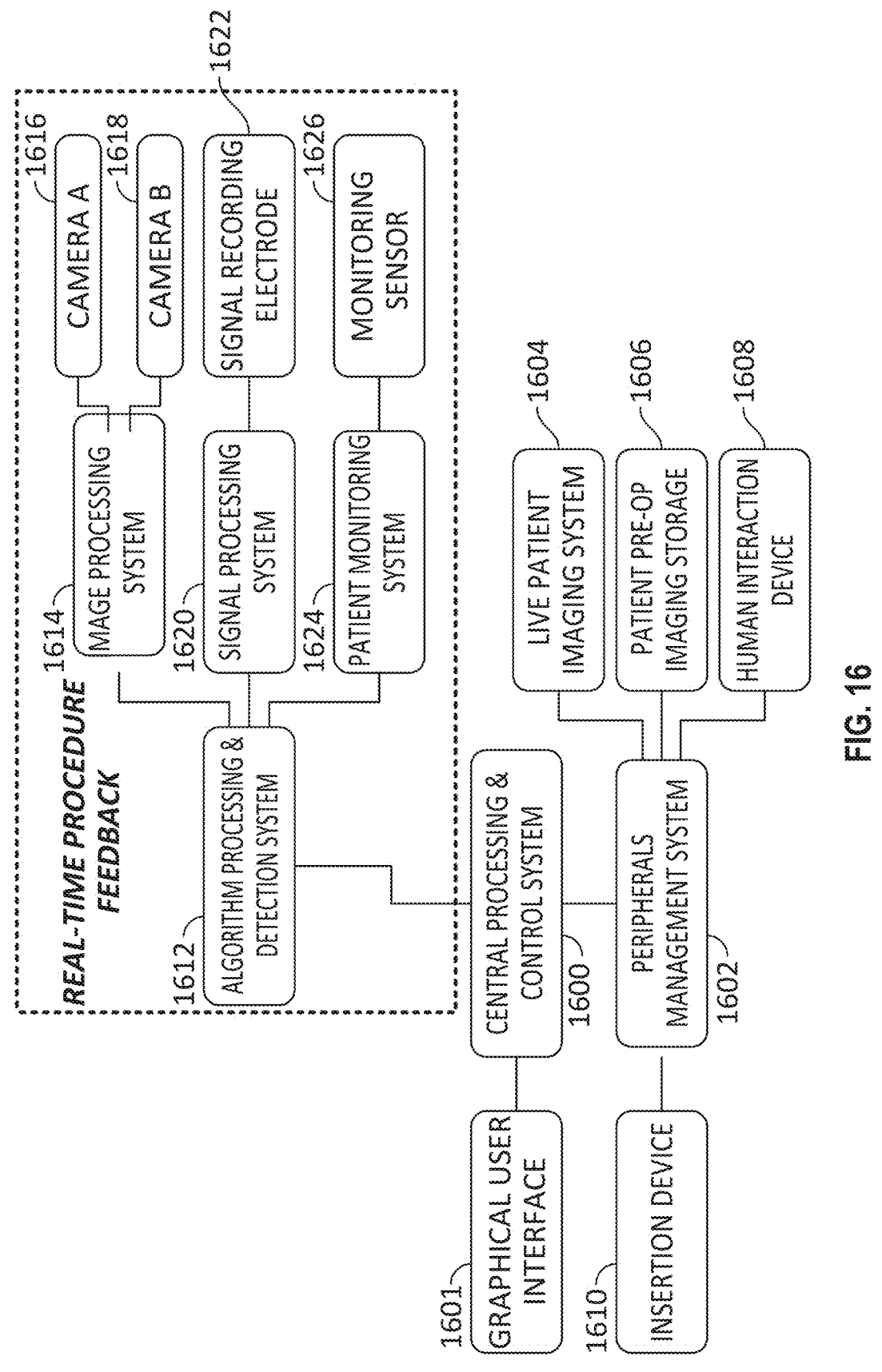
FIG. 16 illustrates, by way of example and not limitation, a block diagram illustrating a surgical insertion vision and control system, in accordance with an example embodiment of the present disclosure.

FIG. 16 illustrates is a block diagram illustrating a surgical insertion vision and control system, in accordance with an example embodiment of the present disclosure. The following introduces each component in the system as depicted in FIG. 16.

1600: Sub-System for storing and updating procedure settings, configuration, and display.

1601: Displays key information to user. Examples of display elements could be multi-dimensional anatomy images, cross-sectional anatomy images, insertion position graphics, buttons for adjusting view and other procedure settings.

1602: Sub-System for managing communication with user-connected devices used for supplying information to, or interacting with, the surgical system.

1604: Source of data used for real-time (live) imaging for visualization and target location information. Examples could include CT, MRI, Fluoroscopy.

1606: Source of data used to create patient-specific visualizations and surgical templates.

1608: Object(s) that allow a user of the system to interact or control procedural actions and/or settings. Examples of this could include Foot pedal, Touchpad, Touchscreen, Hand-Held Controller.

1610: Device used to control the position of insertion implant (as described in other parts of patent) such a robotic drive module, adjustable sheath, etc.

1612: Sub-System which applies algorithms and logic for determining key surgical events and states, which can then be used as feedback source for updating procedure settings and display. Key parameters can include providing system parameters updates and modification based on object positional data over time, physiological patterns, or object angles relative to key points in the surgical site.

1614: Sub-System for handling stereo camera imaging data, processing each camera view to create a multi-dimensional geometric map of the procedure site. This could include detecting important objects in the view and calculating parameters such as location, angle, or distance in relation to a reference point.

1616: Camera in a position to view the surgical site in such that it captures the left field of view in the stereo pair

1618: Camera in a position to view the surgical site in such that it captures the right field of view in the stereo pair

1620: Sub-System for processing electrophysiological signal data. The system is responsible for applying filters to reduce noise, amplification, and data acquisition at a high sampling rate.

1622: Instrument used as the interface of physiological signal waves between the patient and signal acquisition system.

1624: Sub-System for processing input from a variety of sensors. The system can be responsible for interfacing with an integrated sensor to process data from the surgical suite, which then feeds into the motor control algorithm.

1626: A sensor in the surgical suite used to gather data relevant to the procedure. This sensor input could be of type: audio device, video device, nerve and muscular sensing, tactical feedback device, temperature sensing, force sensing.

Figure 17:
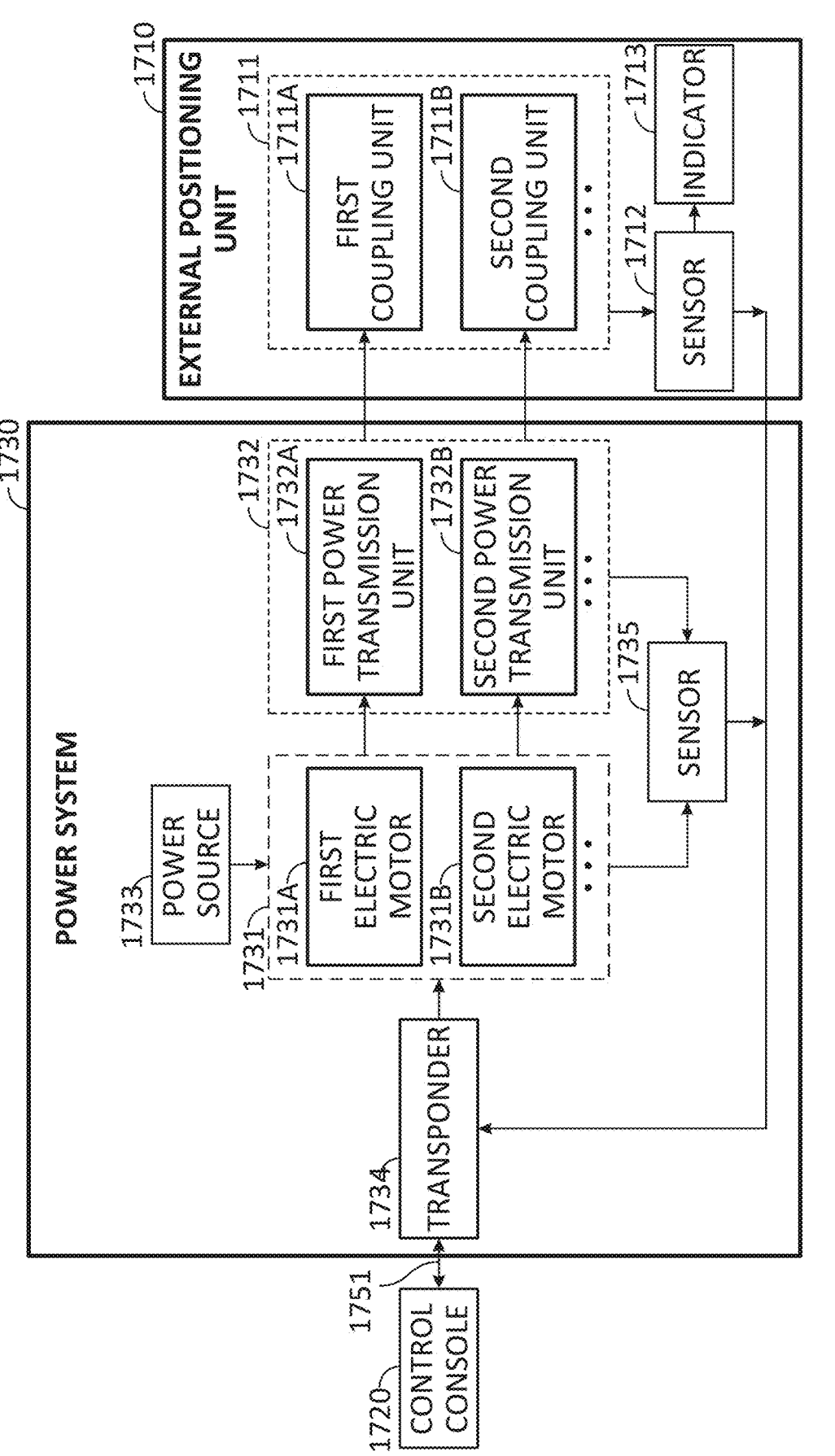
FIG. 17 illustrates, by way of example and not limitation, a block diagram of a power system that provides driving force and motion to the external positioning unit to propel and position an implant, in accordance with an example embodiment of the present disclosure.

FIG. 17 illustrates, by way of example and not limitation, a block diagram of a power system 1730 that provides driving force and motion to the external positioning unit 1710 to deliver and position an implant. The power system 1730 can be an embodiment of the power system 1730 of the robotically assisted implantation system 1700 as illustrated in FIG. 1. The power system 1730 can provide a one-degree of freedom, or multiple-degrees of freedom, control over the elongate member 1741 of the implant.

The power system 1730 can include one or more electric motors 1731 each coupled to respective power transmission units 1732. The one or more power transmission units 1732 are each coupled to respective coupling units 1711 in the external positioning unit 1710, which is an embodiment of the implant positioning unit 210 as illustrated in FIG. 2. The one or more electric motors 1731 can be electrically coupled to a power source 1733. In an example, the power source 1733 can include a rechargeable power source, such as a rechargeable battery or a supercapacitor. The rechargeable power source can be charged wirelessly by a portable device such as a handheld device with circuitry configured to transfer energy to the rechargeable power source through electromagnetic induction.

The one or more electric motors 1731 can be of the same or different types of motors. Examples of the electric motors 1731 can include stepper motors, direct current (DC) motors, piezo electric motors, ultrasonic motors, or linear motors, among others. The one or more electric motors 1731 can each be coupled to a transponder 1734 that can receive motion control signals from the control console 1720 via the communication link 1751. The control console 1720 can generate respective motion control signal for each of the electric motor 1731 according to the motion control instructions provided by the user. In an example, a user can independently program (by inputting the motion control instructions) and control the operation of each of the electric motors 1731, such as via the user input module 1725. The motion control signal specifies the configurations and input voltage or current to the respective electric motor 1731, which can generate the desired torque, speed, or rotation direction.

In response to the received motion control signal, the one or more electric motors 231 can generate respective driving force and motion that control various motion parameters of the elongate member 141 of the implant via the power transmission unit 232. The power transmission units 232 can adjust the speed or torque output from the motors, and to deliver specific output to the respective coupling units 211. Examples of the power transmission units 232 can include spur gears, helical gears, planetary gears or gearhead, worm gears, miniature pulleys, or timing belts, among others.

The electrical motors 1731 can include at least a first electric motor 1731A and a second electric motor 1731B. The first electric motor 1731A can generate driving force and motion, transmitted to the first coupling unit 1711A via the first power transmission unit 1732A, to control one or more parameters associated with a motion along a first orientation, such as a translational motion. Examples of the translational motion parameters can include movement rate, direction, distance relative to a reference point, a position of a distal end of the elongate member, or an amount of axial force applied to the elongate member. The second electric motor 1731B can generate driving force and motion that is transmitted to the second coupling unit 1711B via the second power transmission unit 1732B, and control one or more parameters associated with a motion along a second orientation, such as a rotational motion. Examples of the rotational motion parameters can include angular position, angular displacement, angular velocity, or an amount of lateral or rotational force applied to the elongate member. The first and second electrode motors, along with the respective power transmission units and the coupling units in the external positioning unit, can provide a flexible and precise control of the motion of the implant on multiple degrees of freedom. This can allow for optimal positioning of the implant at the target implantation site, such as placement of cochlear implant electrode array in close proximity to auditory nerve cells and neurons.

One or more sensors can be configured to sense information about position and motion of the implant during implantation, such as a sensor 1735 in the power system 1730, or a sensor 1712 in the external positioning unit 1710. In an example, one or more linear or rotary encoders can be attached to the electric motor 1731, the power transmission unit 1732, or the coupling units 1711 to detect the information about position of the implant. In another example, one or more Hall effect sensors can be integrated in the electric motor 1731. In yet another example, one or more optical sensors can be attached to the coupling unit 1711. In some examples, the sensor 1735 or the sensor 1712 can include capacitive and/or optical sensors configured to detect implant motion.

In addition to or in lieu of the motion and position sensing, the sensor 1735 or the sensor 1712 can include force sensors to sense a parameter indicative of force or friction imposed on the implant during the implant advancement, such as axial, lateral, or radial forces when the cochlear implant interacts with cochlea wall and surrounding tissues. Examples of the force sensors can include resistors, capacitive sensors, piezoelectric material, or a strain gauge, among others. In an example, the force can be indirectly sensed by measuring the current supplied to the electric motor 1731. The current measurement can be transmitted to the control console 1720, where it is converted to the force (or torque) using the torque-current curve predetermined and stored in the memory circuit 1724.

The information acquired by the sensors 1735 and the sensors 1712 can be forwarded to the control console 1720 via the communication link 1751. The sensor information can be displayed or otherwise presented in a specific media format in the output module 1726. In an example, the external positioning unit 1710 can include an indicator 1713 coupled to the sensor 1712. The indicator 1713 can produce a visual or audio notification in response to the sensed sensor signal satisfies a specific condition. In an example, the indicator 1713 can include a light emitting diode (LED) that can be turned on when the sensed sensor signal indicates the implant reaches the target implantation site. In some examples, the indicator 1713 can include a plurality of LEDs with different colors or different pre-determined blinking patterns. The LED colors or the blinking patterns can correspond to various events encountered during the implantation procedure.

The control console 1720 can generate and modify the motion control signal based on user input of motion control instructions to control the motion of the elongate member of the implant. Alternatively, the control console 1720 can automatically adjust the motion control according to the sensed motion parameters. In an example, if the sensed force imposed on the implant exceeds a threshold value, the control console 1720 can automatically halt the ongoing motion of the implant or reduce the speed of motion. An alert can be generated and presented on to a user via the control console 1720 (which can include a user interface). This can be a programmable safety mechanism to prevent unintended tissue trauma or damage to the implant. If the implant movement distance has reached a pre-determined target movement distance, the control console 1720 can automatically withhold the motion of the implant.

Figure 18:
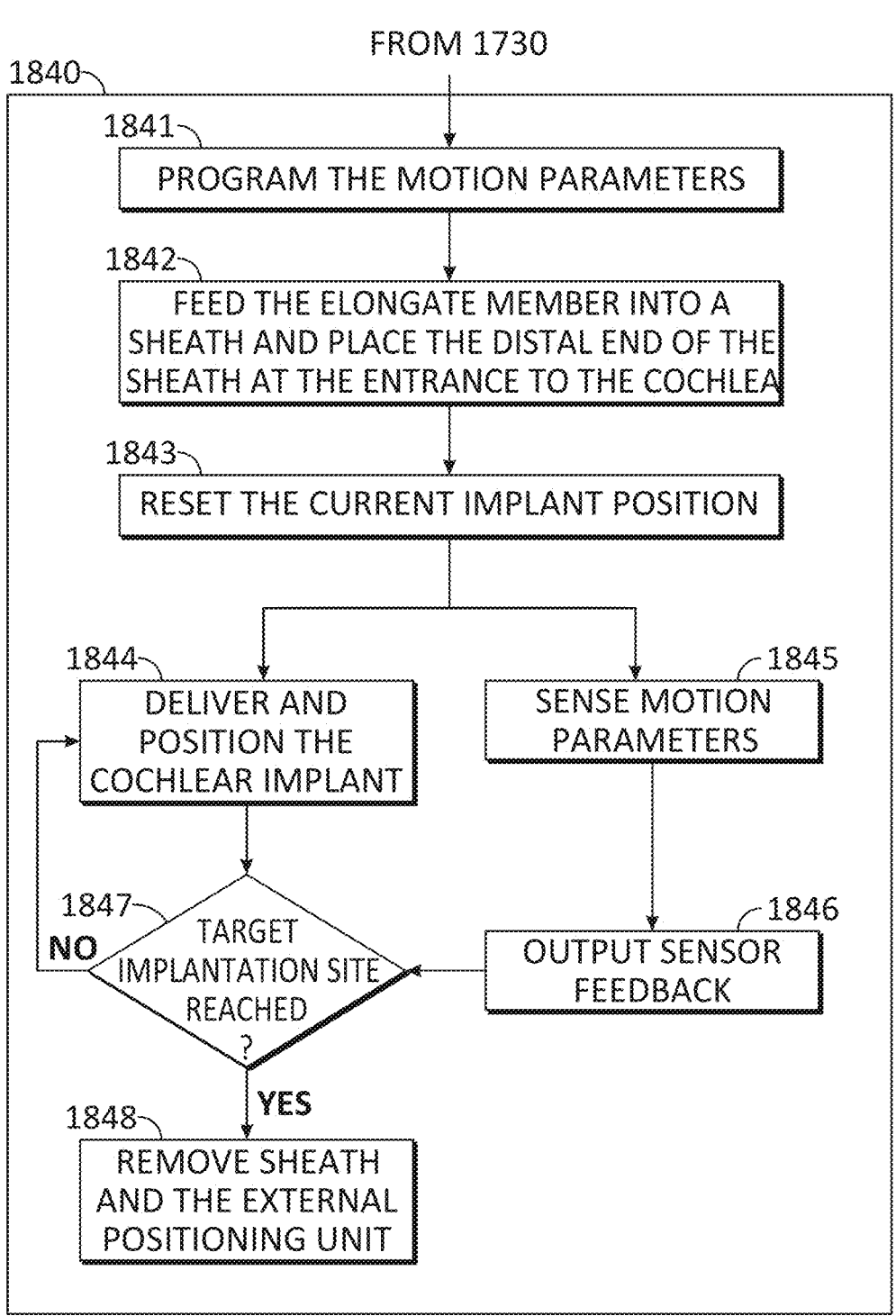
FIG. 18 illustrates, by way of example and not limitation, a method for sensor-based robotic control of a cochlear implant, in accordance with an example embodiment of the present disclosure.

FIG. 18 illustrates, by way of example and not limitation, a method 1840 for sensor-based robotic control of a cochlear implant. The method 1840 is an embodiment of the step 540 of the method 500 as illustrated in FIG. 5. The method 1840 can be used for operating a non-implantable, robotically controlled implantation system, such as the robotically assisted implantation system 100.

Once the external positioning unit is affixed to the patient at 530, motion control parameters can be programmed at 1841, such as via the user interface module 121 of the control console 120. The motion control parameters can characterize desired motion of the elongate member of the implant. Examples of the motion parameters can include a target movement rate, a target movement direction or orientation, a target movement distance, a target position of a distal end of the elongate member, or a target amount of force imposed on the elongate member. In some examples, a pre-determined implant delivery protocol can be programmed into the system. The implant delivery protocol defines target values of a plurality of motion parameters. A user can adjust one or more motion parameters, modify an existing implant delivery protocol, or switch to a different implant delivery protocol during the implant delivery procedure.

At 1842, the elongate member of the implant can be fed into a sheath, and a distal end of the sheath can be introduced to the entrance of the surgical site, such as a cochlear entrance for cochlear implant placement. As illustrated in FIGS., the sheath can partially or completely enclose the elongate member of the implant to provide resilient support to the elongate member, thereby keeping the implant on track from the external positioning unit and the surgical entrance of the target implantation site. A surgeon can advance the implant through the external positioning unit via user input controls on the user interface module, or through a peripheral input device such as a foot pedal or a handheld device, until the distal tip of the elongate member is in line with distal end of the sheath. The distal end of the sheath can then be positioned at the entrance to the cochlea. The distal end of the sheath can be fixed or reversibly stabilized at a designated position of the surgical opening of the implantation. In an example of cochlear implant, the distal end of the sheath can be stabilized at the cochlea round window (RW) or cochleostomy site by closely matching tube diameters to the RW niche or cochleostomy dimensions.

Once the sheath is positioned and stabilized in place, the implant can be robotically advanced via the control console or one or more of the peripheral input controls coupled to the control console. At 1843, the current implant position can be reset to zero, such as by a short press of the foot pedal. At 1844, the cochlear implant can be delivered and positioned to the target site of cochlear region, according to the programmed motion control parameters. The motion of the implant can be activated by a surgeon using the control buttons on the control console, or a peripheral control device, such as a foot pedal or a handheld device. The movement of the implant can be activated at intervals of a predetermined step size. In an example, for cochlear implant, the target movement rate is approximately 100-micron intervals. In an example, the target movement distance is approximately 1-35 millimeters.

During the implantation process, one or more sensors can sense information about position and motion of the implant at 845. The sensor can be positioned at the electric motor, the power transmission unit, or inside the external positioning unit such as at the drive wheel or idler wheel. Examples of the sensors can include encoders, Hall effect sensors, or optional sensors for detecting the position of the implant, capacitive sensors for detecting implant motion, or force sensors for sensing a parameter indicative of force or friction imposed on the implant during the implant advancement, such as axial, lateral, or radial insertion force as the implant advances into the cochlea. The force can also be indirectly sensed by measuring the current supplied to the electric motor.

At 1846, the sensor feedback on implant can be transmitted to the control console and output to a user or a process. In an example, a human-perceptible presentation of the sensed feedback, including one or more parameters on the position of the implant, motion of the implant, or the force or friction applied to the implant motion, can be generated. The presentation can include real-time visual or audible notification with specified patterns corresponding to different types of events encountered during implantation. The audible and visual feedback can also signal to the user that the sensed implant position, motion, or the forces has exceeded the target parameter values such as programmed by the user.

At 1847, the sensor feedback is checked to determine whether target implantation site has been reached. A target implantation site is reached if the sensed distance of insertion reaches the user programmed target distance within a specified margin. A visual indicator, such as a light emitting diode (LED) or an on-screen visual indicator on the display screen with specified color or pattern can signal to the user a successful positioning of the implant at the target implantation site. Alternatively or additionally, an audial notification, such as a beep or an alarm with a specific tone, frequency, or a specific pattern (e.g., continuous, intermittent, pulsed, sweep-up, or sweep-down sound) can go off to signal to the user successful positioning of the implant at the target implantation site.

If at 1847 the target implantation site is not reached, then the delivery and positioning process can be continued at 1844. If at 1847 it is determined that the target implantation site has been reached, then at 1848, the implant can be released and positioned at the target implant site, and a sheath and the external positioning unit can be removed. The sheath can include disengagement means to facilitate separation of the sheath from the elongate member, while at the same time avoiding excessive damaging forces on the implant, such as to prevent dislodgement of the implant from the implantation site upon removal of the sheath.

Figure 19:
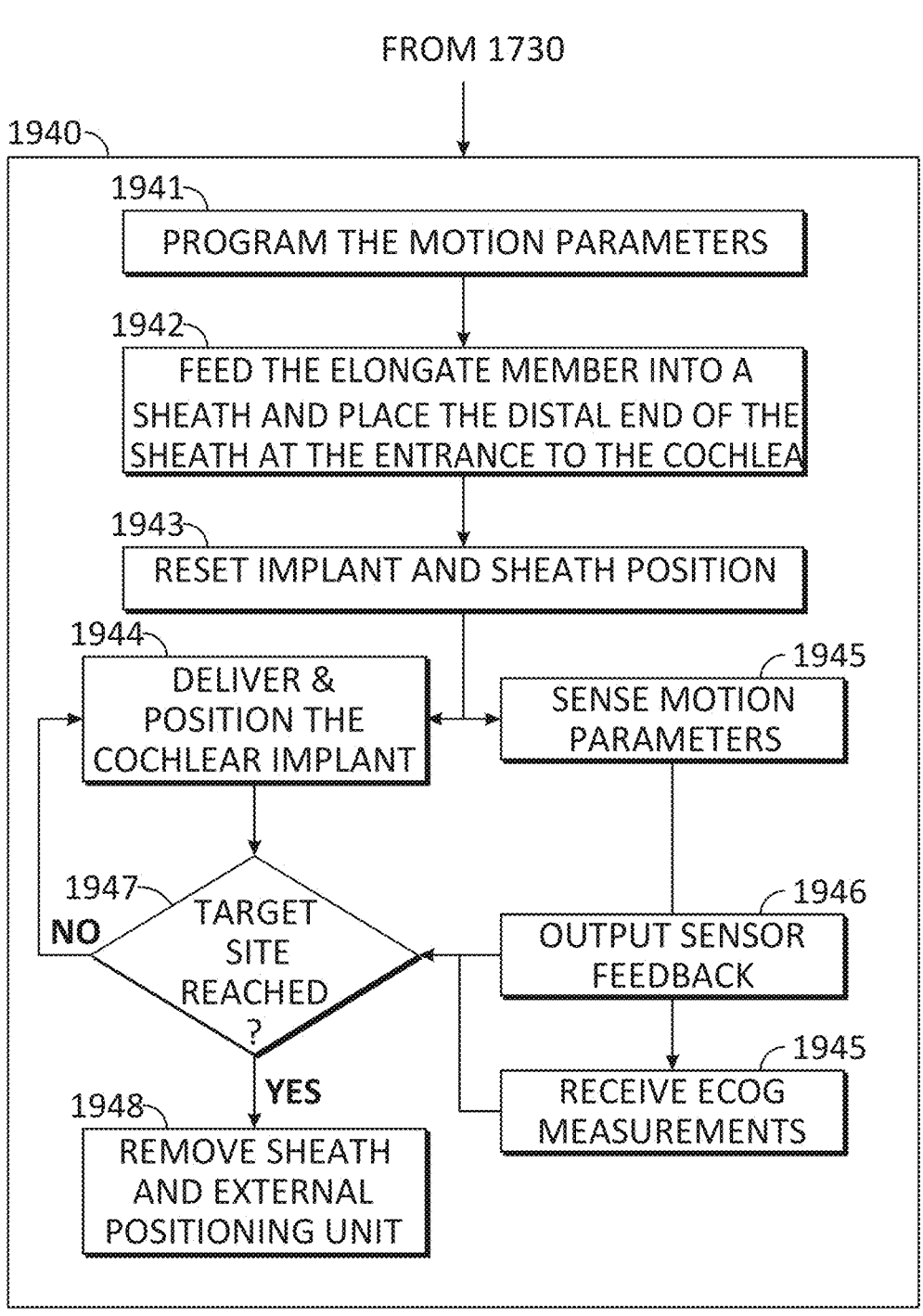
FIG. 19 illustrates, by way of example and not limitation, a method for sensor-based and measurement-based real-time control of implant delivery and positioning, in accordance with an example embodiment of the present disclosure.

FIG. 19 illustrates, by way of example and not limitation, a method for sensor-based and measurement-based real-time control of implant delivery and positioning. The method 1940, like method 1840 discussed above, is an embodiment of the step 540 of the method 500 as illustrated in FIG. 5. The method 1940 can be used for operating a non-implantable, robotically controlled implantation system, such as the robotically assisted implantation system 100. In this example, the method 1940 includes operations identical to method 500 with the addition of receiving ECoG measurements at 1945. As discussed in reference to FIG. 9 above, the ECoG measurements can be utilized by the external positioning unit 110 and/or control console 120 to assist in controlling implant positioning and delivery.

The method 1940 can include an operation for receiving ECoG measurements, which can then be utilized in determining whether a target site is reached at 1947. As discussed above, ECoG measurements can be monitored to determine when an optimal implant position is reached or for potential issues with the implant delivery.

Figure 20:
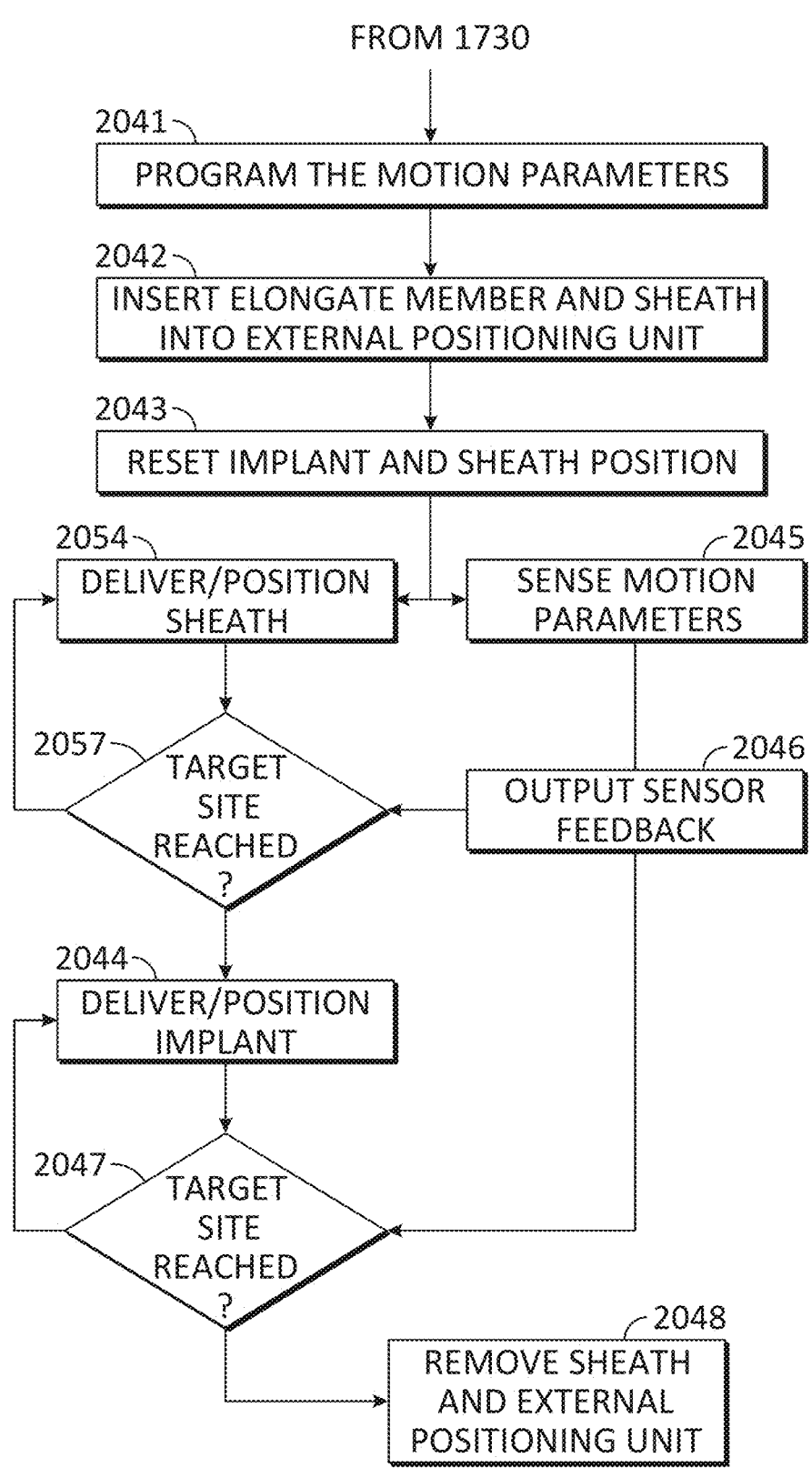
FIG. 20 illustrates, by way of example and not limitation, a method for real-time control of implant and guide sheath delivery and positioning, in accordance with an example embodiment of the present disclosure.

FIG. 20 illustrates, by way of example and not limitation, a method for real-time control of implant and guide sheath delivery and positioning. The method 2040, like methods 1840 and 1940 discussed above, is an embodiment of the step 540 of the method 500 as illustrated in FIG. 5. The method 2040 can be used for operating a non-implantable, robotically controlled implantation system, such as the robotically assisted implantation system 100. In this example, the method 2040 includes operations identical to method 540 with the addition of operations for monitoring the positioning and delivery of an insertion sheath, such as insertion sheath 2002. As illustrated, the method 2040 includes additional operations 2054 and 2057 for delivering and/or positioning a sheath at 2054 and determining whether the sheath has reached the target position at 2057. Monitoring the sheath insertion can involve similar sensor feedback as used with electrode insertion. Otherwise, the operations of method 2040 mirror those discussed in reference to methods 1840 and 1940 above.

Some examples or embodiments can include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods.

Various embodiments are illustrated in the figures above. One or more features from one or more of these embodiments can be combined to form other embodiments. The method examples described herein can be machine or computer-implemented at least in part. Some examples can include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A method for robotically assisted positioning of an implant, the method comprising:
   positioning an elongate member adjacent to an implantation site using an implant positioning system including a drive head separated from a power source;
   determining, using the implant positioning system, that a distal end of the elongate member is in a first target position;
   positioning an implant along the elongate member, using the implant positioning system, into the implantation site including guiding the implant using the drive head to limit rotation or twisting during translation;
   monitoring a position of the implant; and
   determining, using the implant positioning system, that a distal end of the implant has reached a second target position.

2. The method of claim 1, wherein the determining that the distal end of the implant reached the second target position includes monitoring electrophysiological measurements to determine an optimal implant position.

3. The method of claim 2, wherein monitoring the electrophysiological measurements includes receiving real-time feedback signals from a biofeedback system communicatively coupled to the implant positioning system.

4. The method of claim 1, wherein the determining that the distal end of the implant reached the second target position includes monitoring real-time signals from a biofeedback system communicatively coupled to the implant positioning system, the real-time signals including data representative of electrophysiological, biological or image based sensor data.

5. The method of claim 1, wherein the determining that the distal end of the implant reached the second target position includes monitoring a motion control parameter for the implant.

6. The method of claim 5, wherein monitoring the motion control parameter includes monitoring one or more of movement rate, movement distance, or force imposed on the implant.

7. The method of claim 5, wherein monitoring the motion control parameter includes receiving sensor data from one or more sensors from a group of sensors and imaging technologies consisting of:

an encoder;

a hall effect sensor;

a capacitive sensor;

a force sensor;

radiography;

magnetic resonance imaging;

optical coherence tomography;

ultrasonography; and impedance measures.

8. The method of claim 1, wherein guiding the implant using the drive head includes capturing an access tab attached to the implant.

9. The method of claim 1, wherein positioning the implant includes engaging the implant with a coupling unit of the drive head to translate the implant.

10. The method of claim 9, wherein the coupling unit includes two wheels configured to engage at least a portion of the implant, through compression between portions of radial outer surfaces of the at least two wheels, and wherein translating the implant occurs through rotation of the wheels via friction generated by the compression.

11. A method for mechanically assisted implant positioning, the method comprising:

coupling an implant to a drive head of an implant positioning system to control rotation and twisting during linear translation of the implant along an elongate member portion of the implant positioning system;

positioning the elongate member adjacent to an implantation site;

determining, using the implant positioning system, that a distal end of the elongate member is in a first target position;

translating the implant along the elongate member, using the implant positioning system, into the implantation site including powering movement of the implant using the drive head receiving rotational input from a remote power source;

monitoring a position of the implant; and determining, using the implant positioning system, that a distal end of the implant has reached a second target position.

12. The method of claim 11, wherein receiving rotational input from a remote power source includes receiving the rotational input via a flexible drive shaft coupled to the drive head.

13. The method of claim 12, wherein receiving rotational input from a remote power source includes an electric motor within the remote power source driving the flexible drive shaft coupled to the drive head.

14. The method of claim 11, wherein receiving rotational input from a remote power source includes receiving power and data communications at the remote power source via a USB connection with an external computing device.

15. The method of claim 11, wherein the determining that the distal end of the implant reached the second target position includes monitoring electrophysiological measurements to determine an optimal implant position.

16. The method of claim 15, wherein monitoring the electrophysiological measurements includes receiving real-time feedback signals from a biofeedback system communicatively coupled to the implant positioning system.

17. The method of claim 11, wherein the determining that the distal end of the implant reached the second target position includes monitoring real-time signals from a biofeedback system communicatively coupled to the implant positioning system, the real-time signals including data representative of electrophysiological, biological or image based sensor data.

18. The method of claim 11, wherein the determining that the distal end of the implant reached the second target position includes monitoring a motion control parameter for the implant.

19. The method of claim 18, wherein monitoring the motion control parameter includes monitoring one or more of movement rate, movement distance, or force imposed on the implant.

20. The method of claim 18, wherein monitoring the motion control parameter includes receiving sensor data from one or more sensors from a group of sensors and imaging technologies consisting of:

an encoder;

a hall effect sensor;

a capacitive sensor;

a force sensor;

radiography;

magnetic resonance imaging;

optical coherence tomography;

ultrasonography; and impedance measures.

* * * * *